(12) United States Patent
McBride et al.

(10) Patent No.: US 9,605,033 B2
(45) Date of Patent: Mar. 28, 2017

(54) **IMMUNOREACTIVE GLYCOPROTEIN GP19 OF *EHRLICHIA CANIS***

(71) Applicant: Research Development Foundation, Carson City, NV (US)

(72) Inventors: Jere W. McBride, Leauge City, TX (US); Christopher Kuyler Doyle, Brussels (BE)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 14/729,758

(22) Filed: Jun. 3, 2015

(65) Prior Publication Data

US 2015/0338406 A1 Nov. 26, 2015

Related U.S. Application Data

(62) Division of application No. 12/377,926, filed as application No. PCT/US2007/075343 on Aug. 7, 2007.

(60) Provisional application No. 60/841,465, filed on Aug. 31, 2006.

(51) Int. Cl.
| | |
|---|---|
| *G01N 33/569* | (2006.01) |
| *C07K 14/29* | (2006.01) |
| *C07K 14/195* | (2006.01) |
| *C07K 16/12* | (2006.01) |
| *A61K 39/00* | (2006.01) |

(52) U.S. Cl.
CPC ........ *C07K 14/195* (2013.01); *C07K 16/1246* (2013.01); *G01N 33/56911* (2013.01); *A61K 39/00* (2013.01); *C07K 2317/34* (2013.01); *G01N 2333/29* (2013.01); *G01N 2800/26* (2013.01)

(58) Field of Classification Search
CPC ........... G01N 33/56911; G01N 33/569; G01N 2333/29; G01N 2800/26; C07K 16/1246; C07K 2317/34; C07K 14/195; A61K 39/00
See application file for complete search history.

(56) References Cited

U.S. PATENT DOCUMENTS

| 7,842,473 B2 | 11/2010 | Krah et al. |
| 2006/0234322 A1 | 10/2006 | Krah et al. |

FOREIGN PATENT DOCUMENTS

| WO | WO 01-82862 | 11/2001 |
| WO | WO 2006-107924 | 10/2006 |

OTHER PUBLICATIONS

Cardenas, "Enzyme-linked immunosorbent assay with conserved immunoreactive glycoproteins gp36 and gp19 has enhanced sensitivity and provides species-specific immunodiagnosis of Ehrlichia canis infection," *Clin Vaccine Immunol.*, 14(2):123-128, 2007.
Database Accession No. Q3YSZ1, "Major outer membrane protein p19," Uniprot, 2005.
FASTest® *Ehrlicha canis* kit, Intructinos for Use, Megacor, 2012.
GenBank Accession No. CP000107 [GI:72393774], "Ehrlichia canis str. Jake, complete genome," NCBI, 2005.
Kuriyama et al., "Monoclonal anti-dipeptide antibodies cross-react with detyrosinated and glutamylated forms of tubulins," *Cell Motility & the Cytoskeleton*, 30:171-182, 1995.
Mavromatis et al., "The genome of the obligately intracellular bacterium Ehrlichia canis reveals themes of complex membrane structure and immune evasion strategies," *J Bacteriol.*, 188(11):4015-4023, 2006.
McBride et al., "Identification of a glycosylated Ehrlichia canis 19-kilodalton major immunoreactive protein with a species-specific serine-rich glycopeptide epitope," *Infect Immun.*, 75(1):74-82, 2007.
McBride et al., "Kinetics of antibody response to Ehrlichia canis immunoreactive proteins," *Infect Immun.*, 71(5):2516-2524, 2003.
McBride et al., "Molecular cloning of the gene for a conserved major immunoreactive 28-kilodalton protein of Ehrlichia canis: a potential serodiagnostic antigen," *Clin Diagn Lab Immunol.*, 6(3):392-399, 1999.
Ndip, "Ehrlichial infection in Cameroonian canines by Ehrlichia canis and Ehrlichia ewingii," *Vet Microbiol.*, 111(1-2):59-66, 2005.
Office Action issued in Australian Application No. 2007348944, mailed Jan. 20, 2012.
Office Action issued in Canadian Application No. 2,662,246, mailed Mar. 26, 2015.
Office Action issued in Canadian Application No. 2,662,246, mailed Apr. 10, 2014.
Office Action issued in Canadian Application No. 2,662,246, mailed Apr. 4, 2013.
Office Action issued in Canadian Application No. 2,662,246, mailed Mar. 12, 2012.
Office Action issued in European Application No. 07873953, mailed May 4, 2010.
Office Action issued in European Application No. 07873953, mailed Jun. 18, 2009.
Office Action issued in Japanese Application No. 2009-526792, and English language translation thereof, mailed Jul. 5, 2012.
Office Action issued in Japanese Application No. 2013-257840, mailed Apr. 6, 2015, and English language translation thereof.
Office Action issued in U.S. Appl. No. 12/377,926, mailed Apr. 18, 2014.
Office Action issued in U.S. Appl. No. 12/377,926, mailed Aug. 29, 2013.
Office Action issued in U.S. Appl. No. 12/377,926, mailed Feb. 21, 2012.
Office Action issued in U.S. Appl. No. 12/377,926, mailed Jan. 31, 2014.
Office Action issued in U.S. Appl. No. 12/377,926, mailed May 24, 2012.
Office Action issued in U.S. Appl. No. 12/377,926, mailed Oct. 24, 2012.

(Continued)

*Primary Examiner* — S. Devi
(74) *Attorney, Agent, or Firm* — Parker Highlander PLLC

(57) ABSTRACT

The present invention concerns gp19 immunoreactive compositions for *E. canis* and compositions related thereto, including vaccines, antibodies, polypeptides, peptides, and polynucleotides. In particular, epitopes for *E. canis* gp19 are disclosed.

5 Claims, 9 Drawing Sheets

(56) References Cited

OTHER PUBLICATIONS

Office Action issued in U.S. Appl. No. 12/377,926, mailed Sep. 3, 2014.
Opposition to European Application No. EP 2064231 filed Jul. 24, 2013 (and English language translation thereof).
PCT International Preliminary Report on Patentability issued in International Application No. PCT/US2007/075343, mailed Mar. 3, 2009.
PCT International Search Report and Written Opinion issued in International Application No. PCT/US2007/075343, mailed Jul. 31, 2008.
Skolnick et al., "From genes to protein structure and function: novel applications of computational approaches in the genomic era," *Trends in Biotechnology*, 18:34-39, 2000.
Western blot, from Wikipedia, 2014.

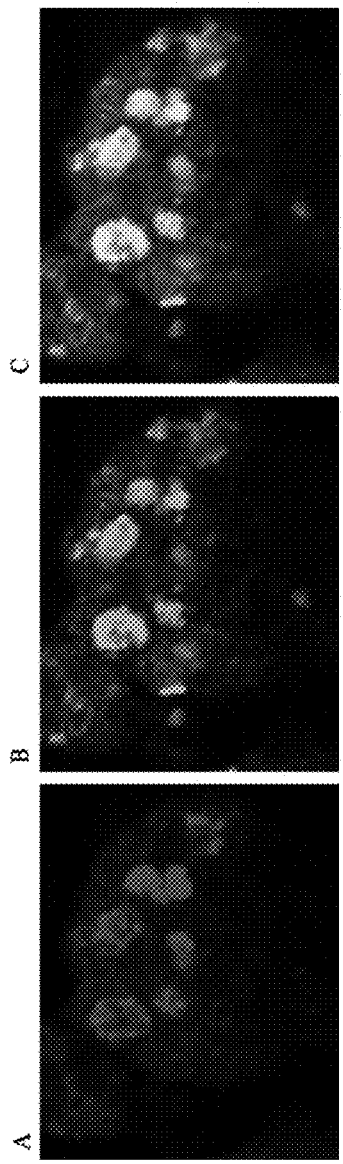
FIGS. 8A-C

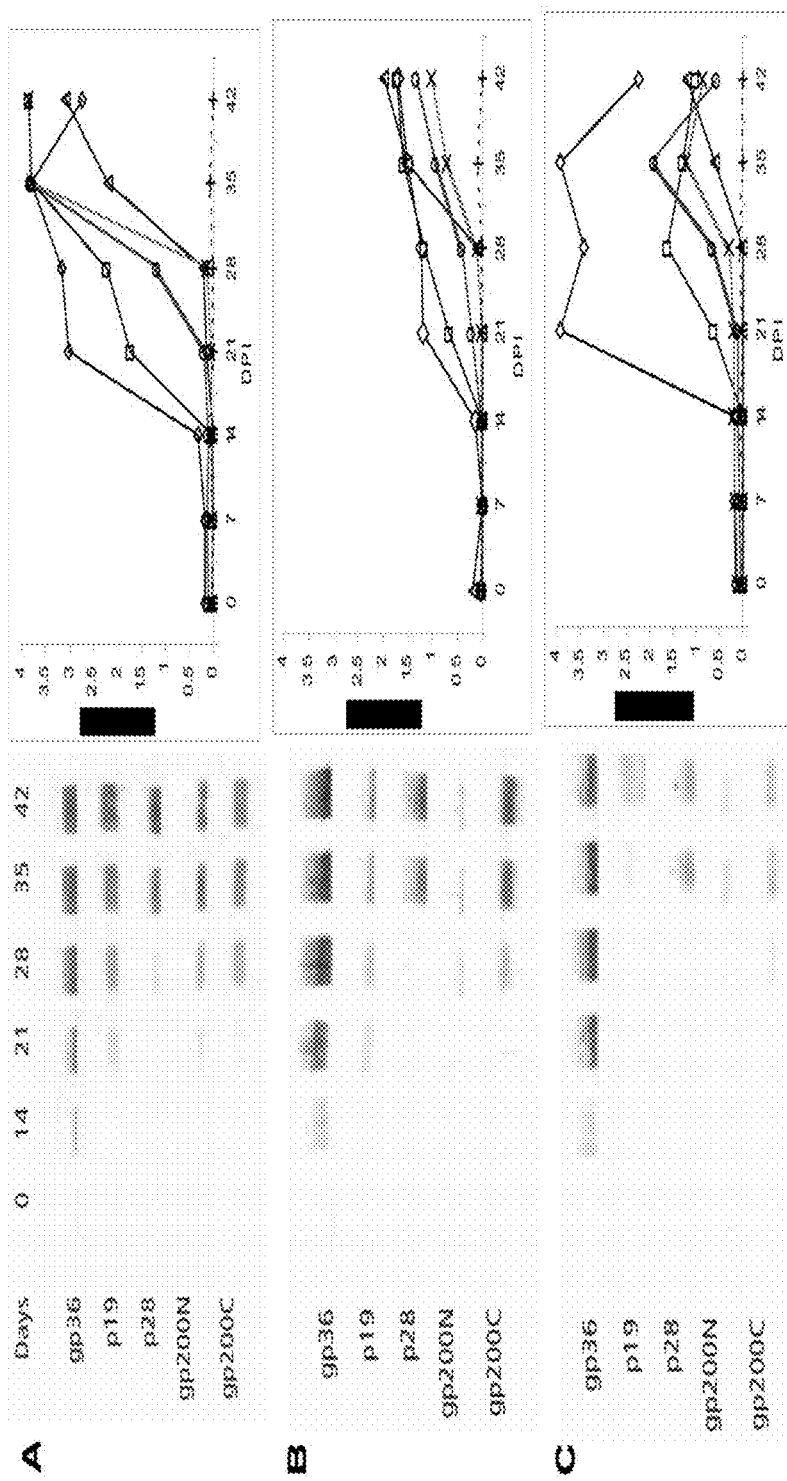
FIGS. 9A-C

IMMUNOREACTIVE GLYCOPROTEIN GP19 OF EHRLICHIA CANIS

CROSS-REFERENCE TO RELATED APPLICATIONS

This application is a divisional of U.S. application Ser. No. 12/377,926, filed Sep. 3, 2010, which is a national phase application under 35 U.S.C. §371 of International Application No. PCT/US2007/075343, filed Aug. 7, 2007, which claims benefit of priority to U.S. Provisional Application No. 60/841,465, filed Aug. 31, 2006. The entire text of each of the above referenced disclosures is specifically incorporated herein by reference.

STATEMENT REGARDING FEDERALLY SPONSORED RESEARCH OR DEVELOPMENT

This invention was made with Government support under grant numbers R01 AI 071145-01 and 1 P41 RR018502-01 awarded by the National Institutes of Health. The Government has certain rights in the invention.

FIELD OF THE INVENTION

The present invention concerns at least the fields of molecular biology, cell biology, pathology, and medicine, including veterinary medicine. In specific aspects, the present invention concerns immunoreactive gp19 compositions in *E. canis*.

BACKGROUND OF THE INVENTION

*Ehrlichia canis* is a tick-transmitted obligately intracellular bacterium that causes moderate-to-severe and sometimes fatal disease in wild and domestic canids. The genomes of *E. canis* and other organisms in the genus, including *E. chaffeensis* and *E. ruminantium*, exhibit a high degree of genomic synteny, paralogous protein families, a large proportion of proteins with transmembrane helices and/or signal sequences, and a unique serine-threonine bias associated with potential for O-glycosylation and phosphorylation, and have tandem repeats and ankyrin domains in proteins associated with host-pathogen interactions (Collins et al., 2005; Hotopp et al., 2006; Frutos et al., 2006; Mavromatis et al., 2006). A small subset of the more than 900 proteins encoded by each of these genomes are recognized by antibody (Doyle et al., 2006; McBride et al., 2003; McBride et al., 2000; Sumner et al., 2000). Several of the major immunoreactive proteins identified and molecularly characterized are serine-rich glycoproteins that are secreted. Many of these glycoproteins have tandem repeats; however, one has numerous eukaryote-like ankyrin domains (Doyle et al., 2006; McBride et al., 2003; McBride et al., 2000; Nethery et al., 2005; Singu et al., 2005; Yu et al., 2000).

Numerous proteins have been identified in *E. canis* (n=12) and *E. ruminantium* (n=31) that contain tandem repeats. Notably, three immunoreactive proteins with tandem repeats have been identified and molecularly characterized in *E. chaffeensis* (gp120, gp47, and VLPT) as well as two orthologs in *E. canis* (gp140 and gp36, respectively). The ortholog of *E. chaffeensis* vlpt gene has not been identified in *E. canis*, and it has been reported that this gene is not present in other ehrlichial genomes (Hotopp et al., 2006). Extensive variability in the number and/or sequence of tandem repeats in the *E. chaffeensis* immunoreactive proteins (gp120, gp47 and VLPT) as well as *E. canis* gp36 is well documented (Chen et al., 1997; Doyle et al., 2006; Sumner et al., 1999). The presence of tandem repeats in both coding and noncoding regions of the genome has been linked to an active process of expansion and reduction of ehrlichial genomes (Frutos et al., 2006) and is considered a major source of genomic change and instability (Bzymek and Lovett, 2001).

Although the *E. chaffeensis* VLPT is immunoreactive, little is known regarding its cellular location, function and role in development of protective immunity. The *E. chaffeensis* vlpt gene exhibits variations in the number of 90-bp tandem repeats (3 to 5) and has been utilized as a molecular diagnostic target and for differentiation of isolates (Sumner et al., 1999; Yabsley et al., 2003). The VLPT of *E. chaffeensis* Arkansas is a 198 amino acid protein that has four repeats (30 amino acids) and has a molecular mass approximately double that predicted by its amino acid sequence (Sumner et al., 1999). *E. chaffeensis* VLPT protein appears to have posttranslational modification consistent with other described ehrlichial glycoproteins, but the presence of carbohydrate on VLPT has not been demonstrated.

The present invention fulfills a need in the art by providing novel methods and compositions concerning erhlichial infections in mammals, and in particular provides methods and compositions in an *E. canis* ortholog of *E. chaffeensis* VLPT.

SUMMARY OF THE INVENTION

Canine monocytic ehrlichiosis is a globally-distributed tick-borne disease caused by the obligate intracellular bacterium *E. canis* and is a useful model for understanding immune and pathogenic mechanisms of *E. chaffeensis*, the causative agent of human monocytotropic ehrlichiosis. In general, the present invention concerns ehrlichial immunogenic compositions, including, for example, immunoprotective antigens as vaccines for ehrlichial diseases, such as subunit vaccines, for example. The immunogenic composition may be employed for any mammal, including, for example, humans, dogs, cats, horses, pigs, goats, or sheep.

In certain aspects of the invention, there is identification and characterization of highly conserved 19 kDa major immunoreactive glycoprotein (gp19) in *E. canis*, the ortholog of the *E. chaffeensis* VLPT. The *E. canis* gp19 lacks tandem repeats present in VLPT of *E. chaffeensis*, but the two proteins exhibit substantial amino acid similarity (59%) in a cysteine/tyrosine-rich carboxyl-terminal region, and both genes have the same relative chromosomal location. Carbohydrate was detected on the recombinant gp19 and a single major antibody epitope was mapped to a serine/threonine/glutamate (STE)-rich patch. This epitope was sensitive to periodate treatment, and an exemplary recombinant protein was substantially more immunoreactive than an exemplary synthetic peptide, demonstrating a role for carbohydrate as an immunodeterminant, in certain embodiments of the invention. The gp19 was found on both reticulate and dense cored cells and was also present in the extracellular matrix and associated with the morula membrane, indicating that the protein is secreted.

In specific aspects of the present invention, there are ehrlichial gp19 polypeptide compositions (or polynucleotide compositions that encode all or part of them) with one or more of the following characteristics: 1) comprises one or more carbohydrate moities, which in specific embodiments comprises part of an epitope determinant; 2) comprises one or more moieties, such as an epitope, that are immunogenically species-specific; 3) is released extracellularly, such as by secretion; 4) comprises major B cell epitopes; 5) is surface-exposed; 6) is associated with the infectious dense-cored forms of Ehrlichiae, such as on the surface, for example; and 7) is associated with morula membranes (Ehrlichiae organisms form microcolonies inside cellular vacuoles (morulae) that harbor many individual Ehrlichiae) comprising dense-cored forms. In further aspects, recombinant polypeptide compositions of the present invention are able to be glycosylated in a cell to which it is not native, such as an *E. coli* cell, for example. The recombinant polypeptide may then be employed as an immunogenic composition, including, for example, a vaccine.

In particular embodiments of the invention, there are *E. canis* gp19 immunogenic compositions that comprise an amino acid sequence that is immunogenic, and in further particular embodiments, the immunogenicity is characterized by being at least part of an epitope. In further embodiments, the amino acid sequence comprises at least part of a vaccine composition against an ehrlichial organism, such as *E. canis*. In specific embodiments, the amino acid sequence comprises serines, threonines, or, optionally, alanine, proline, valine, and/or glutamic acid; in additional embodiments, the amino acid sequence is glycosylated. In further specific embodiments, the amino acid sequence comprises part or all of the following exemplary sequence: HFTGPTSFEVNLSEEEKMELQEVS (SEQ ID NO:13). In certain embodiments, the epitope comprises additional amino acids on the C-terminus, such as those that are immediately C-terminal to the sequence of SEQ ID NO:13 in the naturally-occurring gp19, such as is exemplified by SEQ ID NO:17 or SEQ ID NO:19. In particular embodiments, there may be 1, 2, 3, 4, 5, 6, 7, 8, 9, 10, or more additional amino acids on the C-terminus of SEQ ID NO:13. In additional embodiments, the amino acid sequence is comprised in a pharmaceutically acceptable excipient, which in some aspects of the invention comprises an adjuvant. In certain aspects of the invention, there is a polynucleotide comprising SEQ ID NO:20 (CATTTTACTGGTCCTACTAGTTTTGAAGTTAATCTTTCTGAAGAAGAAAAAA TGGAGTTACAAGAAGTATCT) that encodes the peptide sequence of SEQ ID NO:13.

*E. canis* sequences may be identified following sequencing of gp19 in other strains; additional *E. canis* strains are tested, including North Carolina (Jake), Oklahoma, North Carolina (Demon), North Carolina (DJ), North Carolina (Fuzzy), Louisiana, Florida, Sao Paulo, Cameroon, Israeli, and Mexico. In additional embodiments, the amino acid sequence is comprised in a pharmaceutically acceptable excipient, which in some aspects of the invention comprises an adjuvant.

In certain embodiments of the present invention, there are immunogenic gp19 *E. canis* compositions, and particular sequences of the gp19 compositions may impart its immunogenicity; for example, a region of the gp19 composition may comprise an epitope. In particular embodiments, one or more epitopes on a gp19 composition are located in the C-terminus or in the N-terminus of a gp19 polypeptide. In specific aspects, the C-terminus comprises the last 60 amino acids of SEQ ID NO:17 or SEQ ID NO:19, for example. In additional aspects of the invention, the C-terminus comprises the last 60 amino acids of SEQ ID NO:17 or SEQ ID NO:19, and in particular aspects the C-terminus comprises the last 55, the last 50, the last 45, the last 40, the last 35, the last 30, the last 25, the last 20, the last 15, the last 10, or the last 5 amino acids of SEQ ID NO:17 or SEQ ID NO:19. In additional aspects of the invention, the C-terminus comprises no more than the last 60 amino acids of SEQ ID NO:17 or SEQ ID NO:19, and in particular aspects the C-terminus comprises no more than the last 55, the last 50, the last 45, the last 40, the last 35, the last 30, the last 25, the last 20, the last 15, the last 10, or the last 5 amino acids of SEQ ID NO:17 or SEQ ID NO:19. In other specific aspects, the N-terminus comprises the first 74 amino acids of SEQ ID NO:17 or SEQ ID NO:19. In further aspects of the invention, the N-terminus comprises the first 74 amino acids of SEQ ID NO:17 or SEQ ID NO:19, and in particular aspects the N-terminus comprises the first 70, the first 65, the first 60, the first 55, the first 50, the first 45, the first 40, the first 35, the first 30, the first 25, the first 20, the first 15, the first 10, or the first 5 amino acids of SEQ ID NO:17 or SEQ ID NO:19. In further aspects of the invention, the N-terminus comprises no more than the first 74 amino acids of SEQ ID NO:17 or SEQ ID NO:19, and in particular aspects the N-terminus comprises no more than the first 70, the first 65, the first 60, the first 55, the first 50, the first 45, the first 40, the first 35, the first 30, the first 25, the first 20, the first 15, the first 10, or the first 5 amino acids of SEQ ID NO:17 or SEQ ID NO:19.

In some aspects of the invention, multiple different *E. canis* strains comprise immunogenic gp19 compositions, and there is significant sequence identity among the strains in regions of the gp19 compositions that comprise the epitope (such as greater than about 80%, 85%, 90%, 95%, or 98%, for example). However, in some embodiments, there may be significant sequence identity among the strains in regions of the gp19 compositions that do not comprise the epitope. In particular aspects of the invention, there is a gp19 composition that is immunogenic for more than one strain of *E. canis*, including, for example, North Carolina (Jake), Oklahoma, North Carolina (Demon), North Carolina (DJ), North Carolina (Fuzzy), Louisiana, Florida, and in particular aspects the epitope of the other strains is SEQ ID NO:13, although other epitopes may also be identified. In embodiments wherein an alternative gp19 *E. canis* epitope to SEQ ID NO:13 is identified, there may be provided an immunogenic composition comprising a mixture of gp19 *E. canis* epitopes, such as a mixture including SEQ ID NO:13, for example.

In certain embodiments of the invention, immunogenic compositions of *E. canis* comprise one or more carbohydrate moieties. In particular aspects, the carbohydrate moieties facilitate the immunogenic nature of the composition. In specific embodiments, the carbohydrate moiety is required for immunogenicity, whereas in alternative embodiments the carbohydrate moiety enhances immunogenicity. The carbohydrate moiety may be of any kind, so long as it is suitable to allow or enhance immunogenicity. The identity of a carbohydrate moiety may be determined by any suitable means in the art, although in particular aspects an enzyme that cleaves particular carbohydrates from polypeptides or peptides, followed by analysis of the cleaved carbohydrate, for example with mass spectroscopy, may be utilized. In other means, the carbohydrate is removed and assayed with a variety of lectins, which are known to bind specific sugars. In specific embodiments, the carbohydrate comprises glucose, galactose and/or xylose. In specific embodiments of the invention, one or more carbohydrate moieties on the glycoprotein are identified by suitable method(s) in the art, for example gas chromatography/mass spectrometry.

In an embodiment of the invention, there is an immunogenic gp19 *E. canis* glycoprotein. In an additional embodiment of the invention, there is an *E. canis* composition comprising SEQ ID NO:13. In specific aspects of the invention, the composition further comprises a pharmaceutically acceptable excipient. The composition may be further defined as comprising one or more carbohydrate moieties, as comprising part or all of an epitope, and/or as a vaccine, such as a subunit vaccine.

In another embodiment of the invention, there is an *E. canis* composition comprising a polypeptide encoded by at least part of the polynucleotide of SEQ ID NO:16 or SEQ ID NO:18 and/or an *E. canis* composition comprising a polypeptide of SEQ ID NO:17 or SEQ ID NO:19. In one embodiment of the invention, there is an isolated composition comprising an *Ehrlichia* gp19 glycoprotein, comprising: (a) a sequence selected from the group consisting of SEQ ID NO:13, SEQ ID NO:17, or SEQ ID NO:19; or (b) a sequence that is at least about 70% identical to one or more sequences in (a). The composition may be further defined as a sequence that is at least about 75%, about 80%, about 85%, about 90%, or about 95% identical to one or more sequences in (a). The composition may also be further defined as being comprised in a pharmaceutically acceptable excipient, as comprising one or more carbohydrate moieties, and/or as being comprised in a pharmaceutical composition suitable as a vaccine.

In a specific embodiment, there is an isolated polynucleotide that encodes SEQ ID NO:17, an isolated polynucleotide that encodes SEQ ID NO:19, an isolated polynucleotide that encodes SEQ ID NO:13, or a mixture thereof.

In particular embodiments, there is an isolated polynucleotide, comprising: a) a polynucleotide that encodes SEQ ID NO:17; or b) a polynucleotide that is at least about 90% identical to the polynucleotide of a) and that encodes an immunoreactive *E. canis* gp19 polypeptide. In a specific embodiment, the polynucleotide is further defined as SEQ ID NO:16.

In particular embodiments, there is an isolated polynucleotide, comprising: a) a polynucleotide that encodes SEQ ID NO:19; or b) a polynucleotide that is at least about 90% identical to the polynucleotide of a) and that encodes an immunoreactive *E. canis* gp19 polypeptide. In a specific embodiment, the polynucleotide is further defined as SEQ ID NO:18.

In a further embodiment of the invention, there is an isolated polynucleotide, comprising: a) a polynucleotide that encodes SEQ ID NO:17; or b) a polynucleotide that is at least about 90% identical to the polynucleotide of a) and that encodes an immunoreactive *E. canis* gp19 polypeptide. In a specific embodiment, the polynucleotide is further defined as SEQ ID NO:16. In additional aspects of the invention, there is an isolated polynucleotide, comprising: a) a polynucleotide that encodes SEQ ID NO:19; or b) a polynucleotide that is at least about 90% identical to the polynucleotide of a) and that encodes an immunoreactive *E. canis* gp19 polypeptide. In a specific embodiment the polynucleotide is further defined as SEQ ID NO:18.

In an additional embodiment of the invention, there is an isolated polypeptide, comprising: a) SEQ ID NO:17 and/or SEQ ID NO:19; or b) a gp19 polypeptide that is at least about 70% identical to SEQ ID NO:17 and/or SEQ ID NO:19 and that comprises immunogenic activity. In a specific embodiment, the polypeptide is comprised in a pharmaceutically acceptable excipient, and/or it may be further defined as being comprised in a pharmaceutical composition suitable as a vaccine.

In certain aspects of the invention, there are polynucleotides that are amplifiable by one or more of the exemplary primers of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:14, or SEQ ID NO:15.

In specific aspects of the invention, there is a polynucleotide that encodes a polypeptide comprising SEQ ID NO:13, and in specific embodiments the polynucleotide comprises SEQ ID NO:20. In other aspects of the invention, there is a polynucleotide that encodes a polypeptide comprising SEQ ID NO:17 and/or SEQ ID NO:19.

In another aspect of the invention, there are isolated antibodies that bind one or more polypeptides of the invention. Antibodies may be monoclonal, polyclonal, or antibody fragments, for example. In particular embodiments, the antibody binds selectively to an epitope of gp19, for example one that comprises SEQ ID NO:13. In specific embodiments, the antibody may be referred to as immunologically reacting with one or more polypeptides of the invention.

In further aspects, there is a peptide or polypeptide that comprises SEQ ID NO:13 or has a sequence that has 1, 2, 3, 4, 5, 6, 7, 8, 9, 10, 11, 12, 13, 14, 15, 16, 17, 18, 19, 20, 21, 22, or 23 substitutions relative to SEQ ID NO:13, and in specific aspects the substitutions are conservative substitutions.

In an additional embodiment of the invention, there is a method of providing resistance to *E. canis* infection, comprising the step of delivering a therapeutically effective amount of a composition of the invention, such as a gp19 antibody, polypeptide, and/or polynucleotide, to the individual.

In another embodiment, there is a method of inducing an immune response in an individual, comprising the step of delivering to the individual a therapeutically effective amount of a gp19 polypeptide of the invention. In an additional embodiment of the present invention, there is a method of inhibiting or preventing *E. canis* infection in a subject comprising the steps of: identifying a subject prior to exposure or suspected of being exposed to or infected with *E. canis*; and administering a polypeptide, antibody, and/or polynucleotide of the invention in an amount effective to inhibit *E. canis* infection.

In some aspects of the invention the composition may be encoded by a polynucleotide comprising: (a) a polynucleotide selected from the group consisting of SEQ ID NO:16, SEQ ID NO:18 and SEQ ID NO:20; or (b) a polynucleotide that is at least about 70% identical to a polynucleotide of (a) and encodes an immunoreactive *E. canis* gp19 polypeptide; or (c) a polynucleotide that hybridizes to one or more polynucleotides of (a) or (b) under stringent conditions. In specific embodiments of the invention, the polynucleotide of (c) is at least about 70% identical, at least about 75% identical, at least about 80% identical, at least about 85% identical, at least about 90% identical, or at least about 95% identical to a polynucleotide of (a) or (b) and encodes an immunoreactive *E. canis* gp19 polypeptide.

Polynucleotides of the invention may be comprised in a vector, such as a viral vector or a non-viral vector, wherein the viral vector may be an adenoviral vector, a retroviral vector, a lentiviral vector, an adeno-associated vector, a herpes virus vector, or a vaccinia virus vector and wherein the non-viral vector may be a plasmid. In further aspects of the invention, the vector comprise a promoter operably linked to the polynucleotide wherein the promoter is operable in a prokaryote, a eukaryote, or both. The polynucleotide of the invention may be comprised in a liposome and/or comprised in a pharmaceutically acceptable excipient.

In certain aspects of the invention, there is an isolated antibody that reacts immunologically to a polypeptide of the invention, and the antibody may be a monoclonal antibody, may be comprised in polyclonal antisera, or may be an antibody fragment, for example.

In other embodiments of the invention, there is a method of inducing an immune response in an individual, comprising the step of delivering to the individual a therapeutically effective amount of a composition of the invention, such as a polypeptide, antibody and/or polynucleotide.

In additional embodiments of the invention, there is a method of inhibiting E. canis infection in a subject comprising the steps of: identifying a subject prior to exposure or suspected of being exposed to or infected with E. canis; and administering the polypeptide of the invention in an amount effective to inhibit E. canis infection. In further embodiments of the invention, there is a method of identifying an E. canis infection in an individual, comprising the step of assaying a sample from the individual for an antibody, polypeptide, and/or polynucleotide of the invention.

In one embodiment of the invention, there is a pharmaceutical composition, comprising one or more of the following: (a) an isolated polypeptide comprising SEQ ID NO:17 or SEQ ID NO:19; (b) an isolated polypeptide that is at least 70% identical to a polypeptide of (a); (c) an isolated polypeptide comprising SEQ ID NO:13; or (d) an isolated polypeptide that is at least 70% identical to SEQ ID NO:13, wherein said polypeptide is dispersed in a pharmaceutically acceptable diluent. In specific embodiments, (b) is further defined as a polypeptide that is at least 75% identical to a polypeptide of (a); as a polypeptide that is at least 80% identical to a polypeptide of (a); as a polypeptide that is at least 85% identical to a polypeptide of (a); as a polypeptide that is at least 90% identical to a polypeptide of (a); or as a polypeptide that is at least 95% identical to a polypeptide of (a). The pharmaceutical composition may further defined as a vaccine composition.

In specific embodiments, a polypeptide of a pharmaceutical composition is further defined as comprising one or more carbohydrate moieties. In certain aspects, the polypeptide of comprises SEQ ID NO:17 or the polypeptide comprises SEQ ID NO:19.

In specific aspects of the invention, a polypeptide is further defined as being from 24 to 30 amino acids in length, from 24 to 35 amino acids in length, from 24 to 40 amino acids in length, from 24 to 45 amino acids in length, from 24 to 50 amino acids in length, from 24 to 55 amino acids in length, from 24 to 60 amino acids in length, from 24 to 65 amino acids in length, from 24 to 70 amino acids in length, from 24 to 75 amino acids in length, from 24 to 80 amino acids in length, from 24 to 85 amino acids in length, from 24 to 90 amino acids in length, from 24 to 95 amino acids in length, or from 24 to 100 amino acids in length, for example.

Variants of polypeptides comprising SEQ ID NO:13 may be defined as being at least 80% identical to SEQ ID NO:13; as being at least 85% identical to SEQ ID NO:13; as being at least 90% identical to SEQ ID NO:13; or as being at least 95% identical to SEQ ID NO:13.

In additional embodiments of the invention, there is a pharmaceutical composition comprising an isolated polypeptide encoded by an isolated nucleic acid molecule, said nucleic acid molecule comprising: (a) a polynucleotide comprising SEQ ID NO:16 or SEQ ID NO:18; or (b) a polynucleotide that is capable of hybridizing under stringent conditions to the polynucleotide of (a); wherein the polypeptide has at least 70% identity to SEQ ID NO:17 or SEQ ID NO:19 and wherein the polypeptide is dispersed in a pharmaceutically acceptable diluent. The polypeptide may be at least 75% identical to SEQ ID NO:17 or SEQ ID NO:19; at least 80% identical to SEQ ID NO:17 or SEQ ID NO:19; at least 85% identical to SEQ ID NO:17 or SEQ ID NO:19; at least 90% identical to SEQ ID NO:17 or SEQ ID NO:19; or at least 95% identical to SEQ ID NO:17 or SEQ ID NO:19.

The invention in certain aspects concerns a composition, comprising (a) an isolated polypeptide or peptide comprising more than 15, such as more than 20, such as more then 23, but no more than 130 contiguous amino acids of SEQ ID NO:17 or SEQ ID NO:19; or (b) a polypeptide or peptide that is about 70%, about 75%, about 80%, about 85%, about 90%, or about 95% identical to a sequence that is no more than 130 contiguous amino acids of SEQ ID NO:17 or SEQ ID NO:19.

In additional aspects, there is a polypeptide further defined as being encoded by a polynucleotide that is no more than 75%, 80%, 85%, 90%, 95%, 97%, or 99% identical to SEQ ID NO:16 or SEQ ID NO:18.

In an additional embodiment, there is a composition comprising: (a) a peptide having SEQ ID NO:13; or (b) a variant of the peptide of (a), wherein the variant is at least 75% identical to SEQ ID NO:13, wherein the composition is capable of eliciting an immune reaction in an individual. In a specific embodiment, there is a peptide is from 24 to 50 amino acids in length. In a specific embodiment, there is a variant is further defined as being at least 80%, at least 85%, at least 90%, or at least 95% identical to SEQ ID NO:13.

A composition of the invention may be defined as having activity that provides immunity against Ehrlichia canis for an individual. A composition of the invention may be defined as having activity that induces an immune reaction against Ehrlichia canis for an individual. Compositions of the invention include any polypeptide, peptide, polynucleotide, and/or antibody provided herein.

In another embodiment of the invention, there is an isolated nucleic acid molecule, comprising: (a) a polynucleotide comprising SEQ ID NO:16 or SEQ ID NO:18; or (b) a polynucleotide that is capable of hybridizing under stringent conditions to the polynucleotide of (a) and that encodes a polypeptide having at least 70% identity to SEQ ID NO:17 or SEQ ID NO:19, wherein said nucleic acid molecule is operably linked to a heterologous promoter, such as a promoter that is active in a eukaryotic cell or that is active in a prokaryotic cell. In a specific embodiment, the nucleic acid molecule is further defined as the polynucleotide comprising SEQ ID NO:16 or as the polynucleotide comprising SEQ ID NO:18. The polynucleotide of (b) may be further defined as a polynucleotide that encodes a polypeptide that is at least 75% identical to SEQ ID NO:17 or SEQ ID NO:19; that is at least 80% identical to SEQ ID NO:17 or SEQ ID NO:19; that is at least 85% identical to SEQ ID NO:17 or SEQ ID NO:19; that is at least 90% identical to SEQ ID NO:17 or SEQ ID NO:19; or that is at least 95% identical to SEQ ID NO:17 or SEQ ID NO:19.

In an additional embodiment of the invention, there is an isolated DNA, comprising: (a) sequence that is no less than 75% but no more than 98% identical to SEQ ID NO:16 or SEQ ID NO:18; or (b) sequence that is complementary to the sequence in (a). In specific embodiments, (a) is further defined as a sequence that is no less than 80% but no more than 98% identical to SEQ ID NO:16 or SEQ ID NO:18; as a sequence that is no less than 85% but no more than 98% identical to SEQ ID NO:16 or SEQ ID NO:18; as a sequence that is no less than 90% but no more than 98% identical to SEQ ID NO:16 or SEQ ID NO:18; as a sequence that is no less than 95% but no more than 98% identical to SEQ ID NO:16 or SEQ ID NO:18; as a sequence that is no less than 80% but no more than 95% identical to SEQ ID NO:16 or SEQ ID NO:18; as a sequence that is no less than 80% but no more than 90% identical to SEQ ID NO:16 or SEQ ID NO:18; or as a sequence that is no less than 80% but no more than 85% identical to SEQ ID NO:16 or SEQ ID NO:18.

Nucleic acid molecules may be further defined as being comprised in a vector, such as a viral vector or a non-viral vector, wherein the viral vector may comprise an adenoviral vector, a retroviral vector, or an adeno-associated viral vector. The nucleic acid molecule may be comprised in a liposome.

In specific embodiments, there is an isolated antibody that immunologically reacts with one or more of the amino acid sequences selected from the group consisting of SEQ ID NO:13, SEQ ID NO:17, and SEQ ID NO:19. In further specific embodiments, the antibody is a monoclonal antibody, is comprised in polyclonal antisera, or is an antibody fragment.

In an additional embodiment, there is a method of producing a polypeptide, comprising: providing a host cell comprising a polynucleotide of the invention and culturing the cell under conditions suitable for the host cell to express the polynucleotide to produce the encoded polypeptide. The method may further comprise isolating the polypeptide.

In another embodiment, there is a method of producing a polynucleotide, comprising: hybridizing SEQ ID NO:16 or SEQ ID NO:18 to genomic DNA under stringent conditions; and isolating the polynucleotide detected with SEQ ID NO:16 or SEQ ID NO:18. In a specific embodiment, there is an isolated DNA prepared according to the method.

In an additional embodiment of the invention, there is a method of inducing an immune response in an individual, comprising the step of delivering to the individual a therapeutically effective amount of a composition of the invention.

In a further embodiment of the invention, there is a method of inhibiting *E. canis* infection in a subject, comprising the step of administering to the subject prior to exposure or suspected of being exposed to or infected with *E. canis*, an effective amount of a composition of the invention.

In an additional embodiment of the invention, there is a method of identifying an *E. canis* infection in an individual, comprising the step of assaying a sample from the individual for one or both of the following: (a) a polypeptide of SEQ ID NO:17, SEQ ID NO:19, or both; or (b) an antibody that immunologically reacts with an amino acid sequence selected from the group consisting of SEQ ID NO:13, SEQ ID NO:17, and SEQ ID NO:19. In a specific embodiment of this method, the polypeptide of (a) is SEQ ID NO:17. In a specific embodiment of this method, the polypeptide of (a) is SEQ ID NO:19. In a specific embodiment of this method, the polypeptide of (a) is a mixture of SEQ ID NO:17 and SEQ ID NO:19. In specific embodiments, the antibody of (b) immunologically reacts with an amino acid sequence of SEQ ID NO:13, SEQ ID NO:17, or SEQ ID NO:19. In specific aspects, assaying a sample for an antibody is further defined as assaying for an antibody by ELISA, such as by allowing assaying for one or more *E. canis* antibodies other then the antibody of (b). The other *E. canis* antibodies are selected from the group consisting of antibodies for gp36, gp19, gp28/30, and gp200.

In an embodiment of the invention, there is a kit, comprising one or more of the following compositions: (a) an isolated polypeptide comprising SEQ ID NO:17 or SEQ ID NO:19; (b) an isolated polypeptide that is at least 70% identical to a polypeptide of (a); (c) an isolated polypeptide comprising SEQ ID NO:13; (d) an isolated polypeptide that is at least 70% identical to SEQ ID NO:13; (e) a polynucleotide comprising SEQ ID NO:16 or SEQ ID NO:18; (f) a polynucleotide that is capable of hybridizing under stringent conditions to the polynucleotide of (a) and that encodes a polypeptide having at least 70% identity to SEQ ID NO:17 or SEQ ID NO:19; or (g) an isolated antibody that immunologically reacts with one or more of the amino acid sequences selected from the group consisting of SEQ ID NO:13, SEQ ID NO:17, and SEQ ID NO:19. In a specific embodiment, the kit is further defined as comprising two or more of the compositions.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features that are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

Figure 5:
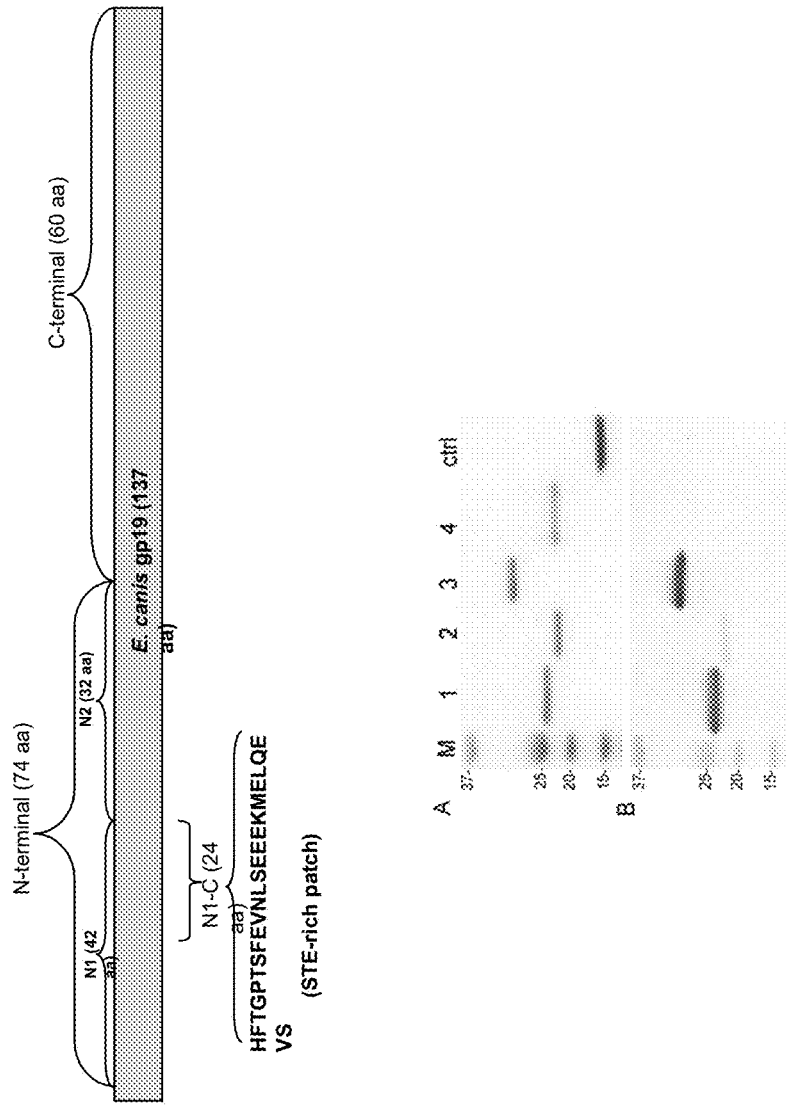

FIG. 5 provides (Top) schematic of *E. canis* recombinant gp19 fragments including the epitope-comprising region N1-C. Also shown there is the STE-rich patch N1-C (SEQ ID NO:13) (Panel A) SDS-PAGE of *E. canis* recombinant gp19 fragments (N1, lane 1; N2, lane 2; N-terminal, lane 3; and C-terminal, lane 4; and thioredoxin control) and corresponding Western immunoblot probed with anti-*E. canis* dog serum (Panel B).

Figure 6:
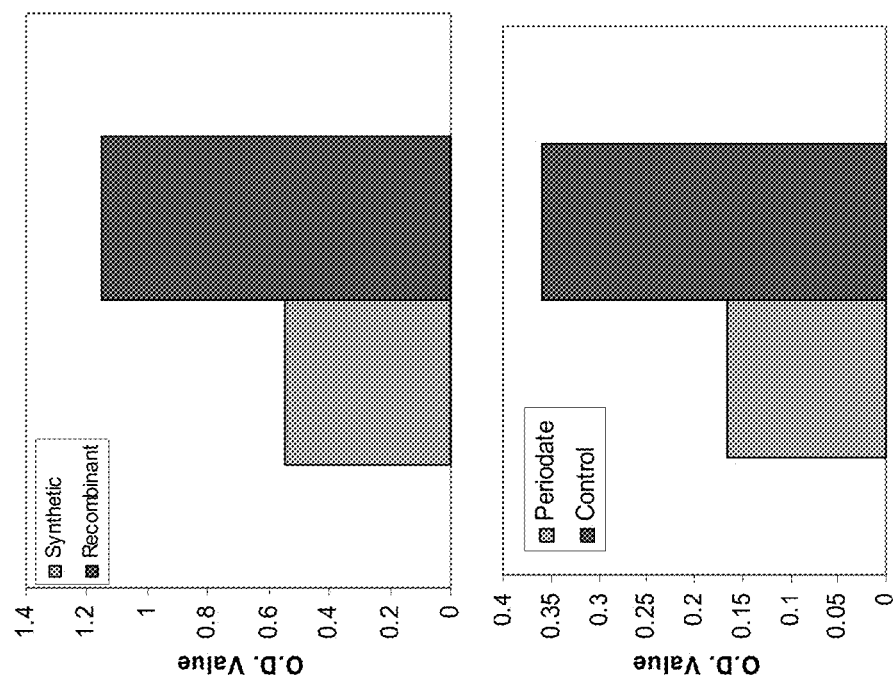

FIG. 6 shows immunoreactivity of recombinant gp19 (N1-C epitope; glycosylated) with canine anti-*E. canis* serum compared to the synthetic peptide (aglycosylated) by ELISA (top). Immunoreactivity of *E. canis* gp19 (N1-C epitope) with anti-*E. canis* dog serum after treatment with periodate as determined by ELISA (bottom).

Figure 7:
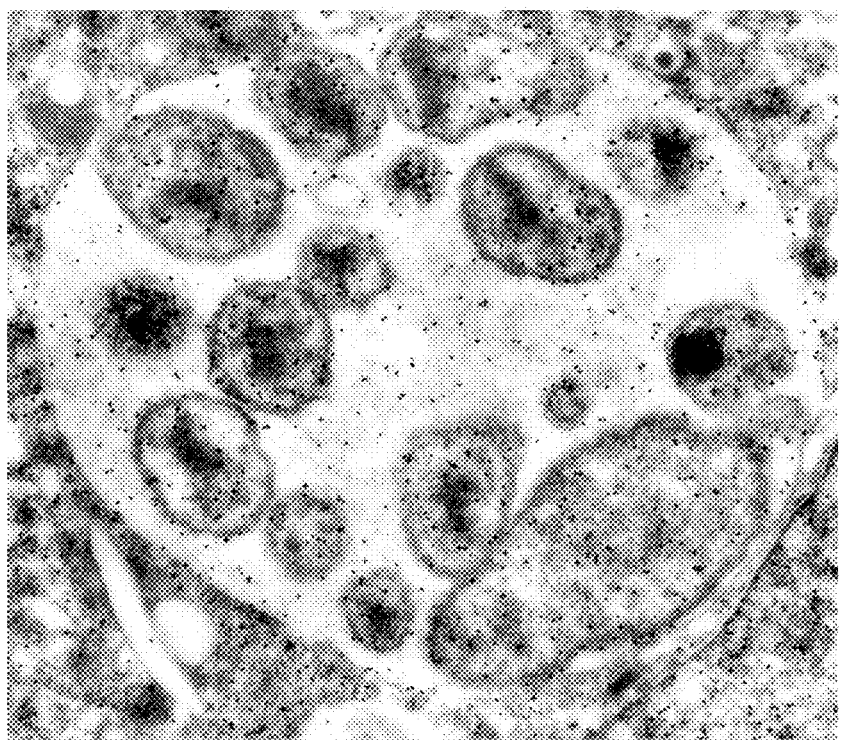

FIG. 7 demonstrates an exemplary immunogold-labeled electron photomicrograph of *E. canis* gp19 localization in a morula containing both reticulate and dense-cored Ehrlichiae.

FIGS. 8A-C show an exemplary confocal immunofluorescent photomicrograph of *E. canis* gp19 expression. *E. canis* infected cells were dually stained with anti-*E. canis* gp19 (A) and with anti-ehrlichial Dsb (B) and merged images (C).

FIGS. 9A-C show demonstration of the kinetics of IgG antibody responses to *E. canis* in three experimentally infected dogs (A=Dog 33; B=Dog 34; and C=Dog 44) to five recombinant proteins gp36 (◇), gp19 (□), p28 (Δ), gp200N (x), gp200C (○) and a thioredoxin control (+) on days 0, 7, 14, 21, 28, 35, and 42 post inoculation as determined by Western immunoblot (left) and corresponding ELISA (right).

DETAILED DESCRIPTION OF THE INVENTION

I. Definitions

In keeping with long-standing patent law convention, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein.

The term "carbohydrate" as used herein refers to a composition comprised of carbon, hydrogen, and oxygen, particularly in the ratio of 2H:1C:1O. The term includes sugars, starches, and celluloses, for example.

The term "epitope" as used herein refers to a site of a composition to which a specific antibody binds.

The term "glycan," which may also be referred to as a "polysaccharide," as used herein refers to a carbohydrate that can be decomposed by hydrolysis into two or more monosaccharides. In other words, it may be referred to as a chain of simple sugars (aldehyde or ketone derivatives of a polyhydric alcohol).

The term "identity" as known in the art, refers to a relationship between the sequences of two or more polypeptide molecules or two or more nucleic acid molecules, as determined by comparing the sequences. In the art, "identity" also means the degree of sequence relatedness between nucleic acid molecules or between polypeptides, as the case may be, as determined by the number of matches between strings of two or more nucleotide residues or two or more amino acid residues. "Identity" measures the percent of identical matches between the smaller of two or more sequences with gap alignments (if any) addressed by a particular mathematical model or computer program (i.e., "algorithms").

The term "immunogenic" as used herein refers to a composition that is able to provoke an immune response against it.

The term "immune response" as used herein refers to the reaction of the immune system to the presence of an antigen by making antibodies to the antigen. In further specific embodiments, immunity to the antigen may be developed on a cellular level, by the body as a whole, hypersensitivity to the antigen may be developed, and/or tolerance may be developed, such as from subsequent challenge. In specific embodiments, an immune response entails lymphocytes identifying an antigenic molecule as foreign and inducing the formation of antibodies and lymphocytes capable of reacting with it and rendering it less harmful.

The term "immunoreactive" as used herein refers to a composition being reactive with antibodies from the sera of an individual. In specific embodiments, a composition is immunoreactive if an antibody recognizes it, such as by binding to it and/or immunologically reacting with it.

The term "mucin" as used herein refers to one or more highly glycosylated glycoproteins with N-acetylgalactosamine (GalNAc.)

The term "ortholog" as used herein refers to a polynucleotide from one species that corresponds to a polynucleotide in another species; the two polynucleotides are related through a common ancestral species (a homologous polynucleotide). However, the polynucleotide from one species has evolved to become different from the polynucleotide of the other species.

The term "similarity" is a related concept, but in contrast to "identity", refers to a sequence relationship that includes both identical matches and conservative substitution matches. If two polypeptide sequences have, for example, {fraction (10/20)} identical amino acids, and the remainder are all non-conservative substitutions, then the percent identity and similarity would both be 50%. If, in the same example, there are 5 more positions where there are conservative substitutions, then the percent identity remains 50%, but the percent similarity would be 75% ({fraction (15/20)}). Therefore, in cases where there are conservative substitutions, the degree of similarity between two polypeptides will be higher than the percent identity between those two polypeptides.

The term "subunit vaccine" as used herein refers to a vaccine wherein a polypeptide or fragment thereof is employed, as opposed to an entire organism.

The term "vaccine" as used herein refers to a composition that provides immunity to an individual upon challenge.

The term "virulence factor" as used herein refers to one or more gene products that enable a microorganism to establish itself on or within a particular host species and enhance its pathogenicity. Exemplary virulence factors include, for example, cell surface proteins that mediate bacterial attachment, cell surface carbohydrates and proteins that protect a bacterium, bacterial toxins, and hydrolytic enzymes that may contribute to the pathogenicity of the bacterium.

The practice of the present invention will employ, unless otherwise indicated, conventional techniques of molecular biology, microbiology, recombinant DNA, and so forth which are within the skill of the art. Such techniques are explained fully in the literature. See e.g., Sambrook, Fritsch, and Maniatis, MOLECULAR CLONING: A LABORATORY MANUAL, Second Edition (1989), OLIGONUCLEOTIDE SYNTHESIS (M. J. Gait Ed., 1984), ANIMAL CELL CULTURE (R. I. Freshney, Ed., 1987), the series METHODS IN ENZYMOLOGY (Academic Press, Inc.); GENE TRANSFER VECTORS FOR MAMMALIAN CELLS (J. M. Miller and M. P. Calos eds. 1987), HANDBOOK OF EXPERIMENTAL IMMUNOLOGY, (D. M. Weir and C. C. Blackwell, Eds.), CURRENT PROTOCOLS IN MOLECULAR BIOLOGY (F. M. Ausubel, R. Brent, R. E. Kingston, D. D. Moore, J. G. Siedman, J. A. Smith, and K. Struhl, eds., 1987), CURRENT PROTOCOLS IN IMMUNOLOGY (J. E. coligan, A. M. Kruisbeek, D. H. Margulies, E. M. Shevach and W. Strober, eds., 1991); ANNUAL REVIEW OF IMMUNOLOGY; as well as monographs in journals such as ADVANCES IN IMMUNOLOGY. All patents, patent applications, and publications mentioned herein, both supra and infra, are hereby incorporated herein by reference.

II. Embodiments of the Present Invention

The present invention concerns compositions and methods related to *Ehrlichia* spp. proteins and the polynucleotides that encode them. In particular aspects of the invention, there are differentially-expressed and secreted major immunoreactive protein orthologs of *E. canis* and *E. chaffeensis* that elicit early antibody responses to epitopes on glycosylated tandem repeats. Specifically, the present invention concerns one or more glycoproteins from *Ehrlichia* spp., in specific embodiments. In further embodiments, the present invention relates to a glycoprotein from *Ehrlichia* spp. that is a gp19 protein. In additional embodiments, the gp19 protein is from *E. canis*.

*Ehrlichia canis* has a small subset of major immunoreactive proteins that includes a 19-kDa protein that elicits an early ehrlichial specific antibody response in infected dogs. The present invention concerns the identification and molecular characterization of this highly conserved 19-kDa major immunoreactive glycoprotein (gp19) ortholog of the *E. chaffeensis* variable-length PCR target (VLPT) protein. The *E. canis* gp19 has substantial carboxyl-terminal amino acid homology (59%) with *E. chaffeensis* VLPT and the same chromosomal location; however, the *E. chaffeensis* vlpt gene (594-bp) has tandem repeats that are not present in the *E. canis* gp19 (414-bp). Consistent with other ehrlichial glycoproteins, the gp19 exhibited a larger than predicted mass (~3 kDa), O-linked glycosylation sites were predicted in an amino-terminal serine/threonine/glutamate (STE)-rich patch (24 amino acids), carbohydrate was detected on the recombinant gp19, and neutral sugars glucose and xylose were detected on the recombinant amino-terminal region. The *E. canis* gp19 composition comprises five predominant amino acids, cysteine, glutamate, tyrosine, serine and threonine, concentrated in the STE-rich patch and within a carboxyl-terminal tail predominated by cysteine and tyrosine (55%). The amino-terminal STE-rich patch comprised a major species-specific antibody epitope strongly recognized by sera from an *E. canis*-infected dog. An exemplary recombinant glycopeptide epitope was substantially more reactive with antibody than an exemplary synthetic (nonglycosylated) peptide, and periodate treatment of the recombinant glycopeptide epitope reduced its immunoreactivity, indicating that carbohydrate is useful as part of an immunodeterminant. The gp19 was present on reticulate and dense cored cells and it was found extracellularly in the fibrillar matrix and associated with the morula membrane.

Some embodiments of the present invention are directed toward a method of inhibiting *E. canis* infection in a subject comprising the steps of identifying a subject prior to exposure or suspected of being exposed to or infected with *E. canis* and administering a composition comprising a 19-kDa antigen of *E. canis* in an amount effective to inhibit *E. canis* infection. The inhibition may occur through any means such as e.g., the stimulation of the subject's humoral or cellular immune responses, or by other means such as inhibiting the normal function of the 19-kDa antigen, or even competing with the antigen for interaction with some agent in the subject's body, or a combination thereof, for example.

The present invention is also directed toward a method of targeted therapy to an individual, comprising the step of administering a compound to an individual, wherein the compound has a targeting moiety and a therapeutic moiety, and wherein the targeting moiety is specific for gp19 protein. In certain aspects, the targeting moiety is an antibody specific for gp19 or ligand or ligand binding domain that binds gp19. Likewise, the therapeutic moiety may comprise a radioisotope, a toxin, a chemotherapeutic agent, an immune stimulant, a cytotoxic agent, or an antibiotic, for example.

Other embodiments of the present invention concern diagnosis of ehrlichial infection in a mammal by assaying a sample from the mammal, such as blood or serum, for example, for antibodies to a gp19 composition (for *E. canis*).

III. *E. canis* gp19 Amino Acid Compositions

The present invention regards a polypeptide or peptide comprising *E. canis* gp19. For the sake of brevity, the following section will refer to any *E. canis* gp19 amino acid compositions of the present invention, including polypeptides and peptides.

In particular embodiments, a polypeptide may be a recombinant polypeptide or it may be isolated and/or purified from nature, for example. In particular aspects, the amino acid sequence is encoded by a nucleic acid sequence. The polypeptide is useful as an antigen, in specific embodiments. In other particular embodiments, a peptide may be generated synthetically or encoded by an oligonucleotide, for example. The peptide is useful as an antigen, in specific embodiments.

The present invention is also directed towards a method of producing the recombinant polypeptide, comprising the steps of obtaining a vector that comprises an expression construct comprising a sequence encoding the amino acid sequence operatively linked to a promoter; transfecting the vector into a cell; and culturing the cell under conditions effective for expression of the expression construct. The amino acid sequence may be generated synthetically, in alternative embodiments.

By a "substantially pure protein" is meant a protein that has been separated from at least some of those components that naturally accompany it. A substantially pure immunoreactive composition may be obtained, for example, by extraction from a natural source; by expression of a recombinant nucleic acid encoding an immunoreactive composition; or by chemically synthesizing the protein, for example. Accordingly, substantially pure proteins include proteins synthesized in *E. coli*, other prokaryotes, or any other organism in which they do not naturally occur.

Thus, in certain embodiments, the present invention concerns novel compositions comprising at least one proteinaceous molecule. As used herein, a "proteinaceous molecule," "proteinaceous composition," "proteinaceous compound," "proteinaceous chain" or "proteinaceous material" generally refers, but is not limited to, a protein of greater than about 130 amino acids or the full length endogenous sequence translated from a gene; a polypeptide of greater than about 100 amino acids; and/or a peptide of from about 3 to about 100 amino acids. All the "proteinaceous" terms described above may be used interchangeably herein.

In certain embodiments the size of the at least one proteinaceous molecule may comprise, but is not limited to, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 110, about 120, about 130, or greater amino acid residues, and any range derivable therein.

As used herein, an "amino acid molecule" refers to any polypeptide, polypeptide derivative, or polypeptide mimetic as would be known to one of ordinary skill in the art. In certain embodiments, the residues of the proteinaceous molecule are sequential, without any non-amino acid molecule interrupting the sequence of amino acid molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid, including but not limited to those shown on Table 1 below.

TABLE 1

Modified and Unusual Amino Acids

| Abbr. | Amino Acid | Abbr. | Amino Acid |
|---|---|---|---|
| Aad | 2-Aminoadipic acid | EtAsn | N-Ethylasparagine |
| Baad | 3-Aminoadipic acid | Hyl | Hydroxylysine |
| Bala | β-alanine, β-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | AIle | allo-Isoleucine |
| Aib | 2-Aminoisobutyric acid | MeGly | N-Methylglycine, sarcosine |
| Baib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

In certain embodiments the proteinaceous composition comprises at least one protein, polypeptide or peptide. In further embodiments, the proteinaceous composition comprises a biocompatible protein, polypeptide or peptide. As used herein, the term "biocompatible" refers to a substance that produces no significant untoward effects when applied to, or administered to, a given organism according to the methods and amounts described herein. Such untoward or undesirable effects are those such as significant toxicity or adverse immunological reactions.

Proteinaceous compositions may be made by any technique known to those of skill in the art, including the expression of proteins, polypeptides or peptides through standard molecular biological techniques, the isolation of proteinaceous compounds from natural sources, or the chemical synthesis of proteinaceous materials, for example. The nucleotide and protein, polypeptide and peptide sequences for various genes have been previously disclosed, and may be found at computerized databases known to those of ordinary skill in the art. Two such databases are the National Center for Biotechnology Information's GenBank® and GenPept databases, for example. The coding regions for these known genes may be amplified and/or expressed using the techniques disclosed herein or as would be know to those of ordinary skill in the art. Alternatively, various commercial preparations of proteins, polypeptides and peptides are known to those of skill in the art.

In certain embodiments a proteinaceous compound may be purified. Generally, "purified" will refer to a specific or protein, polypeptide, or peptide composition that has been subjected to fractionation to remove various other proteins, polypeptides, or peptides, and which composition substantially retains its activity, as may be assessed, for example, by the protein assays, as would be known to one of ordinary skill in the art for the specific or desired protein, polypeptide or peptide. Exemplary activities that may be assessed for retention in the purified proteinaceous composition are iron-binding activity and immunoreactivity.

In specific embodiments of the present invention, a polypeptide is labeled, and any detectable label is suitable in the invention. The label may be attached to the polypeptide at the N-terminus, at the C-terminus, or in a side chain of an amino acid residue, for example. One or more labels may be employed. Exemplary labels included radioactive labels, fluorescent labels, colorimetric labels, and so forth. In specific embodiments, the label is covalently attached to the polypeptide.

IV. *E. canis* gp19 Nucleic Acid Compositions

Certain embodiments of the present invention concern an *E. canis* gp19 nucleic acid. For the sake of brevity, the following section will refer to any *E. canis* gp19 nucleic acid compositions of the present invention.

In certain aspects, a nucleic acid comprises a wild-type or a mutant nucleic acid. In particular aspects, a nucleic acid encodes for or comprises a transcribed nucleic acid. In other aspects, a nucleic acid comprises a nucleic acid segment, or a biologically functional equivalent thereof. In particular aspects, a nucleic acid encodes a protein, polypeptide, peptide.

The term "nucleic acid" is well known in the art and may be used interchangeably herein with the term "polynucleotide." A "nucleic acid" as used herein will generally refer to a molecule (i.e., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length.

These definitions generally refer to a single-stranded molecule, but in specific embodiments will also encompass an additional strand that is partially, substantially or fully complementary to the single-stranded molecule. Thus, a nucleic acid may encompass a double-stranded molecule or a triple-stranded molecule that comprises one or more complementary strand(s) or "complement(s)" of a particular sequence comprising a molecule. As used herein, a single stranded nucleic acid may be denoted by the prefix "ss," a double stranded nucleic acid by the prefix "ds," and a triple stranded nucleic acid by the prefix "ts."

A. Nucleobases

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, carboxyalkyl, amino, hydroxyl, halogen (i.e., fluoro, chloro, bromo, or iodo), thiol or alkylthiol moiety. Preferred alkyl (e.g., alkyl, caboxyalkyl, etc.) moieties comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-diemethyladenine, an azaadenines, a 8-bromoadenine, a 8-hydroxyadenine, a 6-hydroxyaminopurine, a 6-thiopurine, a 4-(6-aminohexyl/cytosine), and the like.

A nucleobase may be comprised in a nucleoside or nucleotide, using any chemical or natural synthesis method described herein or known to one of ordinary skill in the art.

B. Nucleosides

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar (Kornberg and Baker, 1992).

C. Nucleotides

As used herein, a "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

D. Nucleic Acid Analogs

A nucleic acid may comprise, or be composed entirely of, a derivative or analog of a nucleobase, a nucleobase linker moiety and/or backbone moiety that may be present in a naturally occurring nucleic acid. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art, and have been described (see for example, Scheit, 1980, incorporated herein by reference).

Additional non-limiting examples of nucleosides, nucleotides or nucleic acids comprising 5-carbon sugar and/or backbone moiety derivatives or analogs, include those in U.S. Pat. No. 5,681,947 which describes oligonucleotides comprising purine derivatives that form triple helixes with and/or prevent expression of dsDNA; U.S. Pat. Nos. 5,652,099 and 5,763,167 which describe nucleic acids incorporating fluorescent analogs of nucleosides found in DNA or RNA, particularly for use as fluorescent nucleic acids probes; U.S. Pat. No. 5,614,617 which describes oligonucleotide analogs with substitutions on pyrimidine rings that possess enhanced nuclease stability; U.S. Pat. Nos. 5,670,663, 5,872,232 and 5,859,221 which describe oligonucleotide analogs with modified 5-carbon sugars (i.e., modified 2'-deoxyfuranosyl moieties) used in nucleic acid detection; U.S. Pat. No. 5,446,137 which describes oligonucleotides comprising at least one 5-carbon sugar moiety substituted at the 4' position with a substituent other than hydrogen that can be used in hybridization assays; U.S. Pat. No. 5,886,165 which describes oligonucleotides with both deoxyribonucleotides with 3'-5' internucleotide linkages and ribonucleotides with 2'-5' internucleotide linkages; U.S. Pat. No. 5,714,606 which describes a modified internucleotide linkage wherein a 3'-position oxygen of the internucleotide linkage is replaced by a carbon to enhance the nuclease resistance of nucleic acids; U.S. Pat. No. 5,672,697 which describes oligonucleotides containing one or more 5' methylene phosphonate internucleotide linkages that enhance nuclease resistance; U.S. Pat. Nos. 5,466,786 and 5,792,847 which describe the linkage of a substituent moiety which may comprise a drug or label to the 2' carbon of an oligonucleotide to provide enhanced nuclease stability and ability to deliver drugs or detection moieties; U.S. Pat. No. 5,223,618 which describes oligonucleotide analogs with a 2 or 3 carbon backbone linkage attaching the 4' position and 3' position of adjacent 5-carbon sugar moiety to enhanced cellular uptake, resistance to nucleases and hybridization to target RNA; U.S. Pat. No. 5,470,967 which describes oligonucleotides comprising at least one sulfamate or sulfamide internucleotide linkage that are useful as nucleic acid hybridization probe; U.S. Pat. Nos. 5,378,825, 5,777,092, 5,623,070, 5,610,289 and 5,602,240 which describe oligonucleotides with three or four atom linker moeity replacing phosphodiester backbone moeity used for improved nuclease resistance, cellular uptake and regulating RNA expression; U.S. Pat. No. 5,858,988 which describes hydrophobic carrier agent attached to the 2'-O position of oligonucleotides to enhanced their membrane permeability and stability; U.S. Pat. No. 5,214,136 which describes oligonucleotides conjugated to anthraquinone at the 5' terminus that possess enhanced hybridization to DNA or RNA; enhanced stability to nucleases; U.S. Pat. No. 5,700,922 which describes PNA-DNA-PNA chimeras wherein the DNA comprises 2'-deoxy-erythro-pentofuranosyl nucleotides for enhanced nuclease resistance, binding affinity, and ability to activate RNase H; and U.S. Pat. No. 5,708,154 which describes RNA linked to a DNA to form a DNA-RNA hybrid.

E. Polyether and Peptide Nucleic Acids

In certain embodiments, it is contemplated that a nucleic acid comprising a derivative or analog of a nucleoside or nucleotide may be used in the methods and compositions of the invention. A non-limiting example is a "polyether nucleic acid", described in U.S. Pat. No. 5,908,845, incorporated herein by reference. In a polyether nucleic acid, one or more nucleobases are linked to chiral carbon atoms in a polyether backbone.

Another non-limiting example is a "peptide nucleic acid", also known as a "PNA", "peptide-based nucleic acid analog" or "PENAM", described in U.S. Pat. Nos. 5,786,461, 5,891, 625, 5,773,571, 5,766,855, 5,736,336, 5,719,262, 5,714,331, 5,539,082, and WO 92/20702, each of which is incorporated herein by reference. Peptide nucleic acids generally have enhanced sequence specificity, binding properties, and resistance to enzymatic degradation in comparison to molecules such as DNA and RNA (Egholm et al., 1993; PCT/EP/ 01219). A peptide nucleic acid generally comprises one or more nucleotides or nucleosides that comprise a nucleobase moiety, a nucleobase linker moeity that is not a 5-carbon sugar, and/or a backbone moiety that is not a phosphate backbone moiety. Examples of nucleobase linker moieties described for PNAs include aza nitrogen atoms, amido and/or ureido tethers (see for example, U.S. Pat. No. 5,539, 082). Examples of backbone moieties described for PNAs include an aminoethylglycine, polyamide, polyethyl, polythioamide, polysulfinamide or polysulfonamide backbone moiety.

In certain embodiments, a nucleic acid analogue such as a peptide nucleic acid may be used to inhibit nucleic acid amplification, such as in PCR, to reduce false positives and discriminate between single base mutants, as described in U.S. Pat. No. 5,891,625. Other modifications and uses of nucleic acid analogs are known in the art, and are encompassed by the gp36 polynucleotide. In a non-limiting example, U.S. Pat. No. 5,786,461 describes PNAs with amino acid side chains attached to the PNA backbone to enhance solubility of the molecule. In another example, the cellular uptake property of PNAs is increased by attachment of a lipophilic group. U.S. Application Ser. No. 117,363 describes several alkylamino moeities used to enhance cellular uptake of a PNA. Another example is described in U.S. Pat. Nos. 5,766,855, 5,719,262, 5,714,331 and 5,736,336, which describe PNAs comprising naturally and non-naturally occurring nucleobases and alkylamine side chains that provide improvements in sequence specificity, solubility and/or binding affinity relative to a naturally occurring nucleic acid.

F. Preparation of Nucleic Acids

A nucleic acid may be made by any technique known to one of ordinary skill in the art, such as for example, chemical synthesis, enzymatic production or biological production. Non-limiting examples of a synthetic nucleic acid (e.g., a synthetic oligonucleotide), include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 1989, incorporated herein by reference).

G. Purification of Nucleic Acids

A nucleic acid may be purified on polyacrylamide gels, cesium chloride centrifugation gradients, or by any other means known to one of ordinary skill in the art (see for example, Sambrook et al., 1989, incorporated herein by reference).

In certain aspect, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, bulk of cellular components or in vitro reaction components such as for example, macromolecules such as lipids or proteins, small biological molecules, and the like.

H. Nucleic Acid Segments

In certain embodiments, the nucleic acid is a nucleic acid segment. As used herein, the term "nucleic acid segment," are smaller fragments of a nucleic acid, such as for non-limiting example, those that encode only part of the peptide or polypeptide sequence. Thus, a "nucleic acid segment" may comprise any part of a gene sequence, of from about 2 nucleotides to the full length of the peptide or polypeptide encoding region.

Various nucleic acid segments may be designed based on a particular nucleic acid sequence, and may be of any length.

By assigning numeric values to a sequence, for example, the first residue is 1, the second residue is 2, etc., an algorithm defining all nucleic acid segments can be generated:

n to n+y where n is an integer from 1 to the last number of the sequence and y is the length of the nucleic acid segment minus one, where n+y does not exceed the last number of the sequence. Thus, for a 10 mer, the nucleic acid segments correspond to bases 1 to 10, 2 to 11, 3 to 12 . . . and so on. For a 15-mer, the nucleic acid segments correspond to bases 1 to 15, 2 to 16, 3 to 17 . . . and so on. For a 20-mer, the nucleic segments correspond to bases 1 to 20, 2 to 21, 3 to 22 . . . and so on. In certain embodiments, the nucleic acid segment may be a probe or primer. As used herein, a "probe" generally refers to a nucleic acid used in a detection method or composition. As used herein, a "primer" generally refers to a nucleic acid used in an extension or amplification method or composition.

I. Nucleic Acid Complements

The present invention also encompasses a nucleic acid that is complementary to one or more other nucleic acids. In specific embodiments, for example, a nucleic acid is employed for antisense or siRNA purposes, such as to inhibit at least partially expression of a polynucleotide.

In particular embodiments the invention encompasses a nucleic acid or a nucleic acid segment complementary to the sequence set forth herein, for example. A nucleic acid is "complement(s)" or is "complementary" to another nucleic acid when it is capable of base-pairing with another nucleic acid according to the standard Watson-Crick, Hoogsteen or reverse Hoogsteen binding complementarity rules. As used herein "another nucleic acid" may refer to a separate molecule or a spatial separated sequence of the same molecule.

As used herein, the term "complementary" or "complement(s)" also refers to a nucleic acid comprising a sequence of consecutive nucleobases or semiconsecutive nucleobases (e.g., one or more nucleobase moieties are not present in the molecule) capable of hybridizing to another nucleic acid strand or duplex even if less than all the nucleobases do not base pair with a counterpart nucleobase. In certain embodiments, a "complementary" nucleic acid comprises a sequence in which about 70%, about 71%, about 72%, about 73%, about 74%, about 75%, about 76%, about 77%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, to about 100%, and any range derivable therein, of the nucleobase sequence is capable of base-pairing with a single or double stranded nucleic acid molecule during hybridization. In certain embodiments, the term "complementary" refers to a nucleic acid that may hybridize to another nucleic acid strand or duplex in stringent conditions, as would be understood by one of ordinary skill in the art.

In certain embodiments, a "partly complementary" nucleic acid comprises a sequence that may hybridize in low stringency conditions to a single or double stranded nucleic acid, or contains a sequence in which less than about 70% of the nucleobase sequence is capable of base-pairing with a single or double stranded nucleic acid molecule during hybridization.

J. Hybridization

As used herein, "hybridization", "hybridizes" or "capable of hybridizing" is understood to mean the forming of a double or triple stranded molecule or a molecule with partial double or triple stranded nature. The term "anneal" as used herein is synonymous with "hybridize." The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand.

Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.15 M NaCl, for example, at temperatures of about 50° C. to about 70° C. or, for example, wherein said stringent conditions are hybridization at 50-65° C., 5×SSPC, 50% formamide; wash 50-65° C., 5×SSPC; or wash at 60° C., 0.5×SSC, 0.1% SDS. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions", and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suite a particular application.

V. Nucleic Acid-Based Expression Systems

In particular embodiments, the present invention concerns a polynucleotide that encodes an immunoreactive ehrlichiae polypeptide, and also includes delivering the polynucleotide encoding the polypeptide, or encoded product thereof, to an individual in need thereof, such as an individual infected with *Erhlichia* and/or an individual susceptible to being infected with *Erhlichia*. For the sake of brevity, the following section will refer to any *E. canis* gp19 nucleic acid compositions and/or nucleic acid-based expression system of the present invention.

The present invention is directed toward substantially pure and/or isolated DNA sequence encoding an immunoreactive *Ehrlichia* composition. Generally, the encoded protein comprises an N-terminal sequence, which may be cleaved after post-translational modification resulting in the production of mature protein.

It is well-known in the art that because of the degeneracy of the genetic code (i.e., for most amino acids, more than one nucleotide triplet (codon) codes for a single amino acid), different nucleotide sequences can code for a particular amino acid, or polypeptide. Thus, the polynucleotide sequences of the subject invention include any of the provided exemplary sequences or a degenerate variant of such a sequence, for example. In particular aspects of the invention, a degenerate variant comprises a sequence that is not identical to a sequence of the invention but that still retains one or more properties of a sequence of the invention.

As used herein, "substantially pure DNA" means DNA that is not part of a milieu in which the DNA naturally occurs, by virtue of separation (partial or total purification) of some or all of the molecules of that milieu, or by virtue of alteration of sequences that flank the claimed DNA. The term therefore includes, for example, a recombinant DNA which is incorporated into a vector, into an autonomously replicating plasmid or virus, or into the genomic DNA of a prokaryote or eukaryote; or that exists as a separate molecule (e.g., a cDNA or a genomic or cDNA fragment produced by polymerase chain reaction (PCR) or restriction endonuclease digestion) independent of other sequences. It also includes a recombinant DNA, which is part of a hybrid gene encoding additional polypeptide sequence, e.g., a fusion protein.

The present invention is further directed to an expression vector comprising a polynucleotide encoding an immunoreactive Ehrlichiae composition and capable of expressing the polynucleotide when the vector is introduced into a cell. In specific embodiments, the vector comprises in operable linkage the following: a) an origin of replication; b) a promoter; and c) a DNA sequence coding for the protein.

As used herein "vector" may be defined as a replicable nucleic acid construct, e.g., a plasmid or viral nucleic acid. Vectors may be used to amplify and/or express nucleic acid encoding an immunoreactive composition of Ehrlichiae. An expression vector is a replicable construct in which a nucleic acid sequence encoding a polypeptide is operably linked to suitable control sequences capable of effecting expression of the polypeptide in a cell. The need for such control sequences will vary depending upon the cell selected and the transformation method chosen. Generally, control sequences include a transcriptional promoter and/or enhancer, suitable mRNA ribosomal binding sites, and sequences that control the termination of transcription and translation, for example. Methods that are well-known to those skilled in the art can be used to construct expression vectors comprising appropriate transcriptional and translational control signals. See for example, the techniques described in Sambrook et al., 1989, Molecular Cloning: A Laboratory Manual (2nd Ed.), Cold Spring Harbor Press, N.Y. A polynucleotide sequence to be expressed and its transcription control sequences are defined as being "operably linked" if the transcription control sequences effectively control the transcription of the polynucleotide sequence. Vectors of the invention include, but are not limited to, plasmid vectors and viral vectors. Preferred viral vectors of the invention are those derived from retroviruses, adenovirus, adeno-associated virus, SV40 virus, or herpes viruses, for example.

In general, expression vectors comprise promoter sequences that facilitate the efficient transcription of the polynucleotide to be expressed, are used in connection with a host cell. As used herein, the term "host" is meant to include not only prokaryotes but also eukaryotes, such as yeast, plant and animal cells. A recombinant polynucleotide that encodes an immunoreactive composition of Ehrlichiae of the present invention can be used to transform a host using any of the techniques commonly known to those of ordinary skill in the art. Prokaryotic hosts may include *E. coli, S. tymphimurium, Serratia marcescens* and *Bacillus subtilis*. Eukaryotic hosts include yeasts, such as *Pichia pastoris*, mammalian cells and insect cells.

The following description concerns exemplary elements, reagents, and methods for polynucleotides and nucleic acid delivery of an *Ehrlichia* polynucleotide.

A. Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30 110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the beta lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell, organelle, cell type, tissue, organ, or organism chosen for expression. Those of skill in the art of molecular biology generally know the use of promoters, enhancers, and cell type combinations for protein expression, (see, for example Sambrook et al., 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

The promoter may be one suitable for use in a prokaryotic cell, a eukaryotic cell, or both. Additionally any promoter/enhancer combination (as per, for example, the Eukaryotic Promoter Data Base EPDB) could also be used to drive expression. Use of a T3, T7 or SP6 cytoplasmic expression system is one possible embodiment.

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

3. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference.)

5. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

6. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

7. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

8. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

9. Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, *E. coli* is often transformed using derivatives of pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™ 11 may be utilized in making a recombinant phage vector which can be used to transform host cells, such as, for example, *E. coli* LE392.

Further useful plasmid vectors include pIN vectors (Inouye et al., 1985); and pGEX vectors, for use in generating glutathione S transferase (GST) soluble fusion proteins for later purification and separation or cleavage. Other suitable fusion proteins are those with beta galactosidase, ubiquitin, and the like.

Bacterial host cells, for example, *E. coli*, comprising the expression vector are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

10. Viral Vectors

The ability of certain viruses to infect cells or enter cells via receptor mediated endocytosis, and to integrate into host cell genome and express viral genes stably and efficiently have made them attractive candidates for the transfer of foreign nucleic acids into cells (e.g., mammalian cells). Components of the present invention may comprise a viral vector that encode one or more compositions or other components such as, for example, an immunomodulator or adjuvant. Non-limiting examples of virus vectors that may be used to deliver a nucleic acid of the present invention are described below.

a. Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell specific construct that has been cloned therein. Knowledge of the genetic organization or adenovirus, a 36 kb, linear, double stranded DNA virus, allows substitution of large pieces of adenoviral DNA with foreign sequences up to 7 kb (Grunhaus and Horwitz, 1992).

b. AAV Vectors

The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno associated virus (AAV) is an attractive vector system for use in the compositions of the present invention as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

c. Retroviral Vectors

Retroviruses have useful as delivery vectors due to their ability to integrate their genes into the host genome, transferring a large amount of foreign genetic material, infecting a broad spectrum of species and cell types and of being packaged in special cell lines (Miller, 1992).

In order to construct a retroviral vector, a nucleic acid (e.g., one encoding a composition of interest) is inserted into the viral genome in the place of certain viral sequences to produce a virus that is replication defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

d. Other Viral Vectors

Other viral vectors may be employed as vaccine constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

e. Delivery Using Modified Viruses

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

11. Vector Delivery and Cell Transformation

Suitable methods for ehrlichial nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium* mediated transformation (U.S. Pat. Nos. 5,591,616 and 5,563,055, each incorporated herein by reference); by PEG mediated transformation of protoplasts (Omirulleh et al., 1993; U.S. Pat. Nos. 4,684,611 and 4,952,500, each incorporated herein by reference); by desiccation/inhibition mediated DNA uptake (Potrykus et al., 1985), and any combination of such methods. Through the application of techniques such as these, organelle(s), cell(s), tissue(s) or organism(s) may be stably or transiently transformed.

a. Ex Vivo Transformation

Methods for tranfecting vascular cells and tissues removed from an organism in an ex vivo setting are known to those of skill in the art. For example, cannine endothelial cells have been genetically altered by retroviral gene transfer in vitro and transplanted into a canine (Wilson et al., 1989). In another example, yucatan minipig endothelial cells were transfected by retrovirus in vitro and transplanted into an artery using a double-balloon catheter (Nabel et al., 1989). Thus, it is contemplated that cells or tissues may be removed and transfected ex vivo using the nucleic acids of the present invention. In particular aspects, the transplanted cells or tissues may be placed into an organism. In preferred facets, a nucleic acid is expressed in the transplated cells or tissues.

b. Injection

In certain embodiments, a nucleic acid may be delivered to an organelle, a cell, a tissue or an organism via one or more injections (i.e., a needle injection), such as, for example, subcutaneously, intradermally, intramuscularly, intervenously, intraperitoneally, etc. Methods of injection of vaccines are well known to those of ordinary skill in the art (e.g., injection of a composition comprising a saline solution). Further embodiments of the present invention include the introduction of a nucleic acid by direct microinjection. Direct microinjection has been used to introduce nucleic acid constructs into *Xenopus* oocytes (Harland and Weintraub, 1985). The amount of composition used may vary upon the nature of the antigen as well as the organelle, cell, tissue or organism used c. Electroporation In certain embodiments of the present invention, a nucleic acid is introduced into an organelle, a cell, a tissue or an organism via electroporation. Electroporation involves the exposure of a suspension of cells and DNA to a high voltage electric discharge. In some variants of this method, certain cell wall degrading enzymes, such as pectin degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre B lymphocytes have been transfected with human kappa immunoglobulin genes (Potter et al., 1984), and rat hepatocytes have been transfected with the chloramphenicol acetyltransferase gene (Tur Kaspa et al., 1986) in this manner.

To effect transformation by electroporation in cells such as, for example, plant cells, one may employ either friable tissues, such as a suspension culture of cells or embryogenic callus or alternatively one may transform immature embryos or other organized tissue directly. In this technique, one would partially degrade the cell walls of the chosen cells by exposing them to pectin degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plant cells (Bates, 1994; Lazzeri, 1995). For example, the generation of transgenic soybean plants by electroporation of cotyledon derived protoplasts is described by Dhir and Widholm in International Patent Application No. WO 9217598, incorporated herein by reference. Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

d. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV 1, BHK, NIH3T3 and HeLa cells were transfected with a neomycin marker gene (Chen and Okayama, 1987), and rat hepatocytes were transfected with a variety of marker genes (Rippe et al., 1990).

e. DEAE Dextran

In another embodiment, a nucleic acid is delivered into a cell using DEAE dextran followed by polyethylene glycol. In this manner, reporter plasmids were introduced into mouse myeloma and erythroleukemia cells (Gopal, 1985).

f. Sonication Loading

Additional embodiments of the present invention include the introduction of a nucleic acid by direct sonic loading. LTK fibroblasts have been transfected with the thymidine kinase gene by sonication loading (Fechheimer et al., 1987).

g. Liposome-Mediated Transfection

In a further embodiment of the invention, an ehrlichial nucleic acid may be comprised with a lipid complex such as, for example, comprised in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen).

Liposome-mediated nucleic acid delivery and expression of foreign DNA in vitro has been very successful (Nicolau and Sene, 1982; Fraley et al., 1979; Nicolau et al., 1987). The feasibility of liposome mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome encapsulated DNA (Kaneda et al., 1989). In other embodiments, a liposome may be complexed or employed in conjunction with nuclear non histone chromosomal proteins (HMG 1) (Kato et al., 1991). In yet further embodiments, a liposome may be complexed or employed in conjunction with both HVJ and HMG 1. In other embodiments, a delivery vehicle may comprise a ligand and a liposome.

h. Receptor-Mediated Transfection

Still further, a nucleic acid may be delivered to a target cell via receptor mediated delivery vehicles. These take advantage of the selective uptake of macromolecules by receptor-mediated endocytosis that will be occurring in a target cell. In view of the cell type specific distribution of various receptors, this delivery method adds another degree of specificity to the present invention.

Certain receptor mediated gene targeting vehicles comprise a cell receptor specific ligand and a nucleic acid binding agent. Others comprise a cell receptor specific ligand to which the nucleic acid to be delivered has been operatively attached. Several ligands have been used for receptor mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell specific binding. For example, lactosyl ceramide, a galactose terminal asialganglioside, have been incorporated into liposomes and observed an increase in the uptake of the insulin gene by hepatocytes (Nicolau et al., 1987). It is contemplated that the tissue specific transforming constructs of the present invention can be specifically delivered into a target cell in a similar manner.

i. Microprojectile Bombardment

Microprojectile bombardment techniques can be used to introduce a nucleic acid into at least one, organelle, cell, tissue or organism (U.S. Pat. No. 5,550,318; U.S. Pat. No. 5,538,880; U.S. Pat. No. 5,610,042; and PCT Application WO 94/09699; each of which is incorporated herein by reference). This method depends on the ability to accelerate DNA coated microprojectiles to a high velocity allowing them to pierce cell membranes and enter cells without killing them (Klein et al., 1987). There are a wide variety of microprojectile bombardment techniques known in the art, many of which are applicable to the invention.

Microprojectile bombardment may be used to transform various cell(s), tissue(s) or organism(s), such as for example any plant species. Examples of species which have been transformed by microprojectile bombardment include monocot species such as maize (PCT Application WO 95/06128), barley (Ritala et al., 1994; Hensgens et al., 1993), wheat (U.S. Pat. No. 5,563,055, incorporated herein by reference), rice (Hensgens et al., 1993), oat (Torbet et al., 1995; Torbet et al., 1998), rye (Hensgens et al., 1993), sugarcane (Bower et al., 1992), and sorghum (Casas et al., 1993; Hagio et al., 1991); as well as a number of dicots including tobacco (Tomes et al., 1990; Buising and Benbow, 1994), soybean (U.S. Pat. No. 5,322,783, incorporated herein by reference), sunflower (Knittel et al. 1994), peanut (Singsit et al., 1997), cotton (McCabe and Martinell, 1993), tomato (VanEck et al. 1995), and legumes in general (U.S. Pat. No. 5,563,055, incorporated herein by reference).

In this microprojectile bombardment, one or more particles may be coated with at least one nucleic acid and delivered into cells by a propelling force. Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold particles or beads. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into a cell (e.g., a plant cell) by acceleration is the Biolistics Particle Delivery System, which can be used to propel particles coated with DNA or cells through a screen, such as a stainless steel or Nytex screen, onto a filter surface covered with cells, such as for example, a monocot plant cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

12. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid.

In certain embodiments, it is contemplated that RNAs or proteinaceous sequences may be co-expressed with other selected RNAs or proteinaceous sequences in the same host cell. Co-expression may be achieved by co-transfecting the host cell with two or more distinct recombinant vectors. Alternatively, a single recombinant vector may be constructed to include multiple distinct coding regions for RNAs, which could then be expressed in host cells transfected with the single vector.

A tissue may comprise a host cell or cells to be transformed with a composition of the invention. The tissue may be part or separated from an organism. In certain embodiments, a tissue may comprise, but is not limited to, adipocytes, alveolar, ameloblasts, axon, basal cells, blood (e.g., lymphocytes), blood vessel, bone, bone marrow, brain, breast, cartilage, cervix, colon, cornea, embryonic, endometrium, endothelial, epithelial, esophagus, facia, fibroblast, follicular, ganglion cells, glial cells, goblet cells, kidney, liver, lung, lymph node, muscle, neuron, ovaries, pancreas, peripheral blood, prostate, skin, skin, small intestine, spleen, stem cells, stomach, testes, anthers, ascite tissue, cobs, ears, flowers, husks, kernels, leaves, meristematic cells, pollen, root tips, roots, silk, stalks, and all cancers thereof.

In certain embodiments, the host cell or tissue may be comprised in at least one organism. In certain embodiments, the organism may be, but is not limited to, a prokayote (e.g., a eubacteria, an archaea) or an eukaryote, as would be understood by one of ordinary skill in the art (see, for example, webpage phylogeny.arizona.edu/tree/phylogeny.html).

Numerous cell lines and cultures are available for use as a host cell, and they can be obtained through the American Type Culture Collection (ATCC), which is an organization that serves as an archive for living cultures and genetic materials (world wide web at atcc.org). An appropriate host can be determined by one of skill in the art based on the vector backbone and the desired result. A plasmid or cosmid, for example, can be introduced into a prokaryote host cell for replication of many vectors. Cell types available for vector replication and/or expression include, but are not limited to, bacteria, such as *E. coli* (e.g., *E. coli* strain RR1, *E. coli* LE392, *E. coli* B, *E. coli* X 1776 (ATCC No. 31537) as well as *E. coli* W3110 (F, lambda, prototrophic, ATCC No. 273325), DH5α, JM109, and KCB, bacilli such as *Bacillus subtilis*; and other enterobacteriaceae such as *Salmonella typhimurium*, *Serratia marcescens*, various *Pseudomonas* specie, as well as a number of commercially available bacterial hosts such as SURE® Competent Cells and SOLOPACK Gold Cells (STRATAGENE®, La Jolla). In certain embodiments, bacterial cells such as *E. coli* LE392 are particularly contemplated as host cells for phage viruses.

Examples of eukaryotic host cells for replication and/or expression of a vector include, but are not limited to, HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

13. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'s COMPLETE CONTROL Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

It is contemplated that the proteins, polypeptides or peptides produced by the methods of the invention may be "overexpressed", i.e., expressed in increased levels relative to its natural expression in cells. Such overexpression may be assessed by a variety of methods, including radio labeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein, polypeptide or peptide in comparison to the level in natural cells is indicative of overexpression, as is a relative abundance of the specific protein, polypeptides or peptides in relation to the other proteins produced by the host cell and, e.g., visible on a gel.

In some embodiments, the expressed proteinaceous sequence forms an inclusion body in the host cell, the host cells are lysed, for example, by disruption in a cell homogenizer, washed and/or centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed. Inclusion bodies may be solubilized in solutions containing high concentrations of urea (e.g. 8M) or chaotropic agents such as guanidine hydrochloride in the presence of reducing agents, such as beta mercaptoethanol or DTT (dithiothreitol), and refolded into a more desirable conformation, as would be known to one of ordinary skill in the art.

VI. Biological Functional Equivalents

As modifications and/or changes may be made in the structure of the polynucleotides and and/or proteins according to the present invention, while obtaining molecules having similar or improved characteristics, such biologically functional equivalents are also encompassed within the present invention.

A. Modified Polynucleotides and Polypeptides

The biological functional equivalent may comprise a polynucleotide that has been engineered to contain distinct sequences while at the same time retaining the capacity to encode the "wild-type" or standard protein. This can be accomplished to the degeneracy of the genetic code, i.e., the presence of multiple codons, which encode for the same amino acids. In one example, one of skill in the art may wish to introduce a restriction enzyme recognition sequence into a polynucleotide while not disturbing the ability of that polynucleotide to encode a protein.

In another example, a polynucleotide made be (and encode) a biological functional equivalent with more significant changes. Certain amino acids may be substituted for other amino acids in a protein structure without appreciable loss of interactive binding capacity with structures such as, for example, antigen-binding regions of antibodies, binding sites on substrate molecules, receptors, and such like. So-called "conservative" changes do not disrupt the biological activity of the protein, as the structural change is not one that impinges of the protein's ability to carry out its designed function. It is thus contemplated by the inventors that various changes may be made in the sequence of genes and proteins disclosed herein, while still fulfilling the goals of the present invention.

In terms of functional equivalents, it is well understood by the skilled artisan that, inherent in the definition of a "biologically functional equivalent" protein and/or polynucleotide, is the concept that there is a limit to the number of changes that may be made within a defined portion of the molecule while retaining a molecule with an acceptable level of equivalent biological activity. Biologically functional equivalents are thus defined herein as those proteins (and polynucleotides) in selected amino acids (or codons) may be substituted. Functional activity.

In general, the shorter the length of the molecule, the fewer changes that can be made within the molecule while retaining function. Longer domains may have an intermediate number of changes. The full-length protein will have the most tolerance for a larger number of changes. However, it must be appreciated that certain molecules or domains that are highly dependent upon their structure may tolerate little or no modification.

Amino acid substitutions are generally based on the relative similarity of the amino acid side-chain substituents, for example, their hydrophobicity, hydrophilicity, charge, size, and/or the like. An analysis of the size, shape and/or type of the amino acid side-chain substituents reveals that arginine, lysine and/or histidine are all positively charged residues; that alanine, glycine and/or serine are all a similar size; and/or that phenylalanine, tryptophan and/or tyrosine all have a generally similar shape. Therefore, based upon these considerations, arginine, lysine and/or histidine; alanine, glycine and/or serine; and/or phenylalanine, tryptophan and/or tyrosine; are defined herein as biologically functional equivalents.

To effect more quantitative changes, the hydropathic index of amino acids may be considered. Each amino acid has been assigned a hydropathic index on the basis of their hydrophobicity and/or charge characteristics, these are: isoleucine (+4.5); valine (+4.2); leucine (+3.8); phenylalanine (+2.8); cysteine/cystine (+2.5); methionine (+1.9); alanine (+1.8); glycine (0.4); threonine (0.7); serine (0.8); tryptophan (0.9); tyrosine (1.3); proline (1.6); histidine (3.2); glutamate (3.5); glutamine (3.5); aspartate (3.5); asparagine (3.5); lysine (3.9); and/or arginine (4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index and/or score and/or still retain a similar biological activity. In making changes based upon the hydropathic index, the substitution of amino acids whose hydropathic indices are within ±2 is preferred, those which are within ±1 are particularly preferred, and/or those within ±0.5 are even more particularly preferred.

It also is understood in the art that the substitution of like amino acids can be made effectively on the basis of hydrophilicity, particularly where the biological functional equivalent protein and/or peptide thereby created is intended for use in immunological embodiments, as in certain embodiments of the present invention. U.S. Pat. No. 4,554,101, incorporated herein by reference, states that the greatest local average hydrophilicity of a protein, as governed by the hydrophilicity of its adjacent amino acids, correlates with its immunogenicity and/or antigenicity, i.e., with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (0.4); proline (~0.5±1); alanine (0.5); histidine (0.5); cysteine (1.0); methionine (1.3); valine (1.5); leucine (1.8); isoleucine (1.8); tyrosine (2.3); phenylalanine (2.5); tryptophan (3.4). In making changes based upon similar hydrophilicity values, the substitution of amino acids whose hydrophilicity values are within ±2 is preferred, those which are within ±1 are particularly preferred, and/or those within ±0.5 are even more particularly preferred.

B. Altered Amino Acids

The present invention, in many aspects, relies on the synthesis of peptides and polypeptides in cyto, via transcription and translation of appropriate polynucleotides. These peptides and polypeptides will include the twenty "natural" amino acids, and post-translational modifications thereof. However, in vitro peptide synthesis permits the use of modified and/or unusual amino acids. Table 1 provides exemplary, but not limiting, modified and/or unusual amino acids

C. Mimetics

In addition to the biological functional equivalents discussed above, the present inventors also contemplate that structurally similar compounds may be formulated to mimic the key portions of peptide or polypeptides of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Some successful applications of the peptide mimetic concept have focused on mimetics of β-turns within proteins, which are known to be highly antigenic. Likely β turn structure within a polypeptide can be predicted by computer-based algorithms, as discussed herein. Once the component amino acids of the turn are determined, mimetics can be constructed to achieve a similar spatial orientation of the essential elements of the amino acid side chains.

Other approaches have focused on the use of small, multidisulfide-containing proteins as attractive structural templates for producing biologically active conformations that mimic the binding sites of large proteins. Vita et al. (1998). A structural motif that appears to be evolutionarily conserved in certain toxins is small (30-40 amino acids), stable, and high permissive for mutation. This motif is composed of a beta sheet and an alpha helix bridged in the interior core by three disulfides.

Beta II turns have been mimicked successfully using cyclic L-pentapeptides and those with D-amino acids. Weisshoff et al. (1999). Also, Johannesson et al. (1999) report on bicyclic tripeptides with reverse turn inducing properties.

Methods for generating specific structures have been disclosed in the art. For example, alpha-helix mimetics are disclosed in U.S. Pat. Nos. 5,446,128; 5,710,245; 5,840,833; and 5,859,184. Theses structures render the peptide or protein more thermally stable, also increase resistance to proteolytic degradation. Six, seven, eleven, twelve, thirteen and fourteen membered ring structures are disclosed.

Methods for generating conformationally restricted beta turns and beta bulges are described, for example, in U.S. Pat. Nos. 5,440,013; 5,618,914; and 5,670,155. Beta-turns permit changed side substituents without having changes in corresponding backbone conformation, and have appropriate termini for incorporation into peptides by standard synthesis procedures. Other types of mimetic turns include reverse and gamma turns. Reverse turn mimetics are disclosed in U.S. Pat. Nos. 5,475,085 and 5,929,237, and gamma turn mimetics are described in U.S. Pat. Nos. 5,672,681 and 5,674,976.

VII. Immunological Compositions

In particular embodiments of the invention, immunological compositions are employed. For the sake of brevity, the following section will refer to any *E. canis* gp19 immunological compositions of the present invention, such as are described elsewhere herein as only exemplary embodiments. For example, the compositions may include all or part of an *E. canis* gp19 polypeptide, such as one comprising part or all of SEQ ID NO:17 or SEQ ID NO:19, a gp19 polynucleotide, such as one comprising part or all of SEQ ID NO:16 or SEQ ID NO:18, a peptide, such as one comprising SEQ ID NO:13, an antibody to a polypeptide or peptide of the invention, or a mixture thereof, for example. Antibodies may be utilized to bind an antigen, thereby rendering the molecule at least partially ineffective for its activity, for example. In other embodiments, antibodies to the antigen are employed in diagnostic aspects of the invention, such as for detecting the presence of the antigen from a sample. Exemplary samples may be from an animal suspected of having *E. canis* or *E. chaffeensis* infection, from an animal susceptible to *E. canis* or *E. chaffeensis* infection, or from an animal that has an *E. canis* or *E. chaffeensis* infection.

Exemplary samples may be obtained from blood, serum, cerebrospinal fluid, urine, feces, cheek scrapings, nipple aspirate, and so forth.

Purified immunoreactive compositions or antigenic fragments of the immunoreactive compositions can be used to generate new antibodies or to test existing antibodies (e.g., as positive controls in a diagnostic assay) by employing standard protocols known to those skilled in the art.

As is well known in the art, immunogenicity to a particular immunogen can be enhanced by the use of non-specific stimulators of the immune response known as adjuvants. Exemplary and preferred adjuvants include complete BCG, Detox, (RIBI, Immunochem Research Inc.), ISCOMS and aluminum hydroxide adjuvant (Superphos, Biosector).

Included in this invention are polyclonal antisera generated by using the immunoreactive composition or a fragment of the immunoreactive composition as an immunogen in, e.g., rabbits. Standard protocols for monoclonal and polyclonal antibody production known to those skilled in this art are employed. The monoclonal antibodies generated by this procedure can be screened for the ability to identify recombinant *Ehrlichia* cDNA clones, and to distinguish them from known cDNA clones, for example.

The invention encompasses not only an intact monoclonal antibody, but also an immunologically-active antibody fragment, e.g., a Fab or (Fab)2 fragment; an engineered single chain scFv molecule; or a chimeric molecule, e.g., an antibody which contains the binding specificity of one antibody, e.g., of murine origin, and the remaining portions of another antibody, e.g., of human origin.

In one embodiment, the antibody, or fragment thereof, may be linked to a toxin or to a detectable label, e.g. a radioactive label, non-radioactive isotopic label, fluorescent label, chemiluminescent label, paramagnetic label, enzyme label or colorimetric label. Examples of suitable toxins include diphtheria toxin, *Pseudomonas* exotoxin A, ricin, and cholera toxin. Examples of suitable enzyme labels include malate hydrogenase, staphylococcal nuclease, delta-5-steroid isomerase, alcohol dehydrogenase, alpha glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholinesterase, etc. Examples of suitable radioisotopic labels include $^3$H, $^{125}$I, $^{131}$I, $^{32}$P, $^{35}$S, $^{14}$C, etc.

Paramagnetic isotopes for purposes of in vivo diagnosis can also be used according to the methods of this invention. There are numerous examples of elements that are useful in magnetic resonance imaging. For discussions on in vivo nuclear magnetic resonance imaging, see, for example, Schaefer et al., (1989) JACC 14, 472-480; Shreve et al., (1986) Magn. Reson. Med. 3, 336-340; Wolf, G. L., (1984) Physiol. Chem. Phys. Med. NMR 16, 93-95; Wesby et al., (1984) Physiol. Chem. Phys. Med. NMR 16, 145-155; Runge et al., (1984) Invest. Radiol. 19, 408-415. Examples of suitable fluorescent labels include a fluorescein label, an isothiocyalate label, a rhodamine label, a phycoerythrin label, a phycocyanin label, an allophycocyanin label, an opthaldehyde label, a fluorescamine label, etc. Examples of chemiluminiscent labels include a luminal label, an isoluminal label, an aromatic acridinium ester label, a luciferin label, a luciferase label, an aequorin label, etc.

Those of ordinary skill in the art will know of these and other suitable labels, which may be employed in accordance with the present invention. The binding of these labels to antibodies or fragments thereof can be accomplished using standard techniques commonly known to those of ordinary skill in the art. Typical techniques are described by Kennedy et al., (1976) Clin. Chim. Acta 70, 1-31; and Schurs et al., (1977) Clin. Chim. Acta 81, 1-40. Coupling techniques mentioned in the later are the glutaraldehyde method, the periodate method, the dimaleimide method, the maleimido-benzyl-N-hydroxy-succinimde ester method. All of these methods are incorporated by reference herein.

D. Antibodies

In certain aspects of the invention, one or more antibodies may be produced to the expressed gp36 or gp47. These antibodies may be used in various diagnostic and/or therapeutic applications described herein.

As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

The term "antibody" is used to refer to any antibody-like molecule that has an antigen binding region, and includes antibody fragments such as Fab', Fab, F(ab')2, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

"Mini-antibodies" or "minibodies" are also contemplated for use with the present invention. Minibodies are sFv polypeptide chains which include oligomerization domains at their C-termini, separated from the sFv by a hinge region. Pack et al. (1992) Biochem 31:1579-1584. The oligomerization domain comprises self-associating $\alpha$-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art. See, e.g., Pack et al. (1992) Biochem 31:1579-1584; Cumber et al. (1992) J Immunology 149B:120-126.

Antibody-like binding peptidomimetics are also contemplated in the present invention. Liu et al. Cell Mol Biol (Noisy-le-grand). 2003 March; 49(2):209-16 describe "antibody like binding peptidomimetics" (ABiPs), which are peptides that act as pared-down antibodies and have certain advantages of longer serum half-life as well as less cumbersome synthesis methods.

Monoclonal antibodies (MAbs) are recognized to have certain advantages, e.g., reproducibility and large-scale production, and their use is generally preferred. The invention thus provides monoclonal antibodies of the human, murine, monkey, rat, hamster, rabbit and even chicken origin. Due to the ease of preparation and ready availability of reagents, murine monoclonal antibodies will often be preferred.

However, "humanized" antibodies are also contemplated, as are chimeric antibodies from mouse, rat, or other species, bearing human constant and/or variable region domains, bispecific antibodies, recombinant and engineered antibodies and fragments thereof. As used herein, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". A "humanized antibody" is an antibody comprising a humanized light chain and a humanized heavy chain immunoglobulin.

E. Exemplary Methods for Generating Monoclonal Antibodies

Exemplary methods for generating monoclonal antibodies (MAbs) generally begin along the same lines as those for preparing polyclonal antibodies. Briefly, a polyclonal antibody is prepared by immunizing an animal with a LEE or CEE composition in accordance with the present invention and collecting antisera from that immunized animal.

A wide range of animal species can be used for the production of antisera. Typically the animal used for production of antisera is a rabbit, a mouse, a rat, a hamster, a guinea pig or a goat. The choice of animal may be decided upon the ease of manipulation, costs or the desired amount of sera, as would be known to one of skill in the art. Antibodies of the invention can also be produced transgenically through the generation of a mammal or plant that is transgenic for the immunoglobulin heavy and light chain sequences of interest and production of the antibody in a recoverable form therefrom. In connection with the transgenic production in mammals, antibodies can be produced in, and recovered from, the milk of goats, cows, or other mammals. See, e.g., U.S. Pat. Nos. 5,827,690, 5,756,687, 5,750,172, and 5,741,957.

As is also well known in the art, the immunogenicity of a particular immunogen composition can be enhanced by the use of non-specific stimulators of the immune response, known as adjuvants. Suitable adjuvants include all acceptable immunostimulatory compounds, such as cytokines, chemokines, cofactors, toxins, plasmodia, synthetic compositions or LEEs or CEEs encoding such adjuvants.

Adjuvants that may be used include IL-1, IL-2, IL-4, IL-7, IL-12, $\gamma$-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween® 80 (polysorbate 80) emulsion is also contemplated. MEW antigens may even be used. Exemplary, often preferred adjuvants include complete Freund's adjuvant (a non-specific stimulator of the immune response containing killed *Mycobacterium tuberculosis*), incomplete Freund's adjuvants and aluminum hydroxide adjuvant.

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (Smith/Kline, PA); low-dose Cyclophosphamide (CYP; 300 mg/m2) (Johnson/Mead, NJ), cytokines such as $\gamma$-interferon, IL-2, or IL-12 or genes encoding proteins involved in immune helper functions, such as B-7.

The amount of immunogen composition used in the production of polyclonal antibodies varies upon the nature of the immunogen as well as the animal used for immunization. A variety of routes can be used to administer the immunogen including but not limited to subcutaneous, intramuscular, intradermal, intraepidermal, intravenous and intraperitoneal. The production of polyclonal antibodies may be monitored by sampling blood of the immunized animal at various points following immunization.

A second, booster dose (e.g., provided in an injection), may also be given. The process of boosting and titering is repeated until a suitable titer is achieved. When a desired level of immunogenicity is obtained, the immunized animal can be bled and the serum isolated and stored, and/or the animal can be used to generate MAbs.

For production of rabbit polyclonal antibodies, the animal can be bled through an ear vein or alternatively by cardiac puncture. The removed blood is allowed to coagulate and then centrifuged to separate serum components from whole cells and blood clots. The serum may be used as is for various applications or else the desired antibody fraction may be purified by well-known methods, such as affinity chromatography using another antibody, a peptide bound to a solid matrix, or by using, e.g., protein A or protein G chromatography.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide, peptide or domain, be it a wild-type or mutant composition. The immunizing composition is administered in a manner effective to stimulate antibody producing cells.

The methods for generating monoclonal antibodies (MAbs) generally begin along the same lines as those for preparing polyclonal antibodies. Rodents such as mice and rats are preferred animals, however, the use of rabbit, sheep or frog cells is also possible. The use of rats may provide certain advantages (Goding, 1986, pp. 60 61), but mice are preferred, with the BALB/c mouse being most preferred as this is most routinely used and generally gives a higher percentage of stable fusions.

The animals are injected with antigen, generally as described above. The antigen may be mixed with adjuvant, such as Freund's complete or incomplete adjuvant. Booster administrations with the same antigen or DNA encoding the antigen would occur at approximately two-week intervals.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible.

Often, a panel of animals will have been immunized and the spleen of an animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma producing fusion procedures preferably are non antibody producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65 66, 1986; Campbell, pp. 75 83, 1984). cites). For example, where the immunized animal is a mouse, one may use P3 X63/Ag8, X63 Ag8.653, NS1/1.Ag 4 1, Sp210 Ag14, FO, NSO/U, MPC 11, MPC11 X45 GTG 1.7 and S194/5XX0 Bul; for rats, one may use R210.RCY3, Y3 Ag 1.2.3, IR983F and 4B210; and U 266, GM1500 GRG2, LICR LON HMy2 and UC729 6 are all useful in connection with human cell fusions. See Yoo et al., J Immunol Methods. 2002 Mar. 1; 261(1-2):1-20, for a discussion of myeloma expression systems.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8 azaguanine resistant mouse murine myeloma SP2/0 non producer cell line.

Methods for generating hybrids of antibody producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al., (1977). The use of electrically induced fusion methods is also appropriate (Goding pp. 71 74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody producing cell lines, which clones can then be propagated indefinitely to provide MAbs. The cell lines may be exploited for MAb production in two basic ways. First, a sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide MAbs in high concentration. Second, the individual cell lines could be cultured in vitro, where the MAbs are naturally secreted into the culture medium from which they can be readily obtained in high concentrations.

Further, expression of antibodies of the invention (or other moieties therefrom) from production cell lines can be enhanced using a number of known techniques. For example, the glutamine synthetase and DHFR gene expression systems are common approaches for enhancing expression under certain conditions. High expressing cell clones can be identified using conventional techniques, such as limited dilution cloning and Microdrop technology. The GS system is discussed in whole or part in connection with European Patent Nos. 0 216 846, 0 256 055, and 0 323 997 and European Patent Application No. 89303964.4.

MAbs produced by either means may be further purified, if desired, using filtration, centrifugation and various chromatographic methods such as HPLC or affinity chromatography. Fragments of the monoclonal antibodies of the invention can be obtained from the monoclonal antibodies so produced by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It is also contemplated that a molecular cloning approach may be used to generate monoclonals. In one embodiment, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination which further increases the chance of finding appropriate antibodies. In another example, LEEs or CEEs can be used to produce antigens in vitro with a cell free system. These can be used as targets for scanning single chain antibody libraries. This would enable many different antibodies to be identified very quickly without the use of animals.

Another embodiment of the invention for producing antibodies according to the present invention is found in U.S. Pat. No. 6,091,001, which describes methods to produce a cell expressing an antibody from a genomic sequence of the cell comprising a modified immunoglobulin locus using Cre-mediated site-specific recombination is disclosed. The method involves first transfecting an antibody-producing cell with a homology-targeting vector comprising a lox site and a targeting sequence homologous to a first DNA sequence adjacent to the region of the immunoglobulin loci of the genomic sequence which is to be converted to a modified region, so the first lox site is inserted into the genomic sequence via site-specific homologous recombination. Then the cell is transfected with a lox-targeting vector comprising a second lox site suitable for Cre-mediated recombination with the integrated lox site and a modifying sequence to convert the region of the immunoglobulin loci to the modified region. This conversion is performed by interacting the lox sites with Cre in vivo, so that the modifying sequence inserts into the genomic sequence via Cre-mediated site-specific recombination of the lox sites.

Alternatively, monoclonal antibody fragments encompassed by the present invention can be synthesized using an automated peptide synthesizer, or by expression of full-length gene or of gene fragments in E. coli.

F. Antibody Conjugates

The present invention further provides antibodies against gp19 proteins, polypeptides and peptides, generally of the monoclonal type, that are linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radio-labeled nucleotides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Any antibody of sufficient selectivity, specificity or affinity may be employed as the basis for an antibody conjugate. Such properties may be evaluated using conventional immunological screening methodology known to those of skill in the art. Sites for binding to biological active molecules in the antibody molecule, in addition to the canonical antigen binding sites, include sites that reside in the variable domain that can bind pathogens, B-cell superantigens, the T cell co-receptor CD4 and the HIV-1 envelope (Sasso et al., 1989; Shorki et al., 1991; Silvermann et al., 1995; Cleary et al., 1994; Lenert et al., 1990; Berberian et al., 1993; Kreier et al., 1991). In addition, the variable domain is involved in antibody self-binding (Kang et al., 1988), and contains epitopes (idiotopes) recognized by anti-antibodies (Kohler et al., 1989).

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to which they are attached to be detected, and/or further quantified if desired. Another such example is the formation of a conjugate comprising an antibody linked to a cytotoxic or anti cellular agent, and may be termed "immunotoxins".

Antibody conjugates are generally preferred for use as diagnostic agents. Antibody diagnostics generally fall within two classes, those for use in in vitro diagnostics, such as in a variety of immunoassays, and/or those for use in vivo diagnostic protocols, generally known as "antibody directed imaging".

Many appropriate imaging agents are known in the art, as are methods for their attachment to antibodies (see, for e.g., U.S. Pat. Nos. 5,021,236; 4,938,948; and 4,472,509, each incorporated herein by reference). The imaging moieties used can be paramagnetic ions; radioactive isotopes; fluorochromes; NMR-detectable substances; X-ray imaging.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium186, rhenium188, $^{75}$selenium, $^{35}$sulphur, technicium99m and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present invention may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the invention may be labeled with technetium99m by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include ALEXA 350, ALEXA 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present invention are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948, each incorporated herein by reference). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

In another embodiment of the invention, the anti-gp36 antibodies are linked to semiconductor nanocrystals such as those described in U.S. Pat. Nos. 6,048,616; 5,990,479; 5,690,807; 5,505,928; 5,262,357 (all of which are incorporated herein in their entireties); as well as PCT Publication No. 99/26299 (published May 27, 1999). In particular, exemplary materials for use as semiconductor nanocrystals in the biological and chemical assays of the present invention include, but are not limited to those described above, including group II-VI, III-V and group IV semiconductors such as ZnS, ZnSe, ZnTe, CdS, CdSe, CdTe, MgS, MgSe, MgTe, CaS, CaSe, CaTe, SrS, SrSe, SrTe, BaS, BaSe, BaTe, GaN, GaP, GaAs, GaSb, InP, InAs, InSb, AlS, AlP, AlSb, PbS, PbSe, Ge and Si and ternary and quaternary mixtures thereof. Methods for linking semiconductor nanocrystals to antibodies are described in U.S. Pat. Nos. 6,630,307 and 6,274,323.

G. Immunodetection Methods

In still further embodiments, the present invention concerns immunodetection methods for binding, purifying, removing, quantifying and/or otherwise generally detecting biological components such as immunoreactive polypeptides. The antibodies prepared in accordance with the present invention may be employed to detect wild type and/or mutant proteins, polypeptides and/or peptides. The use of wild-type and/or mutant antibodies is contemplated. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle M H and Ben-Zeev O, 1999; Gulbis B and Galand P, 1993; De Jager R et al., 1993; and Nakamura et al., 1987, each incorporated herein by reference.

In general, the immunobinding methods include obtaining a sample suspected of comprising protein, polypeptide and/or peptide, and contacting the sample with a first anti-gp19 antibody in accordance with the present invention, as the case may be, under conditions effective to allow the formation of immunocomplexes.

These methods include methods for purifying wild type and/or mutant proteins, polypeptides and/or peptides as may be employed in purifying wild type and/or mutant proteins, polypeptides and/or peptides from patients' samples and/or for purifying recombinantly expressed wild type or mutant proteins, polypeptides and/or peptides. In these instances, the antibody removes the antigenic wild type and/or mutant protein, polypeptide and/or peptide component from a sample. The antibody will preferably be linked to a solid support, such as in the form of a column matrix, and the sample suspected of containing the wild type or mutant protein antigenic component will be applied to the immobilized antibody. The unwanted components will be washed from the column, leaving the antigen immunocomplexed to the immobilized antibody, which wild type or mutant protein antigen is then collected by removing the wild type or mutant protein and/or peptide from the column.

The immunobinding methods also include methods for detecting and quantifying the amount of a wild type or mutant protein reactive component in a sample and the detection and quantification of any immune complexes formed during the binding process. Here, one would obtain a sample suspected of comprising a wild type or mutant protein and/or peptide or suspected of comprising an *E. canis* organism, and contact the sample with an antibody against wild type or mutant, and then detect and quantify the amount of immune complexes formed under the specific conditions.

In terms of antigen detection, the biological sample analyzed may be any sample that is suspected of containing a wild type or mutant protein-specific antigen, such as a specimen, a homogenized tissue extract, a cell, separated and/or purified forms of any of the above wild type or mutant protein-containing compositions, or even any biological fluid that comes into contact with an *E. canis* organism upon infection.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any protein antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

The immunodetection methods of the present invention have evident utility in the diagnosis and prognosis of conditions such as various forms of hyperproliferative diseases, such as cancer, including leukemia, for example. Here, a biological and/or clinical sample suspected of containing a wild type or mutant protein, polypeptide, peptide and/or mutant is used. However, these embodiments also have applications to non-clinical samples, such as in the titering of antigen or antibody samples, for example in the selection of hybridomas.

H. ELISAs

As detailed above, immunoassays, in their most simple and/or direct sense, are binding assays. Certain preferred immunoassays are the various types of enzyme linked immunosorbent assays (ELISAs) and/or radioimmunoassays (RIA) known in the art.

Immunohistochemical detection using tissue sections is also particularly useful. However, it will be readily appreciated that detection is not limited to such techniques, and/or western blotting, dot blotting, FACS analyses, and/or the like may also be used.

In one exemplary ELISA, the antibodies of the invention are immobilized onto a selected surface exhibiting protein affinity, such as a well in a polystyrene microtiter plate. Then, a test composition suspected of containing the wild type and/or mutant protein antigen, such as a clinical sample, is added to the wells. After binding and/or washing to remove non-specifically bound immune complexes, the bound wild type and/or mutant protein antigen may be detected. Detection is generally achieved by the addition of another antibody that is linked to a detectable label. This type of ELISA is a simple "sandwich ELISA". Detection may also be achieved by the addition of a second antibody, followed by the addition of a third antibody that has binding affinity for the second antibody, with the third antibody being linked to a detectable label.

In another exemplary ELISA, the samples suspected of containing the wild type and/or mutant protein antigen are immobilized onto the well surface and/or then contacted with the antibodies of the invention. After binding and/or washing to remove non-specifically bound immune complexes, the bound antibodies are detected. Where the initial antibodies are linked to a detectable label, the immune complexes may be detected directly. Again, the immune complexes may be detected using a second antibody that has binding affinity for the first antibody, with the second antibody being linked to a detectable label.

Another ELISA in which the wild type and/or mutant proteins, polypeptides and/or peptides are immobilized, involves the use of antibody competition in the detection. In this ELISA, labeled antibodies against wild type or mutant protein are added to the wells, allowed to bind, and/or detected by means of their label. The amount of wild type or mutant protein antigen in an unknown sample is then determined by mixing the sample with the labeled antibodies against wild type and/or mutant before and/or during incubation with coated wells. The presence of wild type and/or mutant protein in the sample acts to reduce the amount of antibody against wild type or mutant protein available for binding to the well and thus reduces the ultimate signal. This is also appropriate for detecting antibodies against wild type or mutant protein in an unknown sample, where the unlabeled antibodies bind to the antigen-coated wells and also reduces the amount of antigen available to bind the labeled antibodies.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

I. Immunohistochemistry

The antibodies of the present invention may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in 70° C. isopentane; cutting the plastic capsule and/or removing the frozen cylinder of tissue; securing the tissue cylinder on a cryostat microtome chuck; and/or cutting 25-50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections.

J. Immunoelectron Microscopy

The antibodies of the present invention may also be used in conjunction with electron microscopy to identify intracellular tissue components. Briefly, an electron-dense label is conjugated directly or indirectly to the antibody. Examples of electron-dense labels according to the invention are ferritin and gold. The electron-dense label absorbs electrons and can be visualized by the electron microscope.

K. Immunodetection Kits

In still further embodiments, the present invention concerns immunodetection kits for use with the immunodetection methods described above. As the antibodies are generally used to detect wild type and/or mutant proteins, polypeptides and/or peptides, the antibodies will preferably be included in the kit. However, kits including both such components may be provided. The immunodetection kits will thus comprise, in suitable container means, a first antibody that binds to a wild type and/or mutant protein, polypeptide and/or peptide, and/or optionally, an immunodetection reagent and/or further optionally, a wild type and/or mutant protein, polypeptide and/or peptide.

In preferred embodiments, monoclonal antibodies will be used. In certain embodiments, the first antibody that binds to the wild type and/or mutant protein, polypeptide and/or peptide may be pre-bound to a solid support, such as a column matrix and/or well of a microtitre plate.

The immunodetection reagents of the kit may take any one of a variety of forms, including those detectable labels that are associated with and/or linked to the given antibody. Detectable labels that are associated with and/or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and/or all such labels may be employed in connection with the present invention.

The kits may further comprise a suitably aliquoted composition of the wild type and/or mutant protein, polypeptide and/or polypeptide, whether labeled and/or unlabeled, as may be used to prepare a standard curve for a detection assay. The kits may contain antibody-label conjugates either in fully conjugated form, in the form of intermediates, and/or as separate moieties to be conjugated by the user of the kit. The components of the kits may be packaged either in aqueous media and/or in lyophilized form.

The container means of the kits will be suitable housed and will generally include at least one vial, test tube, flask, bottle, syringe and/or other container means, into which the antibody may be placed, and/or preferably, suitably aliquoted. Where wild type and/or mutant gp19 protein, polypeptide and/or peptide, and/or a second and/or third binding ligand and/or additional component is provided, the kit will also generally contain a second, third and/or other additional container into which this ligand and/or component may be placed. The kits of the present invention will also typically include a means for containing the antibody, antigen, and/or any other reagent containers in close confinement for commercial sale. Such containers may include injection and/or blow-molded plastic containers into which the desired vials are retained.

VIII. Pharmaceutical Preparations

It is also contemplated that pharmaceutical compositions may be prepared using the novel compositions of the present invention. In such a case, the pharmaceutical composition comprises the novel active composition of the present invention and a pharmaceutically acceptable carrier. A person having ordinary skill in this art would readily be able to determine, without undue experimentation, the appropriate dosages and routes of administration of the active component of the present invention.

The phrase "pharmaceutically acceptable" refers to molecular entities and compositions that do not produce an allergic or similar untoward reaction when administered to a subject. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

In general, a pharmaceutical composition of the present invention may comprise an *E. canis* gp19 polypeptide, polynucleotide, or antibody and/or mixtures thereof A protein may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids such as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media, which can be employed, will be known to those of skill in the art in light of present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Pharmaceutical compositions of the present invention comprise an effective amount of one or more agents that target a polypeptide or the secretion thereof or additional agent dissolved or dispersed in a pharmaceutically acceptable carrier. The phrases "pharmaceutical," "pharmaceutically acceptable," or "pharmacologically acceptable" refers to molecular entities and compositions that do not produce an adverse, allergic or other untoward reaction when administered to an animal, such as, for example, a human, as appropriate. The preparation of a pharmaceutical composition that contains at least one agent that targets the polypeptide or the secretion thereof and/or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The invention may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g. aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof The invention may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the composition is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations that are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle that contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

IX. Exemplary Kits of the Invention

In particular embodiments of the invention, there is a kit housed in a suitable container. The kit may be suitable for diagnosis, treatment, and/or protection for an individual from *Ehrlichia*, such as *Ehrlichia canis*. In particular embodiments, the kit comprises in a suitable container an agent that targets an *E. canis* gp19 antigen. The agent may be an antibody, a small molecule, a polynucleotide, a polypeptide, a peptide, or a mixture thereof. The agent may be provided in the kit in a suitable form, such as sterile, lyophilized, or both, for example. In particular embodiments, the kit comprises an antibody against one or more of SEQ ID NO:13, SEQ ID NO:17 or SEQ ID NO:19 (for *E. canis*); and/or related proteins thereof. Other *E. canis* gp19-related immunogenic-related compositions (including polypeptides, peptides, or antibodies) not specifically presented herein may also be included.

The kit may further comprise one or more apparatuses for delivery of a composition to an individual in need thereof.

The apparatuses may include a syringe, eye dropper, needle, biopsy tool, scoopula, catheter, and so forth, for example.

In embodiments wherein the kit is employed for a diagnostic purpose, the kit may further provide one or more detection compositions and/or apparatuses for identifying an *E. canis* gp19 antigen. Such an embodiment may employ a detectable label, such as for an antibody, for example, and the label may be fluorescent, radioactive, chemiluminescent, or colorimetric, for example.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

Example 1

Exemplary Materials and Methods

Culture and Purification of Ehrlichiae.

*E. canis* (Jake, DJ, Demon, Louisiana, Florida, and Sao Paulo strains) and were propagated as previously described (McBride et al., 2001). Ehrlichiae were purified by size exclusion chromatography over SEPHACRYL® S-1000 (Amersham Biosciences, Piscataway, N.J.) as previously described (Rikihisa et al., 1992). The fractions containing bacteria were frozen and utilized as antigen and DNA sources.

Construction and Screening of the *E. canis* Genomic Library.

An *E. canis* Jake strain genomic library was constructed using a HpaII restriction digest and screened as previously described (McBride et al., 2001).

DNA Sequencing.

Library inserts, plasmids, and PCR products were sequenced with an ABI Prism 377XL DNA Sequencer (Perkin-Elmer Applied Biosystems, Foster City, Calif.) at the University of Texas Medical Branch Protein Chemistry Core Laboratory.

Glycoprotein Analysis.

Nucleic acid and amino acid alignments were performed with MegAlign (Lasergene v5.08, DNAstar, Madison, Wis.). The *E. canis* gp19 and *E. chaffeensis* VLPT protein sequences were evaluated for potential O-linked glycosylation and phosphorylation with the computational algorithms YinOYang 1.2 and NetOGlyc v3.1 (Julenius et al., 2005). Tandem Repeat Finder (Benson, 1999) was used to analyze the tandem repeats of the genes encoding *E. canis* gp19. Potential signal sequences were identified with the computational algorithm SignalP trained on gram-negative bacteria (Nielsen et al., 1997).

PCR Amplification of the *E. canis* gp19 Gene Fragments.

Oligonucleotide primers for the amplification of the *E. canis* gp19 gene fragments (gp19; gp19N-terminal, gp19N1, gp19N2, gp19N1-C, gp19C-terminal) were designed manually or by using Primer Select (Lasergene v5.08, DNAstar, Madison Wis.) (Table 2). *E. canis* gp19 fragments were amplified using the PCR Master mix (F. Hoffmann-La Roche Ltd, Basel, Switzerland) and *E. canis* (Jake strain) genomic DNA as template.

TABLE 2

Exemplary oligonucleotide primers for amplification of *E. canis* gp19 gene

| Recombinant Protein | Forward Primer | Sequence | Reverse Primer | Sequence | Amplicon Size |
|---|---|---|---|---|---|
| gp19 | P16N-F | 5'-CACGTTCAAAATCATGTTGA-3' (SEQ ID NO: 1) | P16C-R | 5'-CGCACAATCACAACAGTTGT-3 (SEQ ID NO: 7) | 405 bp |
| gp19N | P16N-F | 5'-CACGTTCAAAATCATGTTGA-3' (SEQ ID NO: 2) | P16N-R | 5'-GCATACTGGTCTTTCCT-3' (SEQ ID NO: 8) | 222 bp |
| gp19N1 | P16N-F | 5'-CACGTTCAAAATCATGTTGA-3' (SEQ ID NO: 3) | p19 132-R | 5'-AGATACTTCTTGTAACTCCATT-3' (SEQ ID NO: 9) | 126 bp |
| gp19N1-C | Small FOR | 5'-CATTTTACTGGTCCTACT-3' (SEQ ID NO: 4) | p19 132-R | 5'-AGATACTTCTTGTAACTCCATT-3' (SEQ ID NO: 10) | 72 bp |
| gp19N2 | p19 133-F | 5'-TCTATTGATAGTGTAGGATGC-3' (SEQ ID NO: 5) | P16N-R | 5'-GCATACTGGTCTTTCCT-3' (SEQ ID NO: 11) | 96 bp |
| gp19C | P16C-F | 5'-GCAGGTTTAGAGAGCTT-3' (SEQ ID NO: 6) | P16C-R | 5'-CGCACAATCACAACAGTTGT-3 (SEQ ID NO: 12) | 180 bp |

Cloning and Expression of Recombinant *E. canis* gp19.

Figure 1:
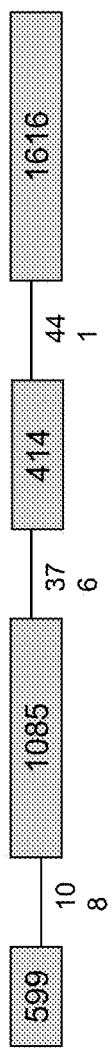
FIG. 1 provides a schematic of *E. canis* gp19 chromosomal location and adjacent genes (size in bp) and intergenic regions (size in bp). *E. chaffeensis* vlpt had the same adjacent genes.

The amplified PCR products were cloned directly into the pBAD/TOPO Thio Fusion® or pCR T7/NT TOPO expression vector (Invitrogen, Carlsbad, Calif.). *E. coli* (TOP10, Invitrogen) were transformed with the plasmid containing the *E. canis* gp19 gene fragments, and positive transformants were screened by PCR for the presence of the insert and its orientation and were sequenced to confirm the reading frame of the genes. Recombinant protein expression was induced with 0.2% arabinose (pBAD/TOPO Thio Fusion), or IPTG (pCR T7/NT) using the Overnight Express Autoinduction System 1 (Novagen, Madison, Wis.). Bacteria were pelleted (5,000×g for 20 min), resuspended in PBS, and recombinant proteins were purified under native conditions as previously described (Doyle et al., 2005).

Gel Electrophoresis and Western Immunoblotting.

Purified *E. canis* or *E. chaffeensis* whole cell lysates or recombinant proteins were separated by SDS-PAGE, transferred to nitrocellulose, and Western blots performed as previously described (McBride et al., 2003), except primary antibodies were diluted (1:500). Anti-*E. canis* or *E. chaffeensis* dog sera were derived from experimentally infected dogs (#2995 and #2551, respectively).

Carbohydrate Detection and Glycosyl Composition.

Glycan detection on the recombinant protein gp19 was performed with a DIG glycan detection kit (Roche, Indianapolis, Ind.) as previously described (McBride et al., 2000). The glycosyl composition was determined by alditol acetate analysis at the University of Georgia Complex Carbohydrate Research Center. The glycoprotein was hydrolyzed using 2 M trifluoroacetic acid (TFA; 2 h in sealed tube at 121° C.), reduced with NaBD4, and acetylated using acetic anhydride/TFA. The resulting alditol acetate was analyzed on a Hewlett Packard 5890 gas chromatograph interfaced to a 5970 mass selective detector (electron impact ionization mode), and separation was performed on a 30 m SUPELCO® 2330 bonded phase fused silica capillary column.

Mouse Immunization.

Five BALB/c mice (Jackson Laboratories, Bar Harbor, Me.) were immunized with the recombinant *E. canis* gp19 (Thio fusion; amino acids 4 to 137). Recombinant protein (100 μg) in 0.1 mL was mixed with an equal volume of Freund's complete adjuvant (Sigma, St. Louis, Mo.) for the first intraperitoneal injection and with Freund's incomplete adjuvant for the subsequent injections. The mice were given injections twice at two week intervals.

*E. canis* gp19 Synthetic Peptide Antibody Epitope.

A 24 amino acid peptide (N1-C; HFTGPTSFEVNLSEEEKMELQEVSS; SEQ ID NO:13) corresponding to the *E. canis* gp19 epitope-containing region was synthesized by Bio-Synthesis, Inc. (Lewisville, Tex.).

Enzyme-Linked Immunosorbent Assay (ELISA).

ELISA plates (NUNC-IMMUNO® Plates with MAXISORP® Surface, NUNC, Roskilde, Denmark) were coated with recombinant protein or peptide (1.25 μg/well, 100 μL) in phosphate buffered saline (PBS). Antigen was adsorbed to the ELISA plates overnight at 4° C. with gentle agitation and subsequently washed three times with 200 μL Tris buffered saline with TWEEN® 20 (0.2%) (polysorbate 20) (TBST), blocked with 3% BSA in TBST for 1 hr at room temperature with agitation and washed again. Convalescent anti-*E. canis* canine serum (1:4000) diluted in 3% BSA TBST was added to each well (100 μL) and incubated at room temperature for 1 h with gentle agitation. The plates were washed four times, and an alkaline phosphatase-labeled goat anti-dog IgG (H+L) secondary antibody (1:2500) (Kirkegaard & Perry Laboratories) in 3% BSA TBST was added and incubated for 1 hr. The plates were washed four times, and substrate (100 μL) (BluePhos, Kirkegaard & Perry Laboratories) was added to each well. The plates were incubated for 30 min in the dark with agitation, and color development was read on a microplate reader (VERSAMAX®, Molecular Devices, Sunnyvale, Calif.) at A650 and data analyzed by SOFTMAXPRO® v4.0 (Molecular Devices). Optical density readings of the bar graph represent the mean of two wells with the O.D. of the buffer-only wells subtracted. Periodate treatment of the recombinant gp19 was carried out for 20 min in 100 mM sodium acetate buffer with 100 mM sodium metaperiodate. Sham-treated control protein was incubated in the same buffers in the absence of periodate. The ELISA was carried out as described above for *E. canis* antigens, with the exception that the plate was blocked with milk diluent/blocking solution (Kirkegaard & Perry Laboratories, Gaithersburg, Md.).

Immunoelectron Microscopy.

Immunogold electron microscopy was performed as previously described (Doyle et al., 2005) except primary anti-*E. canis* gp19 antibody was diluted 1:10,000. Uninfected DH82 cells were reacted with anti-*E. canis* gp19 as a negative control.

Fluorescent Confocal Microscopy.

Antigen slides were prepared from DH82 cells infected with *E. canis* (Jake strain) as described previously (McBride et al., 2001). Monospecific rabbit serum against the recombinant *E. canis* disulfide bond formation protein (DsbA) (McBride et al., 2002) diluted 1:100 was added to each well (15 μL) and allowed to incubate for 30 min. Slides were washed, and mouse anti-gp19 (1:100 dilution) was added and incubated for 30 min. Alexa Fluor® 488 goat anti-rabbit IgG (H & L) secondary antibody (Molecular Probes, Eugene, Or.) diluted 1:100 was added and incubated for 30 min, followed by washing and subsequent addition and incubation of rhodamine-labeled goat anti-mouse IgG (H & L) secondary antibody (Kirkegaard & Perry Laboratories). Mounting medium (ProLong Gold, Molecular Probes) was added and the slides were viewed with an Olympus FV-1000 laser confocal microscope and Fluoview™ software.

PCR Amplification of *E. canis* gp19 from Geographically Dispersed Isolates.

DNA isolated from North American (Jake, Demon, DJ, Louisiana and Florida) isolates, South American (Brazil) isolate (Sao Paulo; kindly provided by Marcelo Labruna) and infected dog from Mexico (Yucatan; kindly provided by Carlos Perez) were used as template to amplify the entire gp19 gene using flanking primers (Forward-Ecanis p19 FOR, 5'-AAAATTAGTGTTGTGGTTATG-3' (SEQ ID NO:14) and reverse-Ecanis p19 REV, 5'-TTTTACGCTTGCTGAAT-3'; SEQ ID NO:15). The amplicons were cloned into a TA cloning vector (pCR 2.1, Invitrogen) and plasmids transformed into *E. coli* (TOP10). Plasmids containing gp19 were purified with plasmid purification kit (Roche) and sequenced.

Example 2

Molecular Identification of the *E. Canis* Gp19 Major Immunoreactive Protein Screening of an *E. canis* genomic expression library identified a clone that reacted strongly with antibody and contained a ~3-kb insert. This clone was partially sequenced (~900 bp) to reveal an incomplete ORF, which was aligned with the available *E. canis* genome sequence to fully identify the genes present within the 3 kb clone. The clone contained a complete 1086-bp gene encoding a riboflavin biosynthesis protein (RibD), and a downstream 414-bp ORF encoding a protein of 137 amino acids with a predicted mass of 15.8 kDa with unknown function. The protein had a 47 amino acid C-terminal region with >53% identity and ~60% overall homology to *E. chaffeensis* VLPT, a known immunoreactive protein; therefore this gene was considered for further investigation. The *E. canis* protein had substantial C-terminal region homology (60%) with *E. chaffeensis* VLPT, but it lacked the characteristic tandem repeats. The *E. canis* protein did have several predicted 0-glycan attachment sites and one amino acid (serine 44) that was a predicted Yin-Yang site (glycosylation/phosphorylation). Further analysis of the gene position in the chromosome revealed the same adjacent genes for the 414-bp *E. canis* gene and that of *E. chaffeensis* vlpt (FIG. 1).

Protein Characteristics.

Cysteine (14; 10.2%), serine and threonine (13; 9.5% combined), glutamate (13; 9.5%) and tyrosine (13; 9.5%) were the most frequently occurring amino acids in the *E. canis* gp19, accounting for more 38% of the entire amino acid content. Cysteine residues were not present in the first 50 amino acids, but the carboxyl-terminal region of the protein (last 28 amino acids) was dominated by cysteine and tyrosine (55%). Serine, threonine (7 each; 27% and glutamate residues (6; 23%) were the most frequently occurring amino acids in a small central region (STE-rich patch; 26 amino acids) and accounted for 50% of the amino acid content.

Conservation of *E. canis* Gp19.

*E. canis* gp19 was examined in geographically dispersed North American (Jake, DJ, Demon, Louisiana, and Florida) and South American (Brazil; Sao Paulo) isolates and was completely conserved. The gp19 sequence amplified from an *E. canis*-infected dog from Mexico (Yucatan) had a single nucleotide substitution (position 71) that resulted in a single amino acid change from glycine to aspartate.

Molecular Mass and Immunoreactivity.

Figure 2:
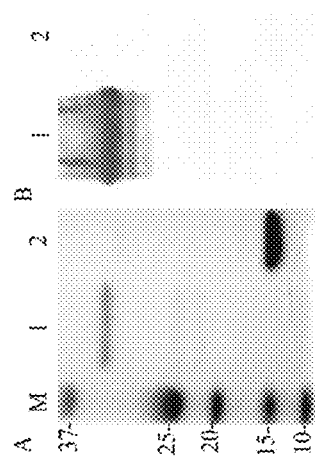
FIG. 2 relates to gp19 thiofusion protein. (Panel A) Molecular mass of *E. canis* gp19 pBAD thiofusion protein (~35 kDa) (lane 1) after sodium dodecyl sulfate polyacrylamide gel electrophoresis (SDS-PAGE); M-BioRad Precision molecular weight marker. (Panel B) Corresponding Western immunoblot of recombinant gp19 thiofusion protein (lane 1) and thioredoxin control protein (13-kDa) (lane 2) reacted with anti-*E. canis* dog serum (#2995).

The mass of the gp19 fusion recombinant protein was ~35 kDa, and was larger (~3 kDa) than the predicted (32 kDa) mass which included the fusion tags (13 kDa), but was consistent with the ~3 kDa larger than predicted (16 kDa) mass of the native gp19 (19-kDa) (FIG. 2A). Similarly, smaller fragments of the gp19 (N-terminal, N1 and N1c) expressed as recombinant fusion proteins had molecular masses larger (~6 kDa) (see FIG. 5 for orientation) than predicted by their amino acid sequences. The recombinant gp19 reacted strongly with serum from a dog (#2995) experimentally infected with *E. canis* (FIG. 2B).

Carbohydrate Detection.

Figure 3:
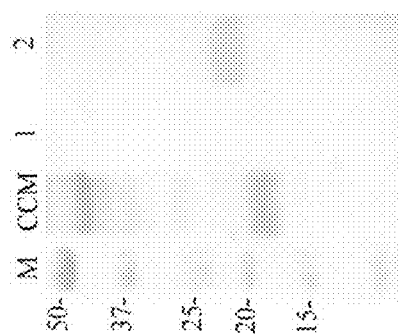
FIG. 3 shows carbohydrate detection of with *E. canis* gp19 (amino terminal fragment) (lane 2) and *E. canis* Dsb protein (lane 1; negative control). M=BioRad Precision Protein Standards; CCM=CandyCane glycoprotein molecular weight standards containing a mixture of glycosylated and non-glycosylated proteins (Glycosylated proteins, 42- and 18-kDa; non-glycosylated proteins, 29- and 14-kDa).
Figure 4:
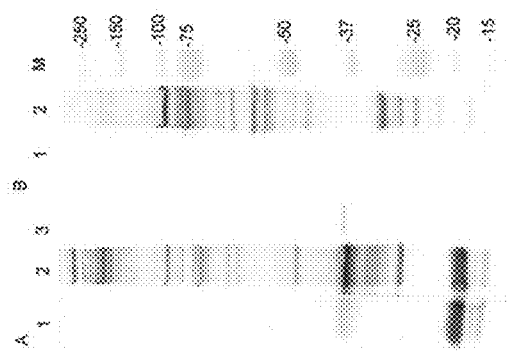
FIG. 4 shows westerns related to gp19. (Panel A) Western immunoblot of *E. canis* whole cell lysates probed with anti-*E. canis* gp19 serum (lane 1) and anti-*E. canis* dog serum (lane 2). Infected DH82 cell lysates probed with anti-*E. canis* dog serum (lane 3). (Panel B) *E. chaffeensis* whole cell lysates probed with anti-*E. canis* gp19 (lane 1) and anti-*E. chaffeensis* dog serum (lane 2).

Carbohydrate was detected on the recombinant gp19 (N-terminal, see FIG. 4 for orientation), which contained the STE-patch (FIG. 3). Furthermore, glycosyl composition analysis of the N-terminal fragment by the University of Georgia Complex Carbohydrate Research Center using alditol acetate analysis revealed the presence of glucose and xylose.

Identification of Native Gp19 and Species Specificity.

Anti-recombinant gp19 antisera reacted strongly with a 19 kDa protein in *E. canis* whole cell lysates, and this protein was similarly recognized by anti-*E. canis* dog serum (FIG. 4A). The anti-recombinant gp19 sera also reacted weakly with another well characterized *E. canis* glycoprotein, gp36, suggesting a minor cross reactivity between these two proteins. The anti-recombinant gp19 sera did not recognize antigens in *E. chaffeensis* whole cell lysates (FIG. 4B).

Single Major Epitope.

Epitope determinants of other glycoproteins have been determined including the *E. chaffeensis* gp47 and *E. canis* gp36 (Doyle et al., 2006). The *E. canis* gp19 is strongly recognized by antibody of infected dogs, and it elicits an early antibody response (McBride et al., 2003). In order to identify the epitope-containing region, *E. canis* gp19 gene fragments (N-terminal, C-terminal, N1, N2, N1C) (FIG. 5) were amplified with primers (Table 2) to create overlapping recombinant fusion proteins. The expressed gp19 fragments (N1, N2, N-terminal and C-terminal) exhibited larger (2- to 6-kDa) than predicted masses by SDS-PAGE (FIG. 4A). Antibody reacted strongly with the N-terminal recombinant fragment, but did not react with the C-terminal fragment indicating that an epitope was located in the N-terminal region of the protein (FIG. 5B). Further localization of the epitope containing region was determined with fragments N1 and N2. Antibody strong reacted with the N1 (42 amino acids), and N2 was weakly recognized (FIG. 5B). A region within N1 that had a high Ser/Thr/Glu content (N1C; 24 amino acids) consistent with other epitopes identified in other ehrlichial proteins reacted strongly with antibody consistent with that of the larger N1 fragment, demonstrating that a single major epitope was located in the 24 amino acid region of N1C.

Carbohydrate as an Epitope Determinant.

It was previously shown that carbohydrate is an important epitope determinant on major immunoreactive glycoproteins (Doyle et al., 2006). Carbohydrate was detected on the N-terminal region of the gp19, and the epitope localized to the STE-rich patch. Glycan attachment sites were also predicted within the STE-rich patch. To determine the role of carbohydrate determinants in antibody recognition, the immunoreactivity of recombinant N1C was compared with that of synthetic peptide. By ELISA, the synthetic peptide was substantially less immunoreactive with anti-*E. canis* dog serum (#2995) than the recombinant version (FIG. 6). Similarly, N1C treated with periodate to alter glycan structure was less immunoreactive than sham treated N1C protein (FIG. 6).

Cellular and Extracellular Localization of Gp19.

Several characterized ehrlichial glycoproteins are differentially expressed on dense-cored Ehrlichiae (gp120, gp36 and gp47). However, by immunoelectron microscopy the *E. canis* gp19 was observed within the cytoplasm of both reticulate and dense cored Ehrlichiae, but was also detected extracellularly on the morula fibrillar matrix and associated with the morula membrane (FIG. 7). These results were consistent with observations using confocal immunoflourescent microscopy using anti-gp19 (FIG. 8A) and anti-Dsb antibody (present on Ehrlichiae, but not extracellularly) (FIG. 8B), showing both Dsb and gp19 colocalizing on Ehrlichiae, and the border staining of the morula membrane by anti-gp19 only (merged) (FIG. 8C).

Nucleotide Sequence Accession Numbers.

The *Ehrlichia canis* gp19 gene sequences from *E. canis* gp19 (Jake, DJ, Demon, Louisiana, Florida, Sao Paulo and Mexico) isolate were deposited into GenBank® and assigned the following respective accession numbers: DQ858221, DQ858222, DQ858223, DQ858224, DQ858225, DQ860145, and DQ858226. All of these Accession numbers are represented in the polynucleotide sequence of SEQ ID NO:16 and the polypeptide sequence of SEQ ID NO:17 except the GenBank® accession number DQ858226, which is represented in the polynucleotide sequence of SEQ ID NO:18 and the polypeptide sequence of SEQ ID NO:19.

Example 3

Significance of the Present Invention

The kinetics of antibody responses to major immunoreactive antigens of *E. canis* during experimental infection has been well established in a previous study (McBride et al., 2003). Two *E. canis* antigens (37- and 19-kDa) were consistently recognized early in the acute immune response. In a more a recent study, the identification and molecular characterization of the 37-kDa protein (gp36), which is a differentially expressed glycoprotein on dense-cored Ehrlichiae and is secreted, was described (Doyle et al., 2006). As more major immunoreactive proteins have been molecularly characterized in *E. canis* and *E. chaffeensis*, it has become apparent that many exhibit high serine/threonine content, contain tandem repeats and are glycosylated (Doyle et al., 2006; McBride et al., 2000; Yu et al., 1997; Yu et al., 2000).

Although others have reported that orthologs of *E. chaffeensis* vlpt were not identified in related genomes (*E. canis* and *E. ruminantium*) (Hotopp et al., 2006), we provide evidence herein that the 19-kDa protein identified in this study is the ortholog of the previous described VLPT protein in *E. chaffeensis* (Sumner et al., 1999). The *E. chaffeensis* VLPT is immunoreactive, and has non-identical serine-rich tandem repeats. Although carbohydrate has not been reported on the *E. chaffeensis* VLPT, the protein also exhibits a mass double that predicted by its amino acid content, similar to other described ehrlichial glycoproteins (Sumner et al., 1999). Interestingly, the vlpt ortholog that we identified in *E. canis* in this study lacks the tandem repeats found in *E. chaffeensis* vlpt, but has a Ser/Thr/Glu-rich patch that is similar is size and composition to that of a single VLPT repeat unit. In addition, these genes share the same chromosomal location and have substantial amino acid homology (~60%) in the carboxyl-terminal region.

Another major immunoreactive protein (MAP2) related to *Anaplasma marginale* MSPS has been identified and molecularly characterized in *E. canis, E. chaffeensis* and *E. ruminantium* with a molecular mass (~21 kDa) similar to the gp19 identified in this study (Alleman et al., 2000; Alleman et al., 2001; Mahan et al., 1994). However, there is no amino acid homology between MAP2 and gp19, and thus, these proteins are molecularly and immunologically distinct. Unlike the gp19, the MAP2 appears to have a mass consistent with that predicted by its amino acid sequence and does not have any serine-rich domains. There is substantial homology among MAP2 orthologs in *Ehrlichia* spp., and cross reactions among heterologous MAP2 proteins have been reported (Knowles et al., 2003; Mahan et al., 1994). In contrast, antibodies generated to the *E. canis* gp19 were not cross reactive with *E. chaffeensis* VLPT, and therefore these proteins appear to be species-specific orthologs. Other notable differences between MAP2 and gp19 include a major serine-rich linear epitope of gp19 that is strongly recognized by antibodies by Western immunoblot, while antibodies to the MAP2 of *E. canis* and *E. chaffeensis* appear to directed primarily at a conformational epitope (Alleman et al., 2000; Alleman et al., 2001; Knowles et al., 2003). In a previous study it was suggested that the 19-kDa major immunoreactive protein that was identified may be MAP2 (McBride et al., 2003); however, data presented in this invention indicates that this protein is not MAP2, but rather gp19. Interestingly, only one major immunoreactive protein in the range of 15- to 25-kDa was identified in the previous study (McBride et al., 2003). The fact that antibodies to MAP2 were unable to be detected is likely related to the fact that conformational epitopes are dominant on both *E. canis* and *E. chaffeensis* MAP2 (Alleman et al., 2000; Alleman et al., 2001).

Consistent with numerous other major immunoreactive proteins that have been characterized, carbohydrate was present on the N-terminal region of the *E. canis* 19 kDa protein, and glucose and xylose were detected on this fragment. The presence of glucose and galactose as sugars attached to the *E. chaffeensis* gp120 and *E. canis* gp140 has been reported. Although the *E. canis* gp19 does not have serine-rich tandem repeats that appear to be locations of glycan attachment, it did contain a STE-rich patch within the N-terminal region, similar to the amino acid composition of tandem repeats found in other ehrlichial glycoproteins. Therefore, it is likely that O-linked glycans are attached to amino acids (serine/threonine) in this STE-rich patch. Furthermore, by using the prediction server YinOYang, serine residues within this region were identified as potential glycosylation/phosphorylation sites. Since this prediction server is trained on eukaryotic glycoproteins, identification of specific residues that are glycosylated may not be reliable; however, it is worth noting that there is a consistent positive correlation between our experimental data the prediction generated by this eukaryote-based prediction algorithm.

The amino acid composition of the *E. canis* gp19 consisted predominately of five amino acids, cysteine, glutamate, tyrosine, serine and threonine. Interestingly, these amino acids were concentrated in two specific domains, the epitope-containing region and carboxyl-terminal region. The high Ser/Thr/Glu content of the epitope containing region has been reported in other ehrlichial glycoproteins where epitopes have been mapped (Doyle et al., 2006), and high serine and threonine content has been found in other ehrlichial glycoproteins, particularly in tandem repeat regions (Doyle et al., 2006; Yu et al., 1997; Yu et al., 2000). The *E. chaffeensis* VLPT also contains tandems repeats with similar amino acid content. This similarity indicates that this region within the *E. canis* gp19 corresponds to the tandem repeat in *E. chaffeensis* VLPT. The addition and deletion of tandem repeats is considered a major source of change and instability in ehrlichial genomes (Frutos et al., 2006). The fact that the *E. canis* gp19 lacks tandem repeats, while *E. chaffeensis* VLPT has variable numbers is indicative of these genes being affected by this process.

Another novel feature of the gp19 is a carboxyl-terminal tail dominated by tyrosine and cysteine (55%). This carboxyl-terminal tail was also present on the *E. chaffeensis* VLPT downstream of the repeat region, indicating that it is an important conserved domain in these proteins. Overall, cysteine was present more than any other amino acid, and because of this, the gp19 is a member of a small group of proteins (n=36) with high cysteine content (Mavromatis et al., 2006). Cysteine is essential for intra- and inter-molecular disulfide bond formation, and its high content in the gp19 indicates that this protein has the potential to be linked with other cysteine containing proteins by disulfide bonds or that they are important for intramolecular bonding necessary for maintaining gp19 structure.

Tyrosine and serine are commonly phosphorylated. The high proportion of tyrosine residues in the carboxyl-terminal region of the gp19 suggests a high potential for this domain of the protein to be phosphorylated. This condition also raises the possibility that the gp19 is involved in protein signaling. The presence of phosphoproteins has been reported in *E. chaffeensis* (Singu et al., 2005), and more Ser/Thr/Tyr kinases and phosphoproteins are being identified in bacteria (Hinc et al., 2006; Levine et al., 2006; Madec et al., 2002; Obuchowski et al., 2000). Nevertheless, tyrosine residues in this C-terminal region were not identified as sites of phosphorylation by NetPhos, which is trained on eukaryote proteins. Therefore, further studies are performed to characterize the phosphorylation status of tyrosine residues how this relates to protein function, in specific embodiments of the invention.

A single major epitope was identified in the E. canis gp19 in the STE-rich domain. This epitope elicits an early antibody response in dogs experimentally infected with E. canis (McBride et al., 2003). Other epitopes that we have characterized within ehrlichial glycoproteins were mapped to serine-rich tandem repeats. Hence, finding a major epitope within the STE-region of the gp19 is consistent with previous studies, and demonstrates the importance of serine-rich regions and attached carbohydrate as immunodeterminants for Ehrlichia spp. Carbohydrate was detected on N-terminal region of the gp19 containing the STE-region. The recombinant gp19 epitope was more immunoreactive than the corresponding synthetic peptide, indicating that a post-translational modification was present on this epitope. In addition, treatment of the recombinant epitope-containing peptide with periodate reduced its immunoreactivity, further supporting a role for carbohydrate as an immunodeterminant. These findings are consistent with the previous demonstration of carbohydrate as an immunodeterminant on the epitopes that were mapped in the serine-rich tandem repeat regions of E. chaffeensis gp47 and E. canis gp36 (Doyle et al., 2006). Notably, this epitope appears to be species-specific, and the anti-gp19 antibody did not crossreact with E. chaffeensis antigens, similar to other species-specific major immunoreactive antigens that have been identified including the gp36 (Doyle et al., 2006; Yu et al., 1997; Yu et al., 2000). Therefore, use of sensitive species-specific immunodiagnostics utilizing the E. canis gp19 alone, or in combination with other antigens such as the gp36, are specific embodiments of the invention.

The E. canis gp19 was found on both reticulate and dense-cored cells and appeared to be localized predominantly in the cytoplasm of the Ehrlichiae. The localization of gp19 is in contrast to another E. canis glycoprotein (gp36) that we reported to be differentially expressed primarily on the surface of dense-cored cells (Doyle et al., 2006). However, similar to the gp36, the gp19 was also observed extracellularly in the morula fibrillar matrix, and associated with the morula membrane. The expression of gp19 on Ehrlichiae, fibrillar matrix and the morula membrane was further corroborated with immunofluorescence using dual staining with Dsb, which is not secreted and is present of both reticulate and dense cored organisms (McBride et al., 2002). Some small morulae appeared to have less gp19, suggesting that expression of gp19 becomes more predominant as the morula matures. The E. canis gp19 does not have an amino-terminal signal sequence; therefore, the export of this protein probably involves a sec-independent secretion system (Type 1 or Type III).

The E. canis gp19 was highly conserved in E. canis isolates examined from the United States, Mexico and Brazil. The conservation of major immunoreactive genes (p28, gp140, gp36) in geographically separated E. canis isolates has been consistently reported (Doyle et al., 2006; McBride et al., 2000; McBride et al., 1999; Ndip et al., 2005; Yu et al., 2000). This indicates that globally effective vaccines and reliable immunodiagnostics for E. canis based on major immunoreactive proteins such as the gp19 are feasible.

Example 4

Enhanced Sensitivity and Species-Specific Immunodiagnosis of Ehrlichia canis Infection by Enzyme-Linked Immunosorbent Assay with Conserved Immunoreactive Glycoproteins Gp36 and Gp19

Ehrlichia canis is the primary etiologic agent of canine monocytic ehrlichiosis (CME), a globally distributed and potentially fatal disease of dogs. The inventor previously reported the identification of two conserved major immunoreactive antigens, gp36 and gp19, the first proteins to elicit an E. canis-specific antibody response, and the gp200 and p28, which elicit strong antibody responses later in the acute infection. In the present invention, the sensitivity and specificity of five recombinant E. canis proteins were evaluated for immunodiagnosis of E. canis infection using an enzyme-linked immunosorbent assay (ELISA). Recombinant gp36, gp19 and gp200 polypeptides (N and C) exhibited 100% sensitivity and specificity compared with IFA (gold standard) in detecting antibodies in dogs that were naturally infected with E. canis. Furthermore, enhanced sensitivity of gp36 and gp19 compared to IFA was demonstrated with experimentally infected E. canis dogs, in which antibodies were detected as much as 2 weeks earlier, on day 14 post inoculation. In addition, the gp36 and gp19 were not cross-reactive with antibodies in sera from E. chaffeensis-infected dogs, and thus provided species-specific serologic discrimination between E. canis and E. chaffeensis infections. This is the first study to demonstrate improved detection capability with recombinant protein technology compared to the "gold standard" IFA, and may eliminate the remaining obstacles associated with immunodiagnosis of E. canis infections, including species-specific identification and lack of sensitivity associated with low antibody titers that occur early in the acute infection.

Materials and Methods

Experimental Animals.

Dogs and protocols used in experimental E. canis infections were previously described (McBride et al., 2003). For experimental E. chaffeensis infections, two one-year old healthy beagles were obtained from a commercial source and housed at the University of Texas Medical Branch Laboratory Animal Resources facility, which is accredited by the American Association for the Accreditation of Laboratory Animal Care. Prior to the study, dogs were demonstrated to lack abnormalities on physical examination and have no detectable antibodies to E. chaffeensis by IFA. The experimental protocol was approved by the Animal Care and Use Committee at the University of Texas Medical Branch.

E. chaffeensis and E. canis Inocula.

The tissue culture infectious dose (TCID) of the E. chaffeensis inoculum was determined by inoculation of DH82 monolayers plated in 24 well tissue culture plates with 10-fold dilutions ($10^{-1}$ to $10^{-5}$) of inoculum (0.2 ml) in MEM. The inoculum was incubated for 1 hr at 37° C. followed by the addition of 1 ml of growth medium. Seven days after inoculation, the TCID was determined by identification of E. chaffeensis in inoculated cells by IFA. The TCID of the E. canis inoculum was determined as previously described (Gaunt et al., 1996).

Experimental E. canis and E. chaffeensis Infection in Dogs.

Two dogs were experimentally infected with E. chaffeensis (Arkansas strain) propagated in a mouse embryo cell line as previously described (Chen et al., 1995). Infected cells from six T-150 flasks were harvested by centrifugation at 13,000×g, for 25 min after the cells were 80% infected. Two dogs received 4 ml of *E. chaffeensis* cell suspension intravenously immediately after preparation, and the TCID50 was determined retrospectively. Immune serum was collected four weeks after inoculation, and anti-*E. chaffeensis* and anti-*E. canis* antibody titers determined by IFA. Fifteen dogs were experimentally infected with *E. canis*, and serum collected at weekly intervals as previously described (McBride et al., 2003).

Dog Sera.

Serum samples from ill dogs exhibiting clinical signs or hematologic abnormalities consistent with CME were submitted to the Louisiana Veterinary Medical Diagnostic Laboratory (LAVMDL) from veterinarians statewide as previously described (McBride et al., 2001). Sera were screened by IFA (1:40) and separated into groups as *Ehrlichia* positive and negative sera. Sera from healthy dogs were obtained from one-year old healthy beagles from a commercial breeder (Marshall Farms, New York).

Cloning of the Genes of *E. canis* Recombinant Proteins.

The gp19 (nt 7-411), gp36 (nt 28-816), gp200N (nt 22-564) and gp200C (nt 3665-4188) and p28-3 gene (nt 82-695) were cloned into prokaryotic expression vectors as previously described (Doyle et al., 2006; McBride et al., 2006; McBride et al., 2001; McBride et al., 2000; Nethery et al., 2006). The primers were designed for in-frame insertion of amplicons into the pUni/V5-His-TOPO vector and recombined with pBAD Thio-E Echo acceptor vector (p28) (Invitrogen Corporation, Carlsbad, Calif.) or cloned directly into a pBAD/TOPO ThioFusion expression vector (gp19, gp36, gp200N and gp200C) (Invitrogen).

Expression and Purification of *E. canis* Recombinant Proteins.

The gp19, gp36, gp200N-terminal and gp200C-terminal recombinant proteins were expressed in *E. coli* (TOP10) after induction with 0.02% of arabinose for 2 hr. Bacteria (from 10 L of fermentation culture) were harvested by centrifugation at 5,000×g for 40 min and resuspended in PBS. Recombinant proteins (gp19, gp36, gp200N and gp200C) were purified under native conditions by lysing the bacteria resuspended in lysis buffer (PBS, 0.05% TRITON X100, 0.5 M NaCl, 1 mM PMSF and 5 mM imidazole) and disrupted using a French Press at 1100 psi in ice water and pelleting the insoluble material by centrifugation at 10,000×g for 1 hr. The clarified supernatant was loaded onto an equilibrated Ni-NTA column (50 ml column). The bound recombinant protein was washed with 15 column volumes of increasing concentrations of imidazole (4%, 8%, 20% and 100%) and eluted with 250 mM imidazole in lysis buffer. Recombinant p28 protein was purified under denaturing conditions by sonicating the pelleted bacteria resuspended in lysis buffer (50 mM Tris-HCl, 400 mM NaCl, 1 mM PMSF and 0.1% TRITON X100) at 50 W for 30 min (20 s on, 20 s off) in ice water and pelleting the insoluble material by centrifugation (10,000×g) for 30 min. The pellet was washed three times first with 2 M urea, then 4 M urea in lysis buffer and then with water stirring for 30 min at room temperature and pelleted (6000 g) for 30 min. The final wash was performed in 4 M urea plus 1% TRITON X100 and 0.1% deoxycholic acid with stirring for 1 hr at room temperature and pelleted by centrifugation (10,000×g, 45 min). The pellet was resuspended in sample buffer (4 M Urea, 6 M guanidine and 50 mM 2-mercaptoethanol) with overnight stirring at 4° C. and pelleted (10,000×g, 40 min). The clarified supernatant was loaded onto an equilibrated reversed phase column (26/10 XK, Amersham Biosciences), washed with buffer A (0.1% TFA) and eluted with 6 column volumes of increasing ratios (from 0% to 100% of buffer B) of buffer A and buffer B (0.1% TFA and 85% acetonitrile).

Enzyme-Linked Immunosorbent Assay (ELISA).

Antibody response to five *E. canis* recombinant proteins (gp36, gp19, p28, gp200N and gp200C) was evaluated by an enzyme-linked immunosorbant assay (ELISA). The ELISA protocol was optimized including choice of ELISA plate, protein concentrations, serum dilutions, and blocking buffers. The recombinant gp36 (0.3 µg/ml), gp19 (1.2 µg/ml), p28 (2.5 µg/ml), gp200N (1.4 µg/ml), gp200C (0.5 µg/ml), and thioredoxin control (2.5 µg/ml) were diluted in PBS and assay plate (Nunc-Immuno™ Plates with Polysorp™ Surface, NUNC, Roskilde, Denmark) wells were coated with 50 µl containing the recombinant proteins and incubated at room temperature for 2 hr or overnight at 4° C. The plates were washed 4 times with 200 µl of wash buffer (PBS and TWEEN® 20 (polysorbate), 0.05%), and blocked with 100 µl of blocking buffer (10% equine serum in PBS; HyClone Laboratories, Inc., Logan, Utah) and incubated for 1 hr at 37° C. Each primary antibody was diluted 1:250 in blocking buffer and 50 µl of the antibody was added to duplicate test wells containing antigen, a control well containing recombinant thioredoxin (negative control), and a blank well containing no antigen and incubated at room temperature for 1 hr. The plates were washed, and 50 µl of affinity-purified peroxidase labeled goat anti-dog IgG (H & L) (Kirkegaard & Perry Laboratories, Gaithersburg, Md.) diluted 1:1000 in blocking buffer was added to each well. The plates were incubated for 1 hr at room temperature and washed. Bound antibody was detected after addition of substrate (100 µl) (Sure Blue Reserve peroxidase substrate, Kirkegaard & Perry Laboratories). Plates were read on a tunable microplate reader (Molecular Devices, Sunnyvale. Calif.) at A630 after incubation at room temperature for 20 min. The absorbance of each sample was plotted as the optical density at 630 nm (OD630), and the background from the negative control well was subtracted from each corresponding sample to determine the final absorbance.

Gel Electrophoresis and Western Immunoblotting.

*E. canis* recombinant proteins were separated by sodium dodecyl-sulfate polyacrylamide gel electrophoresis (SDS-PAGE), transferred to nitrocellulose membranes, and Western immunoblots were performed as previously described (McBride et al., 2003).

IFA.

Antibody status of dogs experimentally infected with *E. canis*, clinically ill and naturally infected dogs was determined as previously described (McBride et al., 2003). Antibody status of healthy dogs and *E. chaffeensis* experimentally and naturally infected dogs was performed similarly with *E. canis* (Jake strain) and *E. chaffeensis* (Arkansas strain) antigen slides. Sera were assayed using two-fold dilutions in PBS starting at 1:64.

Comparison of Antibody Kinetics Against *E. canis* Recombinant Proteins by Western Blot and ELISA Antibodies to the *E. canis* major immunoreactive proteins develop differentially during the acute infection (McBride et al., 2003). The antibody response to *E. canis* recombinant proteins in three experimentally infected dogs was examined by ELISA and Western immunoblot to determine the correlation between the two immunoassays and to determine if kinetics previously observed with native *E. canis* lysates were reproduced with the recombinant proteins. Antibodies in sera from the three *E. canis*-infected dogs reacted earliest (day 14) with the recombinant gp36 by both Western immunoblot and ELISA, followed by the gp19 (day 21). The p28 and gp200 N- and C-terminal polypeptides exhibited similar detection sensitivity, reacting with antibodies later in the course of infection (days 28 to 35) approximately two weeks later than the gp36 (FIG. 9).

Analytical Sensitivity and Specificity of E. canis Recombinant Glycoprotein ELISA The current "gold standard" for immunodiagnosis is the indirect fluorescent antibody (IFA) test. This standard was used to determine the sensitivity and specificity of our recombinant protein ELISA. Antibodies against recombinant gp36, gp19, gp200N and gp200C were detected in all 29 positive IFA samples by ELISA from experimentally (range 1280 to >10,240) and naturally (antibody titers: 4, ≥3200; 4, 1600; 3, 800; and 2, 400) infected dogs with E. canis (Table 3). The recombinant proteins (gp36, gp19 and gp200 N- and C-terminal) exhibited 100% specificity compared to IFA with sera from healthy and ill dogs (Table 3). Conversely, recombinant p28 exhibited high levels of non-specific antibody binding (above negative control levels) with some dog sera and thus had a substantially lower specificity (60%).

TABLE 3

Analytical sensitivity and specificity of E. canis immunodiagnosis with recombinant proteins and IFA

| | Dogs (%) with detectable antibodies | | | | |
|---|---|---|---|---|---|
| | IFA | gp36 | gp19 | gp200N | gp200C |
| Experimentally Infected E. canis (n = 15)* | 15 (100) | 15 (100) | 15 (100) | 15 (100) | 15 (100) |
| Naturally Infected E. canis (n = 14) | 14 (100) | 14 (100) | 14 (100) | 14 (100) | 14 (100) |
| Total (n = 29) | 29 (100) | 29 (100) | 29 (100) | 29 (100) | 29 (100) |
| Clinically Healthy (n = 10) | 0 (0) | 0 (0) | 0 (0) | 0 (0) | 0 (0) |
| Clinically Ill (n = 26) | 0 (0) | 0 (0) | 0 (0) | 0 (0) | 0 (0) |
| Total (n = 36) | 0 (0) | 0 (0) | 0 (0) | 0 (0) | 0 (0) |
| Experimentally Infected E. chaffeensis (n = 2) | 2 (100) | 0 (0) | 0 (0) | 0 (0) | 0 (0) |
| Naturally Infected E. chaffeensis (n = 2)** | 2 (100) | 0 (0) | 0 (0) | 0 (0) | 0 (0) |

Earlier detection of anti-E. canis antibodies with recombinant glycoproteins. Dogs experimentally infected with E. canis (n=15), in which antibody response kinetics were defined (McBride et al., 2003), were used to determine detection sensitivity of IFA compared to recombinant proteins in ELISA. The experimentally infected dogs (1 exception) developed IgG antibodies to E. canis gp36 that could be detected by ELISA by 14 days post inoculation (dpi), and one third of these dogs (n=5) had antibodies that reacted with gp19 (Table 3). Conversely, none of the dogs had detectable IgG antibodies by IFA on 14 dpi (Table 3). Antibodies were detectable by IFA in only four dogs at 21 dpi. The IFA and recombinant glycoprotein ELISA sensitivity became comparable at 28 dpi, but complete agreement was not attained until 42 dpi (Table 4).

TABLE 4

Comparison of serologic detection sensitivity of E. canis infection by IFA and ELISA (gp36 and gp19) in experimentally infected dogs

| | Day 0 IFA gp36 gp19 | Day 7 IFA gp36 gp19 | Day 14 IFA gp36 gp19 | Day 21 IFA gp36 gp19 | Day 28 IFA gp36 gp19 | Day 35 IFA gp36 gp19 | Day 42 IFA gp36 gp19 |
|---|---|---|---|---|---|---|---|
| 32 | - - - | - - - | - + + | + + + | + + + | + + + | + + + |
| 33 | - - - | - - - | - + - | + + + | + + + | + + + | + + + |
| 34 | - - - | - - - | - + - | + + + | + + + | + + + | + + + |
| 35 | - - - | - - - | - + + | - + + | + + + | + + + | + + + |
| 37 | - - - | - - - | - + + | - + + | + + + | + + + | + + + |
| 41 | - - - | - - - | - + - | - + + | + + + | + + + | + + + |
| 43 | - - - | - - - | - + - | - + + | + + + | + + + | + + + |
| 44 | - - - | - - - | - + - | + + + | + + + | + + + | + + + |
| 45 | - - - | - - - | - + + | - + - | + + + | + + + | + + + |
| 46 | - - - | - - - | - + - | - + - | + + + | + + + | + + + |
| 48 | - - - | - - - | - + + | - + + | - - - | - + - | + + + |
| 51 | - - - | - - - | - - - | - - - | - + - | + + + | + + + |
| 52 | - - - | - - - | - + - | - + + | + + + | + + + | + + + |
| 54 | - - - | - - - | - + - | - + - | + + + | + + + | + + + |
| 59 | - - - | - - - | - + - | - + - | - + - | + + + | + + + |

Species-Specific Immunodiagnosis with Gp19 and Gp36.

Four dogs infected with E. chaffeensis (2-experimental and 2-natural) were IFA positive to E. canis antigen, but did not react with the E. canis recombinant proteins (gp36, gp19 and gp200). The anti-E. chaffeensis antibody titers in sera from dogs experimentally infected with E. chaffeensis were ≥1280. The anti-E. chaffeensis IFA antibody titers of the dogs naturally infected with E. chaffeensis were 1:400 and 1:800 to homologous antigen (1:64 to E. canis).

Significance of the Present Embodiment

Early diagnosis of CME in the acute stage of infection followed by treatment with doxycycline ensures the best prognosis. Detection of E. canis antibodies by IFA is currently the most widely used method for diagnosis of CME and is considered the "gold standard" (Waner et al., 2001). However, IFA is routinely performed in large reference diagnostic laboratories and is not useful as a point-of-care diagnostic or screening test because requires a high level of technical experience, is subject to inter- and intralaboratory variation and misinterpretation, and requires expensive fluorescent microscopy equipment. Furthermore, the IFA uses E. canis-infected cells that are not well defined and that contain antigens (heat shock and p28/p30) capable of reacting with antibodies generated against other genus members (E. chaffeensis and E. ewingii) and organisms from other genera (Neorickettsia) (corner et al., 1999). Thus, the possibility of multiple tick-borne infections in dogs complicates serological diagnosis by IFA (Kordick et al., 1999). Currently, point-of-care diagnostic tests (Snap 3Dx, IDEXX Laboratories; Dip-S-Tick, PanBio InDx; Immunocomb, Biogal) that are commercially available utilize whole cell antigen or synthetic or recombinant proteins/peptides from two major outer membrane proteins (p30 and p30-1). The Snap 3Dx assay appears to be one of the most widely used tests, but two recent studies have concluded that sensitivity appears to be substantially less than IFA (Belanger et al., 2002; Harms et al., 2002), a problem that is more pronounced with sera containing low (<320) antibody titers (Harrus et al., 2002; O'Connor et al., 2006). Furthermore, all of the commercially available assays are unable to differentiate between various *Ehrlichia* spp. that are known to cause infections in dogs. Hence, immunodiagnostics capable of providing better sensitivity, particularly during early acute infection, and the ability to differentiate the specific agent responsible for the infection; utilizing a well characterized and consistently reproducible recombinant or synthetic antigen are needed, but unavailable.

The recent molecular identification of several distinct but conserved major immunoreactive proteins of *E. canis* including gp36, gp19, gp200 and p28/30 has created new opportunities for substantial improvements in serologic diagnosis of CME (Doyle et al., 2006; McBride et al., 2003; McBride et al., 2001; McBride et al., 1999; Ohashi et al., 1998). The inventor has previously reported that the *E. canis* gp36, gp19 and gp200 are molecularly and immunologically distinct from the respective orthologs in *E. chaffeensis* (gp47, VLPT and gp200), and that two of these characterized proteins (gp36 and gp19) are the first to elicit an antibody response in *E. canis*-infected dogs (McBride et al., 2003). In addition, these proteins are conserved among geographically dispersed *E. canis* strains (Doyle et al., 2006; McBride et al., 2006; McBride et al., 2000; McBride et al., 1999). Therefore, these antigens have a high potential to facilitate the development of ultrasensitive and highly specific new generation immunodiagnostics for detection of *E. canis* infection. It was considered that in certain embodiments these proteins would provide increased sensitivity over whole cell antigen (IFA) for detecting antibodies early in the infection. In this invention, it was demonstrated that two recombinant *E. canis* proteins (gp36 and gp19) used in an ELISA format provided enhanced sensitivity compared to IFA for detecting antibodies during the early immune response and were highly specific for *E. canis*.

The molecularly characterized recombinant proteins (gp36, gp19, p28/30 and gp200) reacted with antibody from infected canine sera with kinetics similar to that reported with corresponding proteins in native *E. canis* lysates (McBride et al., 2003) in two immunoassay formats (ELISA and membrane) that are commonly used for point-of-care diagnostic tests. These results confirm that the recombinant proteins are suitable surrogates for native ehrlichial proteins and react similarly with antibodies generated during an infection. Furthermore, consistent results obtained by two immunoassay formats indicate that these proteins could provide consistent sensitivity regardless of the assay format utilized. In this particular study, Western immunoblotting provided similar results as compared to the ELISA, but results can be laboratory-dependent, and this technique is laborious, time consuming and not well suited for point-of-care tests.

The analytical sensitivity of the *E. canis* recombinant proteins completely correlated with the IFA using sera from dogs with natural and experimental infections. The inventors previously reported 100% sensitivity with *E. canis* gp200-N(P43), and those results were confirmed in this study (McBride et al., 2001). However, it was recently identified that there are five major epitopes within the gp200 protein (Nethery et al., 2006). The gp200-N (P43) contains a single major epitope and carboxy-terminal region, gp200-C, contains two major antibody epitopes (Nethery et al., 2006). The antibody response to both gp200 recombinant proteins developed later than the gp36 and gp19, but they reacted strongly with antibody in late acute phase serum from experimental dogs. These findings were consistent with previous investigations in which there was observed a strong late acute phase antibody response to the gp200 (McBride et al., 2003; McBride et al., 2001). Antibody to the *E. canis* P28 also developed later in the late acute phase immune response. It was previously reported similar antibody response kinetics that were consistent with both native and recombinant P28 (McBride et al., 2003). Some nonspecific responses to P28 were observed in the ELISA format, but this is due to other contaminating proteins, in specific embodiments. The P28 is very insoluble thus producing a highly purified recombinant protein is very difficult to achieve. Nevertheless, results obtained by Western immunoblotting in this study and other studies suggest that highly purified p28/p30 is a specific immunodiagnostic antigen (Belanger et al., 2002; McBride et al., 2003; McBride et al., 2001).

The first detectable antibodies to *E. canis* are directed at the gp36 and gp19 (Doyle et al., 2006; McBride et al., 2003). All of the *E. canis* recombinant proteins provided sensitivity similar to IFA in naturally infected dogs; however, in the experimentally infected group of dogs where the kinetics of the antibody response could be accurately determined, the gp36 and gp19 detected antibodies 7 to 14 days earlier than IFA or ELISA using the gp200 and p28. To our knowledge, this is the first demonstration that species-specific *E. canis* proteins are more sensitive than whole cell antigen for detection of low antibody levels produced during early acute ehrlichial infections. Many *E. canis* proteins may be suitable for detecting late acute phase antibodies, and sensitivities of specific proteins appear to be related to the disease phase. The sensitivity of *E. canis* antigens such as p28/p30, gp200 and MAP2 for detecting antibodies appears to be best in a later disease phase when sera contain medium to high levels of antibody. However, sera with low antibody levels, such as those obtained early in the infection, pose more difficulties with these recombinant antigens and whole cell antigen (Harms et al., 2002; O'Connor et al., 2006). This situation may be particularly relevant to sera collected from dogs early in the infection when antibody levels are low, and when an accurate diagnosis can be most challenging serologically.

The gp36 and gp19 have species-specific serine-rich major epitopes that have been identified and molecularly characterized (Doyle et al., 2006; McBride et al., 2006). Likewise, the *E. canis* and *E. chaffeensis* gp200 orthologs are antigenically distinct and have epitopes that have been molecularly characterized (McBride et al., 2003; McBride et al., 2001; Nethery et al., 2006). The major epitopes on gp36, gp19, and gp200 appear to have carbohydrate immunodeterminants that contribute to the immunoreactivity of the epitopes (Doyle et al., 2006; McBride et al., 2006; Nethery et al., 2006). These major immunoreactive antigens can discriminate serologically between *E. canis* and the most closely related organism, *E. chaffeensis*, and will enable the development of highly specific assays capable of discrimination of the specific infecting agent. Another major immunoreactive antigen (gp120) of *E. chaffeensis* capable of sensitive species-specific discrimination has also been reported (Yu et al., 1996; Yu et al., 1997; Yu et al., 1999). Thus, highly defined recombinant antigens that include the major epitopes of the *E. canis* gp36 and/or gp19 and *E. chaffeensis* gp120 could be utilized in the same assay for specific diagnosis of *E. canis* and *E. chaffeensis* infections.

The reliability of serologic diagnosis of infections with recombinant or synthetic antigens depends on the lack of antigenic variability of the antigen that is selected. In the case of *E. canis*, many of the major immunoreactive antigens, including gp36, gp19, gp200 and p28 that have the potential to be utilized for serodiagnosis, are highly conserved in geographically distinct isolates (Doyle et al., 2006; McBride et al., 2006; McBride et al., 2000; McBride et al., 1999; Yu et al., 2000). Conversely, *E. chaffeensis* exhibits more diversity among different isolates, but the antibody epitope of the gp120 appears to be well conserved (Chen et al., 1997; Doyle et al., 2006; Reddy and Streck, 2000; Doyle et al., 2006; Yu et al., 1997; Yu et al., 2000). Moreover, differential expression of the major outer membrane proteins (p28/p30), which have antigenically distinct hypervariable regions that contain antibody epitopes (Barnewall et al., 1999; Li et al., 2002; Li et al., 2002; McBride et al., 1999; Ohashi et al., 1998; Ohashi et al., 1998; Unver et al., 2002; Yu et al., 2000) may also contribute to variations in serologic responses to *E. canis* and *E. chaffeensis*. Thus, it was concluded that antigens such as the gp36 and gp19 that are highly conserved single gene proteins that minimize or eliminate potential for serologic variability have the best potential for development of globally useful ultrasensitive and species-specific immunodiagnostics that overcome these obstacles associated with CME serodiagnosis.

Example 5

Vaccines of the Invention

In particular aspects of the invention, the immunogenic compositions of the present invention are suitable as a vaccine, such as a subunit vaccine. In other aspects of the invention, the immunogenic compositions are referred to as immunoprotective.

Specifically, one or more compositions of the invention, such as those comprising an *E. canis* gp19 epitope, for example, are administered to a mammal, such as a human, canine, bovine, or equine animal, for example. Serum from the mammal may be assayed for an immune response, such as by detecting antibodies in the serum. The mammal is then subjected to subsequent challenge with the pathogenic organism, such as the *E. canis* organism, or another appropriate composition, and immunoprotection is determined. Controls may be employed, such as immunization with, for example, a mutated epitope or an epitope that does not comprise a carbohydrate moiety. Complete or partial protection against the subsequent challenge demonstrates the immunoprotective nature of the composition, and the composition is a vaccine. Partial protection may be defined as protecting from developing or delaying from developing at least one symptom of the infection or protecting from at least one symptom becoming worse.

REFERENCES

All patents and publications mentioned in the specification are indicative of the level of those skilled in the art to which the invention pertains. All patents and publications are herein incorporated by reference to the same extent as if each individual publication was specifically and individually indicated to be incorporated by reference.

Patents and Patent Applications

U.S. Pat. No. 5,440,013
U.S. Pat. No. 5,618,914
U.S. Pat. No. 5,670,155
U.S. Pat. No. 5,446,128
U.S. Pat. No. 5,710,245
U.S. Pat. No. 5,840,833
U.S. Pat. No. 5,859,184
U.S. Pat. No. 5,929,237
U.S. Pat. No. 5,475,085
U.S. Pat. No. 5,672,681
U.S. Pat. No. 5,674,976
U.S. Pat. No. 4,554,101

Publications

Alleman, A. R., A. F. Barbet, M. V. Bowie, H. L. Sorenson, S. J. Wong, and M. Belanger. 2000. Expression of a gene encoding the major antigenic protein 2 homolog of *Ehrlichia chaffeensis* and potential application for serodiagnosis. J. Clin. Microbiol. 38:3705-3709.

Alleman, A. R., L. J. McSherry, A. F. Barbet, E. B. Breitschwerdt, H. L. Sorenson, M. V. Bowie, and M. Belanger. 2001. Recombinant major antigenic protein 2 of *Ehrlichia canis*: a potential diagnostic tool. J. Clin. Microbiol. 39:2494-2499.

Barnewall, R. E., N. Ohashi, and Y. Rikihisa. 1999. *Ehrlichia chaffeensis* and *E. sennetsu*, but not the human granulocytic ehrlichiosis agent, colocalize with transferrin receptor and up-regulate transferrin receptor mRNA by activating iron-responsive protein 1. Infect. Immun. 67:2258-2265.

Belanger, M., H. L. Sorenson, M. K. France, M. V. Bowie, A. F. Barbet, E. B. Breitschwerdt, and A. R. Alleman. 2002. Comparison of serological detection methods for diagnosis of *Ehrlichia canis* infections in dogs. J Clin Microbiol. 40:3506-3508.

Benson, G. 1999. Tandem repeats finder: a program to analyze DNA sequences. Nucleic Acids Res. 27:573-580.

Breitschwerdt, E. B., B. C. Hegarty, and S. I. Hancock. 1998. Sequential evaluation of dogs naturally infected with *Ehrlichia canis, Ehrlichia chaffeensis, Ehrlichia equi, Ehrlichia ewingii*, or *Bartonella vinsonii*. J. Clin. Microbiol. 36:2645-2651.

Bzymek, M. and S. T. Lovett. 2001. Instability of repetitive DNA sequences: the role of replication in multiple mechanisms. Proc. Natl. Acad. Sci. U.S.A 98:8319-8325.

Chen, S. M., V. L. Popov, H. M. Feng, J. Wen, and D. H. Walker. 1995. Cultivation of *Ehrlichia chaffeensis* in mouse embryo, Vero, BGM, and L929 cells and study of *Ehrlichia*-induced cytopathic effect and plaque formation. Infect. Immun. 63:647-655.

Chen, S. M., X. J. Yu, V. L. Popov, E. L. Westerman, F. G. Hamilton, and D. H. Walker. 1997. Genetic and antigenic diversity of *Ehrlichia chaffeensis*: comparative analysis of a novel human strain from Oklahoma and previously isolated strains. J. Infect. Dis. 175:856-863.

Codner, E. C. and L. L. Farris-Smith. 1986. Characterization of the subclinical phase of ehrlichiosis in dogs. J. Am. Vet. Med. Assoc. 189:47-50.

Collins, N. E., J. Liebenberg, E. P. de Villiers, K. A. Brayton, E. Louw, A. Pretorius, F. E. Faber, H. H. van, A. Josemans, K. M. van, H. C. Steyn, M. F. van Strijp, E. Zweygarth, F. Jongejan, J. C. Maillard, D. Berthier, M. Botha, F. Joubert, C. H. Corton, N. R. Thomson, M. T. Allsopp, and B. A. Allsopp. 2005. The genome of the heartwater agent *Ehrlichia ruminantium* contains multiple tandem repeats of actively variable copy number. Proc. Natl. Acad. Sci. U.S.A 102:838-843.

Comer, J. A., W. L. Nicholson, J. G. Olson, and J. E. Childs. 1999. Serologic testing for human granulocytic ehrlichiosis at a national referral center. J. Clin. Microbiol. 37:558-564.

Cowell, R. L., R. D. Tyler, K. D. Clinkenbeard, and J. H. Meinkoth. 1988. Ehrlichiosis and polyarthritis in three dogs. J. Am. Vet. Med. Assoc. 192:1093-1095.

Dawson, J. E. and S. A. Ewing. 1992. Susceptibility of dogs to infection with *Ehrlichia chaffeensis*, causative agent of human ehrlichiosis. Am. J Vet. Res. 53:1322-1327.

Dawson, J. E., K. L. Biggie, C. K. Warner, K. Cookson, S. Jenkins, J. F. Levine, and J. G. Olson. 1996. Polymerase chain reaction evidence of *Ehrlichia chaffeensis*, an etiologic agent of human ehrlichiosis, in dogs from southeast Virginia. Am. J. Vet. Res. 57:1175-1179.

Doyle, C. K., A. M. Cardenas, D. M. Aguiar, M. B. Labruna, L. M. Ndip, X. J. Yu, and McBride J. W. 2006. Molecular characterization of *E. canis* gp36 and *E. chaffeensis* gp47 tandem repeats among different geographic locations. Ann. N. Y. Acad. Sci. 1063.

Doyle, C. K., K. A. Nethery, V. L. Popov, and J. W. McBride. 2006. Differentially expressed and secreted major immunoreactive protein orthologs of *Ehrlichia canis* and *E. chaffeensis* elicit early antibody responses to epitopes on glycosylated tandem repeats. Infect. Immun. 74:711-720.

Doyle, C. K., M. B. Labruna, E. B. Breitschwerdt, Y. W. Tang, R. E. Corstvet, B. C. Hegarty, K. C. Bloch, P. Li, D. H. Walker, and J. W. McBride. 2005. Detection of medically important *Ehrlichia* spp. by quantitative multicolor Taqman real-time PCR of the dsb gene. J. Mol. Diagn. 10:504-510.

Doyle, C. K., X. Zhang, V. L. Popov, and J. W. McBride. 2005. An immunoreactive 38-kilodalton protein of *Ehrlichia canis* shares structural homology and iron-binding capacity with the ferric ion-binding protein family. Infect. Immun. 73:62-69.

Dunning Hotopp, J. C., M. Lin, R. Madupu, J. Crabtree, S. V. Angiuoli, J. Eisen, R. Seshadri, Q. Ren, M. Wu, T. R. Utterback, S. Smith, M. Lewis, H. Khouri, C. Zhang, H. Niu, Q. Lin, N. Ohashi, N. Zhi, W. Nelson, L. M. Brinkac, R. J. Dodson, M. J. Rosovitz, J. Sundaram, S. C. Daugherty, T. Davidsen, A. S. Durkin, M. Gwinn, D. H. Haft, J. D. Selengut, S. A. Sullivan, N. Zafar, L. Zhou, F. Benahmed, H. Forberger, R. Halpin, S. Mulligan, J. Robinson, O. White, Y. Rikihisa, and H. Tettelin. 2006. Comparative genomics of emerging human ehrlichiosis agents. PLoS Genet. 2:e21.

Frutos, R., A. Viari, C. Ferraz, A. Morgat, S. Eychenie, Y. Kandassamy, I. Chantal, A. Bensaid, E. Coissac, N. Vachiery, J. Demaille, and D. Martinez. 2006. Comparative genomic analysis of three strains of *Ehrlichia ruminantium* reveals an active process of genome size plasticity. J Bacteriol 188:2533-2542.

Gaunt, S. D., R. E. Corstvet, C. M. Berry, and B. Brennan. 1996. Isolation of *Ehrlichia canis* from dogs following subcutaneous inoculation. J. Clin. Microbiol. 34:1429-1432.

Goldman, E. E., E. B. Breitschwerdt, C. B. Grindem, B. C. Hegarty, J. J. Walls, and J. S. Dumler. 1998. Granulocytic ehrlichiosis in dogs from North Carolina and Virginia. J Vet Intern Med 12:61-70.

Harms, S., A. R. Alleman, H. Bark, S. M. Mahan, and T. Waner. 2002. Comparison of three enzyme-linked immunosorbant assays with the indirect immunofluorescent antibody test for the diagnosis of canine infection with *Ehrlichia canis*. Vet. Microbiol. 86:361-368.

Hinc, K., K. Nagorska, A. Iwanicki, G. Wegrzyn, S. J. Seror, and M. Obuchowski. 2006. Expression of genes coding for GerA and GerK spore germination receptors is dependent on the protein phosphatase PrpE. J Bacteriol 188: 4373-4383.

Johannesson et al., 1999, "Bicyclic tripeptide mimetics with reverse turn inducing properties." J. Med. Chem. 42:601-608.

Julenius, K., A. Molgaard, R. Gupta, and S. Brunak. 2005. Prediction, conservation analysis, and structural characterization of mammalian mucin-type O-glycosylation sites. Glycobiology 15:153-164.

Knowles, T. T., A. R. Alleman, H. L. Sorenson, D. C. Marciano, E. B. Breitschwerdt, S. Harms, A. F. Barbet, and M. Belanger. 2003. Characterization of the major antigenic protein 2 of *Ehrlichia canis* and *Ehrlichia chaffeensis* and its application for serodiagnosis of ehrlichiosis. Clin. Diagn. Lab Immunol. 10:520-524.

Kordick, S. K., E. B. Breitschwerdt, B. C. Hegarty, K. L. Southwick, C. M. Colitz, S. I. Hancock, J. M. Bradley, R. Rumbough, J. T. Mcpherson, and J. N. MacCormack. 1999. Coinfection with multiple tick-borne pathogens in a Walker hound kennel in North Carolina. J. Clin. Microbiol. 37:2631-2638.

Kuehn, N. F. and S. D. Gaunt. 1985. Clinical and hematologic findings in canine ehrlichiosis. J. Am. Vet. Med. Assoc. 186:355-358.

Levine, A., F. Vannier, C. Absalon, L. Kuhn, P. Jackson, E. Scrivener, V. Labas, J. Vinh, P. Courtney, J. Garin, and S. J. Seror. 2006. Analysis of the dynamic *Bacillus subtilis* Ser/Thr/Tyr phosphoproteome implicated in a wide variety of cellular processes. Proteomics. 6:2157-2173.

Li, J. S., E. Yager, M. Reilly, C. Freeman, G. R. Reddy, A. A. Reilly, F. K. Chu, and G. M. Winslow. 2001. Outer membrane protein-specific monoclonal antibodies protect SCID mice from fatal infection by the obligate intracellular bacterial pathogen *Ehrlichia chaffeensis*. J. Immunol. 166:1855-1862.

Li, J. S., F. Chu, A. Reilly, and G. M. Winslow. 2002. Antibodies highly effective in SCID mice during infection by the intracellular bacterium *Ehrlichia chaffeensis* are of picomolar affinity and exhibit preferential epitope and isotype utilization. J. Immunol. 169:1419-1425.

Madec, E., A. Laszkiewicz, A. Iwanicki, M. Obuchowski, and S. Seror. 2002. Characterization of a membrane-linked Ser/Thr protein kinase in *Bacillus subtilis*, implicated in developmental processes. Mol. Microbiol. 46:571-586.

Mahan, S. M., T. C. McGuire, S. M. Semu, M. V. Bowie, F. Jongejan, F. R. Rurangirwa, and A. F. Barbet. 1994. Molecular cloning of a gene encoding the immunogenic 21 kDa protein of *Cowdria ruminantium*. Microbiol. 140 (Pt 8):2135-2142.

Mavromatis, K., C. K. Doyle, A. Lykidis, N. Ivanova, M. P. Francino, P. Chain, M. Shin, S. Malfatti, F. Larimer, A. Copeland, J. C. Detter, M. Land, P. M. Richardson, X. J. Yu, D. H. Walker, J. W. McBride, and N. C. Kyrpides. 2006. The genome of the obligately intracellular bacterium *Ehrlichia*

*canis* reveals themes of complex membrane structure and immune evasion strategies. J Bacteriol 188:4015-4023.

McBride J. W., C. K. Doyle, X. F. Zhang, A. M. Cardenas, V. L. Popov, K. A. Nethery, and M. E. Woods. 2006. *Ehrlichia canis* 19-kDa glycoprotein ortholog of *E. chaffeensis* variable length PCR target contains a single serine-rich epitope defined by a carbohydrate immunodetermiant. Infect. Immun.

McBride J W, R. E. Corstvet, S. D. Gaunt, C. Boudreaux, T. Guedry, and D. H. Walker. 2003. Kinetics of antibody response to *Ehrlichia canis* immunoreactive proteins. Infect. Immun. 71:2516-2524.

McBride J W, R. E. Corstvet, S. D. Gaunt, C. Boudreaux, T. Guedry, and D. H. Walker. 2003. Kinetics of antibody response to *Ehrlichia canis* immunoreactive proteins. Infect. Immun. 71:2516-2524.

McBride, J. W., J. E. Comer, and D. H. Walker. 2003. Novel immunoreactive glycoprotein orthologs of *Ehrlichia* spp. Ann. N. Y. Acad. Sci. 990:678-684.

McBride, J. W., L. M. Ndip, V. L. Popov, and D. H. Walker. 2002. Identification and functional analysis of an immunoreactive DsbA-like thio-disulfide oxidoreductase of *Ehrlichia* spp. Infect. Immun. 70:2700-2703.

McBride, J. W., R. E. Corstvet, E. B. Breitschwerdt, and D. H. Walker. 2001. Immunodiagnosis of *Ehrlichia canis* infection with recombinant proteins. J. Clin. Microbiol. 39:315-322.

McBride, J. W., R. E. Corstvet, E. B. Breitschwerdt, and D. H. Walker. 2001. Immunodiagnosis of *Ehrlichia canis* infection with recombinant proteins. J. Clin. Microbiol. 39:315-322.

McBride, J. W., X. J. Yu, and D. H. Walker. 1999. Molecular cloning of the gene for a conserved major immunoreactive 28-kilodalton protein of *Ehrlichia canis*: a potential serodiagnostic antigen. Clin. Diag. Lab. Immunol. 6:392-399.

McBride, J. W., X. J. Yu, and D. H. Walker. 2000. Glycosylation of homologous immunodominant proteins of *Ehrlichia chaffeensis* and *E. canis*. Infect. Immun. 68:13-18.

McBride, J. W., X. Yu, and D. H. Walker. 2000. A conserved, transcriptionally active p28 multigene locus of *Ehrlichia canis*. Gene 254:245-252.

Ndip, L. M., R. N. Ndip, S. N. Esemu, V. L. Dickmu, E. B. Fokam, D. H. Walker, and J. W. McBride. 2005. ehrlichial infection in Cameroonian canines by *Ehrlichia canis* and *Ehrlichia ewingii*. Vet. Microbiol. 111:59-66.

Nethery, K. A., C. K. Doyle, B. L. Elsom, N. K. Herzog, V. L. Popov, and J. W. McBride. 2005 Ankyrin repeat containing immunoreactive 200 kD glycoprotein (gp200) orthologs of *Ehrlichia chaffeensis* and *Ehrlichia canis* are translocated to the nuclei of infected monocytes, p. 0-60. In 4th International Conference on Rickettsiae and Rickettsial Diseases, Longrono, Spain.

Nethery, K. A., Doyle C. K., X. F. Zhang, and McBride J. W. 2006. *Ehrlichia canis* gp200 contains five major B cell epitopes defined by O-linked carbohydrate immuno determinants. Infect. Immun.

Nielsen, H., J. Engelbrecht, S. Brunak, and G. von Heijne. 1997. Identification of prokaryotic and eukaryotic signal peptides and prediction of their cleavage sites. Protein Eng 10:1-6.

Obuchowski, M., E. Madec, D. Delattre, G. Boel, A. Iwanicki, D. Foulger, and S. J. Seror. 2000. Characterization of PrpC from *Bacillus subtilis*, a member of the PPM phosphatase family. J Bacteriol 182:5634-5638.

O'Connor, T. P., Esty K. J., MacHenry P., and Hanscom J. L. 2002. Performance evaluation of *Ehrlichia canis* and *Borrelia burgdorferi* peptides in a new *Dirofilaria immitis* combination assay., p. 77-84. In Recent advances in heartworm disease: symposium '01. American Heartworm Society, Batavia, Ill.

O'Connor, T. P., J. L. Hanscom, B. C. Hegarty, R. G. Groat, and E. B. Breitschwerdt. 2006. Comparison of an indirect immunofluorescence assay, western blot analysis, and a commercially available ELISA for detection of *Ehrlichia canis* antibodies in canine sera. Am. J Vet. Res. 67:206-210.

Ohashi, N., A. Unver, N. Zhi, and Y. Rikihisa. 1998. Cloning and characterization of multigenes encoding the immunodominant 30-kilodalton major outer membrane proteins of *Ehrlichia canis* and application of the recombinant protein for serodiagnosis. J. Clin. Microbiol. 36:2671-2680.

Ohashi, N., N. Zhi, Y. Zhang, and Y. Rikihisa. 1998. Immunodominant major outer membrane proteins of *Ehrlichia chaffeensis* are encoded by a polymorphic multigene family. Infect. Immun. 66:132-139.

Reddy, G. R. and C. P. Streck. 2000. Variability in the 28-kDa surface antigen protein multigene locus of isolates of the emerging disease agent *Ehrlichia chaffeensis* suggests that it plays a role in immune evasion [published erratum appears in Mol Cell Biol Res Commun 2000 January; 3(1):66]. Mol. Cell. Biol. Res. Commun. 1:167-175.

Reddy, G. R., C. R. Sulsona, A. F. Barbet, S. M. Mahan, M. J. Burridge, and A. R. Alleman. 1998. Molecular characterization of a 28 kDa surface antigen gene family of the tribe Ehrlichieae. Biochem. Biophys. Res. Commun. 247: 636-643.

Rikihisa, Y., S. A. Ewing, J. C. Fox, A. G. Siregar, F. H. Pasaribu, and M. B. Malole. 1992. Analyses of *Ehrlichia canis* and a canine granulocytic *Ehrlichia* infection. J. Clin. Microbiol. 30:143-148.

Singu, V., H. Liu, C. Cheng, and R. R. Ganta. 2005. *Ehrlichia chaffeensis* expresses macrophage- and tick cell-specific 28-kilodalton outer membrane proteins. Infect. Immun. 73:79-87.

Sirigireddy, K. R. and R. R. Ganta. 2005. Multiplex detection of *Ehrlichia* and *Anaplasma* species pathogens in peripheral blood by real-time reverse transcriptase-polymerase chain reaction. J Mol Diagn 7:308-316.

Stockham, S. L., D. A. Schmidt, K. S. Curtis, B. G. Schauf, J. W. Tyler, and S. T. Simpson. 1992. Evaluation of granulocytic ehrlichiosis in dogs of Missouri, including serologic status to *Ehrlichia canis, Ehrlichia equi* and *Borrelia burgdorferi*. Am. J. Vet. Res. 53:63-68.

Sumner, J. W., J. E. Childs, and C. D. Paddock. 1999. Molecular cloning and characterization of the *Ehrlichia chaffeensis* variable-length PCR target: an antigen-expressing gene that exhibits interstrain variation. J. Clin. Microbiol. 37:1447-1453.

Troy, G. C. and S. D. Forrester. 1990. Canine ehrlichiosis, p. 404-418. In C. E. Green (ed.), Infectious diseases of the dog and cat. W.B. Sauders Co., Philadelphia.

Unver, A., Y. Rikihisa, R. W. Stich, N. Ohashi, and S. Felek. 2002. The omp-1 major outer membrane multigene family of *Ehrlichia chaffeensis* is differentially expressed in canine and tick hosts. Infect. Immun. 70:4701-4704.

Vita et al., 1998, "Novel miniproteins engineered by the transfer of active sites to small natural scaffolds." Biopolymers 47:93-100.

Waner, T., S. Harms, F. Jongejan, H. Bark, A. Keysary, and A. W. Cornelissen. 2001. Significance of serological testing for ehrlichial diseases in dogs with special emphasis on the diagnosis of canine monocytic ehrlichiosis caused by *Ehrlichia canis*. Vet. Parasitol. 95:1-15.

Weisshoff et al., 1999, "Mimicry of beta IF-turns of proteins in cyclic pentapeptides with one and without D-amino acids." Eur. J. Biochem. 259:776-788.

Yabsley, M. J., S. E. Little, E. J. Sims, V. G. Dugan, D. E. Stallknecht, and W. R. Davidson. 2003. Molecular variation in the variable-length PCR target and 120-kilodalton antigen genes of *Ehrlichia chaffeensis* from white-tailed deer (*Odocoileus virginianus*). J. Clin. Microbiol. 41:5202-5206.

Yu, X. J., J. W. McBride, C. M. Diaz, and D. H. Walker. 2000. Molecular cloning and characterization of the 120-kilodalton protein gene of *Ehrlichia canis* and application of the recombinant 120-kilodalton protein for serodiagnosis of canine ehrlichiosis. J. Clin. Microbiol. 38:369-374.

Yu, X. J., J. W. McBride, C. M. Diaz, and D. H. Walker. 2000. Molecular cloning and characterization of the 120-kilodalton protein gene of *Ehrlichia canis* and application of the recombinant 120-kilodalton protein for serodiagnosis of canine ehrlichiosis. J. Clin. Microbiol. 38:369-374.

Yu, X. J., J. W. McBride, X. F. Zhang, and D. H. Walker. 2000. Characterization of the complete transcriptionally active *Ehrlichia chaffeensis* 28 kDa outer membrane protein multigene family. Gene 248:59-68.

Yu, X. J., P. A. Crocquet-Valdes, L. C. Cullman, V. L. Popov, and D. H. Walker. 1999. Comparison of *Ehrlichia chaffeensis* recombinant proteins for serologic diagnosis of human monocytotropic ehrlichiosis. J. Clin. Microbiol. 37:2568-2575.

Yu, X. J., P. Crocquet-Valdes, and D. H. Walker. 1997. Cloning and sequencing of the gene for a 120-kDa immunodominant protein of *Ehrlichia chaffeensis*. Gene 184:149-154.

Yu, X. J., P. Crocquet-Valdes, L. C. Cullman, and D. H. Walker. 1996. The recombinant 120-kilodalton protein of *Ehrlichia chaffeensis*, a potential diagnostic tool. J. Clin. Microbiol. 34:2853-2855.

Yu, X., J. F. Piesman, J. G. Olson, and D. H. Walker. 1997. Short report: geographic distribution of different genetic types of *Ehrlichia chaffeensis*. Am. J Trop. Med Hyg. 56:679-680.

Zhang, X. F., J. Z. Zhang, S. W. Long, R. P. Ruble, and X. J. Yu. 2003. Experimental *Ehrlichia chaffeensis* infection in beagles. J. Med. Microbiol. 52:1021-1026.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of detecting an anti-*E. canis* antibody in an individual, comprising the step of assaying a biological sample from the individual for the presence of an antibody that immunologically binds to a polypeptide comprising the amino acid sequence of SEQ ID NO: 13 or an amino acid sequence that is 95% identical to SEQ ID NO: 13, wherein the polypeptide is 24 to 75 amino acids in length and the assaying comprises contacting the sample with the polypeptide.

2. The method of claim 1, wherein the sample is assayed by contacting with the polypeptide comprising the amino acid sequence of SEQ ID NO: 13.

3. The method of claim 2, wherein the polypeptide is bound to a solid support.

4. The method of claim 3, wherein the solid support is a column matrix, a well of a microtiter plate, a dot blot membrane, or a Western blot membrane.

5. The method of claim 1, wherein the sample is assayed by contacting with the polypeptide comprising the amino acid sequence that is at least 95% identical to SEQ ID NO: 13.

* * * * *

SEQUENCE LISTING

```
<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 1
cacgttcaaa atcatgttga                                                    20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 2
cacgttcaaa atcatgttga                                                    20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:  Synthetic
```

```
      Primer

<400> SEQUENCE: 3
cacgttcaaa atcatgttga                                              20

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
cattttactg gtcctact                                                18

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
tctattgata gtgtaggatg c                                            21

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
gcaggtttag agagctt                                                 17

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
cgcacaatca caacagttgt                                              20

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
gcatactggt ctttcct                                                 17

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer
```

<400> SEQUENCE: 9
agatacttct tgtaactcca tt    22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
agatacttct tgtaactcca tt    22

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
gcatactggt ctttcct    17

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
cgcacaatca caacagttgt    20

<210> SEQ ID NO 13
<211> LENGTH: 24
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 13

His Phe Thr Gly Pro Thr Ser Phe Glu Val Asn Leu Ser Glu Glu Glu
 1               5                  10                  15

Lys Met Glu Leu Gln Glu Val Ser
            20

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
aaaattagtg ttgtggttat g    21

<210> SEQ ID NO 15
<211> LENGTH: 17
<212> TYPE: DNA
<213> ORGANISM: Artificial Sequence

```
<220> FEATURE:
<223> OTHER INFORMATION: Description of Artificial Sequence: Synthetic
      Primer

<400> SEQUENCE: 15
ttttacgctt gctgaat                                                      17

<210> SEQ ID NO 16
<211> LENGTH: 414
<212> TYPE: DNA
<213> ORGANISM: Ehrlichia canis

<400> SEQUENCE: 16
atgttacacg ttcaaaatca tgttgatcaa catacaaatc atatagaaca tgatgattac        60
cattttactg gtcctactag ttttgaagtt aatctttctg aagaagaaaa aatggagtta       120
caagaagtat cttctattga tagtgtagga tgcgaagatt gtgatccaaa ttgtcgttat       180
cctttagaat tagtagaatg tcagcgtatt gaggaaagac cagtatgcaa tgcaggttta       240
gagagcttga ctgttgatgc atcaattag ggattgttgt taggtgggttt tttaagtgct       300
```

```
<220> FEATURE:
<223> OTHER INFORMATION: Description of Artificial Sequence: Synthetic
      Primer

<400> SEQUENCE: 15
ttttacgctt gctgaat                                                      17

<210> SEQ ID NO 16
<211> LENGTH: 414
<212> TYPE: DNA
<213> ORGANISM: Ehrlichia canis

<400> SEQUENCE: 16
atgttacacg ttcaaaatca tgttgatcaa catacaaatc atatagaaca tgatgattac        60
cattttactg gtcctactag ttttgaagtt aatctttctg aagaagaaaa aatggagtta       120
caagaagtat cttctattga tagtgtagga tgcgaagatt gtgatccaaa ttgtcgttat       180
cctttagaat tagtagaatg tcagcgtatt gaggaaagac cagtatgcaa tgcaggttta       240
gagagcttga ctgttgatgc atcaattagg attgttgt taggtggttt tttaagtgct        300
atgaattaca tatcttatag ctatccttgt tattattatg attgttgtga tagaaattat       360
tacgactgtt gtcataagaa tgcgtgttat tacaactgtt gtgattgtgc gtaa             414

<210> SEQ ID NO 17
<211> LENGTH: 137
<212> TYPE: PRT
<213> ORGANISM: Ehrlichia canis

<400> SEQUENCE: 17

Met Leu His Val Gln Asn His Val Asp Gln His Thr Asn His Ile Glu
  1               5                  10                  15

His Asp Asp Tyr His Phe Thr Gly Pro Thr Ser Phe Glu Val Asn Leu
                 20                  25                  30

Ser Glu Glu Lys Met Glu Leu Gln Glu Val Ser Ser Ile Asp Ser
             35                  40                  45

Val Gly Cys Glu Asp Cys Asp Pro Asn Cys Arg Tyr Pro Leu Glu Leu
 50                  55                  60

Val Glu Cys Gln Arg Ile Glu Glu Arg Pro Val Cys Asn Ala Gly Leu
 65                  70                  75                  80

Glu Ser Leu Thr Val Asp Ala Tyr Gln Leu Gly Leu Leu Gly Gly
                 85                  90                  95

Phe Leu Ser Ala Met Asn Tyr Ile Ser Tyr Ser Tyr Pro Cys Tyr Tyr
                100                 105                 110

Tyr Asp Cys Cys Asp Arg Asn Tyr Tyr Asp Cys Cys His Lys Asn Ala
            115                 120                 125

Cys Tyr Tyr Asn Cys Cys Asp Cys Ala
            130                 135

<210> SEQ ID NO 18
<211> LENGTH: 414
<212> TYPE: DNA
<213> ORGANISM: Ehrlichia canis

<400> SEQUENCE: 18
atgttacacg ttcaaaatca tgttgatcaa catacaaatc atatagaaca tgatgattac        60
cattttactg atcctactag ttttgaagtt aatctttctg aagaagaaaa aatggagtta       120
caagaagtat cttctattga tagtgtagga tgcgaagatt gtgatccaaa ttgtcgttat       180
```

-continued

```
cctttagaat tagtagaatg tcagcgtatt gaggaaagac cagtatgcaa tgcaggttta    240
gagagcttga ctgttgatgc atatcaatta ggattgttgt taggtggttt tttaagtgct    300
atgaattaca tatcttatag ctatccttgt tattattatg attgttgtga tagaaattat    360
tacgactgtt gtcataagaa tgcgtgttat tacaactgtt gtgattgtgc gtaa          414
```

<210> SEQ ID NO 19
<211> LENGTH: 137
<212> TYPE: PRT
<213> ORGANISM: Ehrlichia canis

<400> SEQUENCE: 19

```
Met Leu His Val Gln Asn His Val Asp Gln His Thr Asn His Ile Glu
  1               5                  10                  15

His Asp Asp Tyr His Phe Thr Asp Pro Thr Ser Phe Glu Val Asn Leu
             20                  25                  30

Ser Glu Glu Glu Lys Met Glu Leu Gln Glu Val Ser Ser Ile Asp Ser
         35                  40                  45

Val Gly Cys Glu Asp Cys Asp Pro Asn Cys Arg Tyr Pro Leu Glu Leu
     50                  55                  60

Val Glu Cys Gln Arg Ile Glu Glu Arg Pro Val Cys Asn Ala Gly Leu
 65                  70                  75                  80

Glu Ser Leu Thr Val Asp Ala Tyr Gln Leu Gly Leu Leu Gly Gly
                 85                  90                  95

Phe Leu Ser Ala Met Asn Tyr Ile Ser Tyr Ser Tyr Pro Cys Tyr Tyr
                100                 105                 110

Tyr Asp Cys Cys Asp Arg Asn Tyr Tyr Asp Cys Cys His Lys Asn Ala
            115                 120                 125

Cys Tyr Tyr Asn Cys Cys Asp Cys Ala
        130                 135
```

<210> SEQ ID NO 20
<211> LENGTH: 72
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 20

```
cattttactg gtcctactag ttttgaagtt aatctttctg aagaagaaaa aatggagtta    60
caagaagtat ct                                                        72
```